(12) United States Patent
Field et al.

(10) Patent No.: US 8,319,654 B2
(45) Date of Patent: Nov. 27, 2012

(54) APPARATUS HAVING ELECTROLYSIS CELL AND INDICATOR LIGHT ILLUMINATING THROUGH LIQUID

(75) Inventors: Bruce F. Field, Golden Valley, MN (US); Todd R. Schaeffer, St. Michael, MN (US)

(73) Assignee: Tennant Company, Minneapolis, MN (US)

( * ) Notice: Subject to any disclaimer, the term of this patent is extended or adjusted under 35 U.S.C. 154(b) by 654 days.

(21) Appl. No.: 12/488,368

(22) Filed: Jun. 19, 2009

(65) Prior Publication Data

US 2009/0314651 A1 Dec. 24, 2009

Related U.S. Application Data

(60) Provisional application No. 61/092,586, filed on Aug. 28, 2008.

(51) Int. Cl.
*G08B 5/00* (2006.01)
*G08B 21/00* (2006.01)
*B65D 5/66* (2006.01)

(52) U.S. Cl. ............... 340/815.4; 340/500; 340/591; 340/603; 340/636.2; 340/691.1; 340/691.6; 204/194; 204/271; 205/687; 239/375; 239/525; 222/113; 222/321.7; 362/101; 362/154

(58) Field of Classification Search .......... 340/815.4
See application file for complete search history.

(56) References Cited

U.S. PATENT DOCUMENTS

| | | | |
|---|---|---|---|
| 2,288,956 A * | 7/1942 | Rosenkoetter | 40/406 |
| 3,725,226 A | 4/1973 | Stoner | 204/149 |
| 3,859,195 A | 1/1975 | Williams | 204/272 |
| 3,897,320 A | 7/1975 | Cook, Jr. | 204/95 |
| 3,933,614 A | 1/1976 | Bunn, Jr. | 204/266 |
| 4,018,658 A | 4/1977 | Alfin et al. | 204/109 |
| 4,099,489 A | 7/1978 | Bradley | 123/3 |
| 4,105,528 A | 8/1978 | Hasebe | 204/237 |
| 4,108,052 A | 8/1978 | Cunningham | 99/275 |
| 4,121,543 A | 10/1978 | Hicks, Jr. et al. | 123/3 |
| 4,129,493 A | 12/1978 | Tighe et al. | 204/228 |
| 4,154,578 A | 5/1979 | Bane | 8/137 |
| 4,244,079 A | 1/1981 | Bane | 15/321 |
| 4,324,635 A | 4/1982 | Sweeney | 204/266 |
| 4,374,711 A | 2/1983 | Ogawa | 204/98 |
| 4,405,418 A | 9/1983 | Takemura | 204/95 |

(Continued)

FOREIGN PATENT DOCUMENTS
AU 732602 4/2001
(Continued)

OTHER PUBLICATIONS

Office Action from the United States Patent and Trademark Office for U.S. Appl. No. 11/655,359, dated Nov. 13, 2009.

(Continued)

*Primary Examiner* — Donnie Crosland
(74) *Attorney, Agent, or Firm* — David D. Brush; Westman, Champlin & Kelly, P.A.

(57) ABSTRACT

An apparatus is provided, which includes an electrolysis cell, a liquid flow path that passes through the electrolysis cell, and an indicator light. The indicator light is illuminated as a function of an operating characteristic of the electrolysis cell and luminous flux radiated from the light illuminates liquid along at least a portion of the flow path.

15 Claims, 26 Drawing Sheets

U.S. PATENT DOCUMENTS

| | | | | |
|---|---|---|---|---|
| 4,502,929 | A | 3/1985 | Stewart et al. | 204/147 |
| 4,574,037 | A | 3/1986 | Samejima et al. | 204/98 |
| 4,600,495 | A | 7/1986 | Fogt | 204/409 |
| 4,603,167 | A | 7/1986 | Mahalek et al. | 524/706 |
| 4,630,167 | A | 12/1986 | Huggins | 361/213 |
| 4,663,091 | A | 5/1987 | Seo | 261/72.1 |
| 4,670,113 | A | 6/1987 | Lewis | 204/80 |
| 4,676,882 | A | 6/1987 | Okazaki | 204/260 |
| 4,687,558 | A | 8/1987 | Justice et al. | 204/59 |
| 4,705,191 | A | 11/1987 | Itzel et al. | 222/80 |
| 4,734,176 | A | 3/1988 | Zemba, Jr. et al. | 204/149 |
| 4,810,344 | A | 3/1989 | Okazaki | 204/228 |
| 4,832,230 | A | 5/1989 | Janowitz | 222/80 |
| 4,875,988 | A | 10/1989 | Aragon | 204/265 |
| 4,956,071 | A | 9/1990 | Giuffrida et al. | 204/301 |
| 5,186,860 | A | 2/1993 | Joyce, Jr. et al. | 252/500 |
| 5,234,563 | A | 8/1993 | Arai et al. | 204/229 |
| 5,250,161 | A | 10/1993 | Chin et al. | 204/131 |
| 5,292,406 | A | 3/1994 | Wanngard et al. | 204/95 |
| 5,316,646 | A | 5/1994 | Arai | 204/306 |
| 5,320,718 | A | 6/1994 | Molter et al. | 204/101 |
| 5,378,339 | A | 1/1995 | Aoki et al. | 204/260 |
| 5,536,389 | A | 7/1996 | La Naour et al. | 205/688 |
| 5,590,439 | A | 1/1997 | Alazet | |
| 5,593,476 | A | 1/1997 | Coppom | 95/78 |
| 5,632,870 | A | 5/1997 | Kucherov | 204/241 |
| 5,661,237 | A | 8/1997 | Dussan et al. | 73/152.18 |
| 5,665,212 | A | 9/1997 | Zhong et al. | 304/297 |
| 5,733,434 | A | 3/1998 | Harada et al. | 205/746 |
| 5,762,779 | A | 6/1998 | Shiramizu et al. | 205/746 |
| 5,766,438 | A | 6/1998 | Ishibashi et al. | 204/520 |
| 5,779,891 | A | 7/1998 | Andelman | 210/198.2 |
| 5,815,869 | A | 10/1998 | Hopkins | 8/158 |
| 5,824,200 | A | 10/1998 | Kitajima et al. | 204/265 |
| 5,835,680 | A | 11/1998 | Glucksman et al. | 392/501 |
| 5,853,562 | A | 12/1998 | Eki et al. | |
| 5,858,201 | A | 1/1999 | Otsuka et al. | 205/701 |
| 5,858,202 | A | 1/1999 | Nakamura | 205/746 |
| 5,928,505 | A | 7/1999 | Inakagata et al. | 210/91 |
| 5,931,859 | A | 8/1999 | Burke | 607/66 |
| 5,997,717 | A | 12/1999 | Miyashita et al. | 205/466 |
| 6,016,973 | A | 1/2000 | Thompson et al. | 239/304 |
| 6,032,655 | A | 3/2000 | Kavonius | 123/538 |
| 6,059,941 | A | 5/2000 | Bryson et al. | 204/263 |
| 6,088,211 | A | 7/2000 | Pitel | 361/212 |
| 6,101,671 | A | 8/2000 | Wright et al. | 15/365 |
| 6,110,353 | A | 8/2000 | Hough | 205/701 |
| 6,132,572 | A | 10/2000 | Kim | |
| 6,200,434 | B1 | 3/2001 | Shinjo et al. | 204/230.2 |
| 6,231,747 | B1 | 5/2001 | Fukuzuka et al. | |
| 6,315,886 | B1 | 11/2001 | Zappi et al. | |
| 6,336,430 | B2 * | 1/2002 | de Souza et al. | 123/3 |
| 6,375,827 | B1 | 4/2002 | Kurosu et al. | 205/687 |
| 6,379,628 | B2 | 4/2002 | de Jong et al. | |
| 6,409,895 | B1 | 6/2002 | Ponzano | 204/260 |
| 6,425,958 | B1 | 7/2002 | Giddings et al. | 134/21 |
| 6,488,016 | B2 | 12/2002 | Kavonius | 123/538 |
| 6,502,766 | B1 | 1/2003 | Streutker et al. | |
| 6,585,827 | B2 | 7/2003 | Field et al. | 134/6 |
| 6,638,364 | B2 | 10/2003 | Harkins et al. | 134/21 |
| 6,652,719 | B1 | 11/2003 | Tseng | 204/257 |
| 6,656,334 | B2 | 12/2003 | Tseng et al. | 204/276 |
| 6,689,262 | B2 | 2/2004 | Senkiw | 204/278.5 |
| 6,703,785 | B2 | 3/2004 | Aiki et al. | 315/111.81 |
| 6,719,891 | B2 | 4/2004 | Ruhr et al. | |
| 6,735,812 | B2 | 5/2004 | Heckman et al. | 15/320 |
| 6,842,940 | B2 | 1/2005 | Christopher et al. | 15/320 |
| 6,855,233 | B2 | 2/2005 | Sawada | |
| 6,878,287 | B1 | 4/2005 | Marais | 210/748 |
| 6,921,743 | B2 | 7/2005 | Scheper et al. | |
| 6,926,819 | B2 | 8/2005 | Nakamura et al. | |
| 6,964,739 | B2 | 11/2005 | Boyd et al. | |
| 6,974,561 | B1 | 12/2005 | Thomason | |
| 6,991,593 | B2 | 1/2006 | Price et al. | 588/252 |
| 7,008,523 | B2 | 3/2006 | Herrington | 205/701 |
| 7,011,739 | B2 | 3/2006 | Harkins et al. | 205/701 |
| 7,059,013 | B2 | 6/2006 | Wydra et al. | 15/345 |
| 7,107,046 | B1 | 9/2006 | Mainard et al. | 455/414.2 |
| 7,156,962 | B2 | 1/2007 | Koizumi et al. | |
| 7,160,472 | B2 | 1/2007 | Vliet et al. | |
| 7,226,542 | B2 | 6/2007 | Zemel et al. | |
| 7,238,272 | B2 | 7/2007 | Sano | 205/701 |
| 7,303,300 | B2 * | 12/2007 | Dowling et al. | 362/101 |
| 7,309,136 | B2 * | 12/2007 | Lei | 362/101 |
| 7,836,543 | B2 | 11/2010 | Field et al. | 15/320 |
| 7,891,046 | B2 | 2/2011 | Field et al. | 15/320 |
| 8,007,654 | B2 | 8/2011 | Field et al. | 205/746 |
| 8,012,339 | B2 | 9/2011 | Field | 205/701 |
| 8,012,340 | B2 | 9/2011 | Field et al. | 205/746 |
| 8,025,786 | B2 | 9/2011 | Field et al. | 205/746 |
| 8,025,787 | B2 | 9/2011 | Field et al. | 205/746 |
| 8,046,867 | B2 | 11/2011 | Field et al. | 15/320 |
| 8,062,499 | B2 * | 11/2011 | Field | 205/337 |
| 2001/0002500 | A1 | 6/2001 | Kasen et al. | 15/320 |
| 2001/0034922 | A1 | 11/2001 | Ko | 15/320 |
| 2002/0023847 | A1 | 2/2002 | Natsume | |
| 2002/0027070 | A1 | 3/2002 | Oyokota et al. | 204/257 |
| 2002/0032141 | A1 | 3/2002 | Harkins | 510/253 |
| 2002/0038768 | A1 | 4/2002 | Kasuya | 205/701 |
| 2002/0074237 | A1 | 6/2002 | Takesako et al. | 205/628 |
| 2002/0112314 | A1 | 8/2002 | Harkins | 15/321 |
| 2002/0185423 | A1 | 12/2002 | Boyd et al. | 210/167 |
| 2003/0001439 | A1 | 1/2003 | Schur | 310/11 |
| 2003/0062068 | A1 | 4/2003 | Ko et al. | 134/28 |
| 2003/0070919 | A1 | 4/2003 | Gilmore | 204/275.1 |
| 2003/0102270 | A1 | 6/2003 | Schoeberl | 210/748 |
| 2003/0159230 | A1 | 8/2003 | Oh | |
| 2003/0159231 | A1 | 8/2003 | Oh | 15/320 |
| 2003/0159233 | A1 | 8/2003 | Oh | 15/321 |
| 2003/0164306 | A1 | 9/2003 | Senkiw | 205/633 |
| 2003/0213505 | A1 | 11/2003 | Price et al. | |
| 2004/0011665 | A1 | 1/2004 | Koizumi et al. | 205/626 |
| 2004/0012913 | A1 | 1/2004 | Andelman | 361/503 |
| 2004/0037737 | A1 | 2/2004 | Marais et al. | 422/28 |
| 2004/0042201 | A1 * | 3/2004 | Lee | 362/101 |
| 2004/0069611 | A1 | 4/2004 | MacGregor | 204/157.15 |
| 2004/0094432 | A1 | 5/2004 | Neel et al. | 205/777.5 |
| 2004/0112763 | A1 | 6/2004 | Itoh et al. | 205/746 |
| 2004/0166019 | A1 | 8/2004 | Schultheiss | 422/22 |
| 2004/0168933 | A1 | 9/2004 | Inoue | |
| 2004/0226123 | A1 | 11/2004 | Policicchio et al. | 15/115 |
| 2004/0250323 | A1 | 12/2004 | Arai et al. | D32/1 |
| 2004/0256247 | A1 | 12/2004 | Carson et al. | 205/688 |
| 2005/0067289 | A1 | 3/2005 | Noji et al. | 205/83 |
| 2005/0103644 | A1 | 5/2005 | Wilkins et al. | 205/751 |
| 2005/0121334 | A1 | 6/2005 | Sumita | 205/628 |
| 2005/0126928 | A1 | 6/2005 | Hung et al. | |
| 2005/0136520 | A1 | 6/2005 | Kinley et al. | 435/155 |
| 2005/0139239 | A1 | 6/2005 | Prae | |
| 2005/0139465 | A1 | 6/2005 | Kasuya et al. | 204/271 |
| 2005/0139808 | A1 | 6/2005 | Alimi | |
| 2005/0194261 | A1 | 9/2005 | Hadia | 205/701 |
| 2005/0244556 | A1 | 11/2005 | Karren | |
| 2006/0037869 | A1 | 2/2006 | Mitchke | |
| 2006/0054205 | A1 | 3/2006 | Yabe et al. | 134/184 |
| 2006/0076248 | A1 | 4/2006 | Kindred | |
| 2006/0162735 | A1 | 7/2006 | Thiebaut | 132/200 |
| 2006/0169575 | A1 | 8/2006 | Sumita | |
| 2006/0231503 | A1 | 10/2006 | Flettner | 210/748 |
| 2006/0263240 | A1 | 11/2006 | Hopkins | 422/28 |
| 2006/0280664 | A1 | 12/2006 | Huang et al. | |
| 2007/0009376 | A1 | 1/2007 | Hamada et al. | 422/20 |
| 2007/0023273 | A1 | 2/2007 | Kitaori et al. | |
| 2007/0037267 | A1 | 2/2007 | Lewis et al. | 435/161 |
| 2007/0141434 | A1 | 6/2007 | Joshi et al. | |
| 2007/0170072 | A1 | 7/2007 | Shyu | 205/701 |
| 2007/0186367 | A1 | 8/2007 | Field et al. | 15/320 |
| 2007/0186368 | A1 | 8/2007 | Field et al. | 15/320 |
| 2007/0186369 | A1 | 8/2007 | Field et al. | 15/320 |
| 2007/0186954 | A1 | 8/2007 | Field et al. | 134/6 |
| 2007/0186957 | A1 | 8/2007 | Field et al. | 134/18 |
| 2007/0186958 | A1 | 8/2007 | Field et al. | 134/21 |
| 2007/0187261 | A1 | 8/2007 | Field et al. | 205/742 |
| 2007/0187262 | A1 | 8/2007 | Field et al. | 205/742 |
| 2007/0187263 | A1 | 8/2007 | Field et al. | 205/742 |
| 2007/0272549 | A1 | 11/2007 | Davis et al. | 204/260 |
| 2008/0264778 | A1 | 10/2008 | Joshi et al. | |

| | | | | | | |
|---|---|---|---|---|---|---|
| 2008/0272060 | A1 | 11/2008 | Taguchi et al. ............... 210/748 | JP | 11090442 | 9/1997 |
| 2009/0008268 | A1 | 1/2009 | Salathe et al. ............... 205/746 | JP | 10057282 | 3/1998 |
| 2009/0127128 | A1 | 5/2009 | Kitaori et al. ............... 205/464 | JP | 11010159 A | 1/1999 |
| 2009/0148342 | A1 | 6/2009 | Bromberg et al. ............... 422/37 | JP | 11057715 | 3/1999 |
| 2009/0162505 | A1 | 6/2009 | Kriebel et al. ............... 426/335 | JP | 11128941 | 5/1999 |
| 2009/0184186 | A1 | 7/2009 | Suda et al. ............... 239/690 | JP | 11180992 | 7/1999 |
| 2009/0212132 | A1 | 8/2009 | Simmonds et al. ............... 239/289 | JP | 2000079393 A | 3/2000 |
| 2009/0235481 | A1 | 9/2009 | Gosebruch et al. ............... 15/320 | JP | 2001-181900 | 3/2001 |
| 2010/0189805 | A1 | 7/2010 | Saefkow et al. ............... 424/600 | JP | 2002-102856 | 4/2002 |
| 2010/0192987 | A1 | 8/2010 | Steffen et al. ............... 134/34 | JP | 2002-186969 | 7/2002 |
| | | | | JP | 2003062573 A | 3/2003 |

FOREIGN PATENT DOCUMENTS

| | | | | | |
|---|---|---|---|---|---|
| JP | 2003181338 A | 7/2003 |
| CN | 1379737 | 11/2002 | JP | 2003261190 A | 9/2003 |
| CN | 1440711 | 9/2003 | JP | 2003266073 A | 9/2003 |
| CN | 1845877 A | 10/2006 | JP | 2003-334548 | 11/2003 |
| CN | 200977495 Y | 11/2007 | JP | 2003334557 A | 11/2003 |
| DE | 2951993 | 7/1981 | JP | 2004-073914 | 3/2004 |
| DE | 8430251 | 6/1984 | JP | 2004-121962 | 4/2004 |
| DE | 8430251 U1 | 6/1984 | JP | 2004-129954 | 4/2004 |
| DE | 4406320 | 8/1995 | JP | 2004148108 A | 5/2004 |
| DE | 19752174 | 7/1998 | JP | 2004148109 A | 5/2004 |
| DE | 20210562 | 10/2002 | JP | 2005-006816 | 1/2005 |
| DE | 202004010572 U1 | 11/2004 | JP | 2005-052787 | 3/2005 |
| DE | 202007005471 | 6/2007 | JP | 2005-535783 | 11/2005 |
| DE | 202007004181 U1 | 8/2007 | JP | 2006-036341 | 9/2006 |
| DE | 102007017502 | 10/2008 | JP | 2007-000402 | 1/2007 |
| EP | 0041373 | 12/1981 | JP | 2007-136356 | 6/2007 |
| EP | 0104345 | 4/1984 | JP | 2007-239041 | 9/2007 |
| EP | 0199493 | 10/1986 | KR | 20010096847 A | 11/2001 |
| EP | 0438902 | 7/1991 | KR | 2002-0025023 | 11/2003 |
| EP | 0636581 | 2/1995 | KR | 2006-0007369 | 1/2006 |
| EP | 0663176 A1 | 7/1995 | KR | 100599229 | 7/2006 |
| EP | 0672623 | 9/1995 | KR | 2009-0123297 | 12/2009 |
| EP | 0674026 | 9/1995 | NL | 1012257 C2 | 12/2000 |
| EP | 0740329 | 10/1996 | WO | 8606098 | 10/1986 |
| EP | 761235 B1 | 3/1997 | WO | 9640591 | 12/1996 |
| EP | 1000554 B1 | 5/2000 | WO | 9818723 | 5/1998 |
| EP | 1008662 | 6/2000 | WO | 9846874 | 10/1998 |
| EP | 1162176 | 12/2001 | WO | 9908719 A2 | 2/1999 |
| EP | 1188719 | 3/2002 | WO | 9963843 A1 | 12/1999 |
| EP | 1293481 B1 | 3/2003 | WO | 0015561 | 3/2000 |
| EP | 1308421 | 5/2003 | WO | 0118279 | 3/2001 |
| EP | 1065170 | 1/2004 | WO | 0127037 | 4/2001 |
| EP | 1386995 | 2/2004 | WO | 0214228 A2 | 2/2002 |
| EP | 1309519 B1 | 9/2004 | WO | 02066382 A1 | 8/2002 |
| EP | 1533041 A1 | 5/2005 | WO | 02102716 | 12/2002 |
| EP | 1671560 | 6/2006 | WO | 03009920 | 2/2003 |
| EP | 1741676 A2 | 1/2007 | WO | 03022444 | 3/2003 |
| EP | 1754804 | 2/2007 | WO | 03022745 | 3/2003 |
| EP | 1903128 A2 | 3/2008 | WO | 03040038 | 5/2003 |
| EP | 1932809 | 6/2008 | WO | 2004015172 | 2/2004 |
| EP | 1941912 A1 | 7/2008 | WO | 2004079051 | 9/2004 |
| EP | 1978142 | 10/2008 | WO | 2004106242 A1 | 12/2004 |
| EP | 2050378 | 4/2009 | WO | 2004108607 | 12/2004 |
| EP | 2078700 | 7/2009 | WO | 2005014058 A1 | 2/2005 |
| EP | 2078701 | 7/2009 | WO | 2005020780 | 3/2005 |
| EP | 2100623 | 9/2009 | WO | 2005079468 | 9/2005 |
| EP | 2103244 | 9/2009 | WO | 2005084786 | 9/2005 |
| EP | 2168604 | 3/2010 | WO | 2005093129 | 10/2005 |
| FR | 2381835 | 9/1978 | WO | 2005094904 | 10/2005 |
| FR | 2909370 A1 | 6/2008 | WO | 2005097350 | 10/2005 |
| GB | 611819 | 11/1948 | WO | 2005012186 A1 | 2/2006 |
| GB | 2149423 | 11/1983 | WO | 2006098041 | 9/2006 |
| GB | 2141738 | 1/1985 | WO | 2006124805 | 11/2006 |
| GB | 2298858 | 9/1996 | WO | 2007031779 | 3/2007 |
| GB | 2381187 | 4/2003 | WO | 2007057146 | 5/2007 |
| GB | 2393737 | 4/2004 | WO | 2007092597 | 8/2007 |
| JP | 62023663 | 2/1987 | WO | 2007093395 | 8/2007 |
| JP | 1111483 | 4/1989 | WO | 2007095072 | 8/2007 |
| JP | 03157188 | 7/1991 | WO | 2007095074 | 8/2007 |
| JP | 04058931 | 2/1992 | WO | 2007138363 | 12/2007 |
| JP | 06206522 | 12/1993 | WO | 2007142693 | 12/2007 |
| JP | 06182342 | 7/1994 | WO | 2007145058 | 12/2007 |
| JP | 07233493 | 9/1995 | WO | 2007145385 | 12/2007 |
| JP | 07263391 | 10/1995 | WO | 2008032544 A1 | 3/2008 |
| JP | 07263398 | 10/1995 | WO | 2008061546 A1 | 5/2008 |
| JP | 08112574 | 5/1996 | WO | 2008131389 A1 | 10/2008 |
| JP | 09075427 | 3/1997 | WO | 2009011841 | 1/2009 |
| JP | 1997174054 A | 7/1997 | WO | 2009039674 | 4/2009 |

| | | |
|---|---|---|
| WO | 2009040407 | 4/2009 |
| WO | 2009046563 | 4/2009 |
| WO | 2009067838 | 6/2009 |
| WO | 2009155546 | 12/2009 |
| WO | 2010028031 | 3/2010 |
| WO | 2010055108 | 5/2010 |
| WO | 2010077968 | 7/2010 |

OTHER PUBLICATIONS

Restriction Requirement from the United States Patent and Trademark Office for U.S. Appl. No. 11/655,385, dated Dec. 9, 2009.
Final Office Action from the United States Patent and Trademark Office for U.S. Appl. No. 11/655,390, dated Jan. 11, 2010.
Office Action from the United States Patent and Trademark Office for U.S. Appl. No. 11/655,378, dated Jan. 14, 2010.
Office Action from the United States Patent and Trademark Office for U.S. Appl. No. 11/655,385, dated Jan. 29, 2010.
Written Opinion dated Dec. 11, 2009 from International Application No. PCT/US2009/048008, filed Jun. 19, 2009.
Written Opinion dated Dec. 28, 2009 from International Application No. PCT/US2009/048009, filed Jun. 19, 2009.
International Search Report dated Dec. 11, 2009 for International Application No. PCT/US2009/048008, filed Jun. 19, 2009.
International Search Report dated Dec. 28, 2009 for International Application No. PCT/US2009/048009, filed Jun. 19, 2009.
Derrick, Julyne, "How to Remove your Makeup" Jan. 2, 2008. http://beauty.about.com/od/makeuptrickstips/qt/removemakeup.html.
Notice of Allowance from the United States Patent and Trademark Office for U.S. Appl. No. 11/655,378, dated Apr. 28, 2011.
Notice of Allowance from the United States Patent and Trademark Office for U.S. Appl. No. 11/655,378, dated May 10, 2011.
Notice of Allowance from the United States Patent and Trademark Office for U.S. Appl. No. 11/655,359, dated Aug. 11, 2011.
Restriction Requirement from the United States Patent and Trademark Office for U.S. Appl. No. 12/481,115, dated Oct. 11, 2011.
Office Action from the United States Patent and Trademark Office for U.S. Appl. No. 11/655,365, dated Oct. 12, 2011.
Restriction Requirement from the United States Patent and Trademark Office for U.S. Appl. No. 12/522,508, dated Nov. 8, 2011.
Restriction Requirement from the United States Patent and Trademark Office for U.S. Appl. No. 12/481,115, dated Dec. 6, 2011.
Office Action from the United States Patent and Trademark Office for U.S. Appl. No. 12/481,098, dated Dec. 29, 2011.
Office Action from the United States Patent and Trademark Office for U.S. Appl. No. 12/552,508, dated Jan. 20, 2012.
Notice of Allowance from the United States Patent and Trademark Office for U.S. Appl. No. 11/655,365, dated Jan. 24, 2012.
Aoki et al., "Wafer Treatment Using Electrolysis-Ionized Water", 1994, Jpn. J. Appl. Phys. vol. 33, pp. 5686-5689.
Bluhm, Hans J. et al., "Disruption and Destruction of Biological Cells Using Strong Pulsed Electric Fields" Nachrichten, Karlsruhe, DE, vol. 3, Jan. 1, 2005, pp. 105-110.
Final Office Action from the United States Patent and Trademark Office for U.S. Appl. No. 11/655,378, dated Jul. 2, 2010.
Notice of Allowance from the United States Patent and Trademark Office for U.S. Appl. No. 11/655,385, dated Jul. 14, 2010.
Office Action from the United States Patent and Trademark Office for U.S. Appl. No. 11/655,390, dated Jul. 19, 2010.
Restriction/Election Requirement from the United States Patent and Trademark Office for U.S. Appl. No. 11/655,365, dated Aug. 17, 2010.
Office Action from the United States Patent and Trademark Office for U.S. Appl. No. 11/655,359, dated Aug. 18, 2010.
Office Action from the United States Patent and Trademark Office for U.S. Appl. No. 11/655,378, dated Sep. 9, 2010.
Office Action from the United States Patent and Trademark Office for U.S. Appl. No. 11/655,415, dated Sep. 29, 2010.
Office Action from the United States Patent and Trademark Office for U.S. Appl. No. 11/655,360, dated Sep. 30, 2010.
Office Action from the United States Patent and Trademark Office for U.S. Appl. No. 12/122,350, dated Sep. 30, 2010.
Office Action from the United States Patent and Trademark Office for U.S. Appl. No. 11/655,310, dated Oct. 1, 2010.
Office Action from the United States Patent and Trademark Office for U.S. Appl. No. 11/655,389, dated Oct. 1, 2010.
Office Action from the United States Patent and Trademark Office for U.S. Appl. No. 11/655,365, dated Dec. 3, 2010.
Notice of Allowance from the United States Patent and Trademark Office for U.S. Appl. No. 11/655,390, dated Jan. 6, 2011.
Final Office Action from the United States Patent and Trademark Office for U.S. Appl. No. 11/655,378, dated Jan. 25, 2011.
Office Action from the United States Patent and Trademark Office for U.S. Appl. No. 11/655,359, dated Feb. 3, 2011.
Notice of Allowance from the United States Patent and Trademark Office for U.S. Appl. No. 12/122,350, dated Mar. 16, 2011.
Notice of Allowance from the United States Patent and Trademark Office for U.S. Appl. No. 11/655,389, dated Mar. 17, 2011.
Notice of Allowance from the United States Patent and Trademark Office for U.S. Appl. No. 11/655,360, dated Mar. 18, 2011.
Notice of Allowance from the United States Patent and Trademark Office for U.S. Appl. No. 11/655,415, dated Mar. 23, 2011.
Notice of Allowance from the United States Patent and Trademark Office for U.S. Appl. No. 11/655,310, dated Mar. 23, 2011.
European Patent Office Communication dated Apr. 29, 2011 for corresponding European Application No. 09789861.3-2104.
JP-HC15022149.
"Fast-Foam Scrubbing Technology, The Safe Scrubbing Alternative,T5-Parts Manual," Tennant Company,www.tennantco.com, 2006.
"Fast-Foam Scrubbing Technology, The Safe Scrubbing Alternative, T5-Scrubber-Dryer Operator Manual," Tennant Company, www.tennantco.com, 2006.
"ECO Smarte—The Best Multiple Mineral Technology for Problem Well Water; The Best Chemical Reduction System for City Water Complete Bacteria and Scale Control," ECOsmarte® Planet Friendly, Inc., http://www.ecosmarte.com/sciencesummary.html, 1994, pp. 1-13.
"Krebs Engineers® Products," 2006 Krebs Engineers,http//www.krebs.com/about.php/ and http://www.krebs.com/products/php/product/20/CycloClean%AE+Modules, 2006, pp. 1-3.
"The OXYGENATOR Livelier Bait-Healthier fish," Aqua Innovations, Inc., aquainnovationsinc.com, published prior toJan. 19, 2007, pp. 1-2.
"JP102 Water Cell," Emco Tech Co., Ltd. of Goyang-City Kyungki-Do, South Korea, Oct. 18, 2006, pp. 1.
Mary Jones, "Richfield-Based EcoSmarte has Perfected a Natural-and Profitable-Approach to Water Purification,"Minnesota Technology, Inside Technology and Manufacturing Business, Fall 2005, pp. 1-3.
Office Action from the United States Patent and Trademark Office for U.S. Appl. No. 11/655,390, dated Jan. 19, 2007.
Office Action from the United States Patent and Trademark Office for U.S. Appl. No. 11/655,359, dated Mar. 19, 2009.
Restriction Requirement from the United States Patent and Trademark Office for U.S. Appl. No. 11/655,390, dated Apr. 10, 2009.
Office Action from the United States Patent and Trademark Office for U.S. Appl. No. 11/655,390, dated Jul. 16, 2009.
Written Opinion dated Oct. 22, 2009 from International Application No. PCT/US2009/047979, filed Jun. 19, 2009.
International Search Report dated Oct. 22, 2009 for International Application No. PCT/US2009/047979, filed Jun. 19, 2009.
"Conductive Polymers: Evaluation of Industrial Applications" Synthetic Metals, 55-57 (1993) 3623-3631 S. Roth et al.
Written Opinion dated Oct. 7, 2009 from International Application No. PCT/US2009/047971, filed Jun. 19, 2009.
Written Opinion dated Sep. 30, 2009 from International Application No. PCT/US2009/048005, filed Jun. 19, 2009.
International Search Report dated Oct. 7, 2009 for International Application No. PCT/US2009/047971, filed Jun. 19, 2009.
International Search Report dated Sep. 30, 2009 for International Application No. PCT/US2009/048005, filed Jun. 19, 2009.
Office Action from the United States Patent and Trademark Office for U.S. Appl. No. 12/481,115, dated Jan. 31, 2012.

Office Action from the United States Patent and Trademark Office for U.S. Appl. No. 12/245,213, dated Feb. 2, 2012.
Office Action from the United States Patent and Trademark Office for U.S. Appl. No. 12/488,301, dated Mar. 13, 2012.
Restriction Requirement from the United States Patent and Trademark Office for U.S. Appl. No. 12/693,114, dated Mar. 13, 2012.
Restriction Requirement from the United States Patent and Trademark Office for U.S. Appl. No. 12/835,441, dated Mar. 14, 2012.
Office Action from the United States Patent and Trademark Office for U.S. Appl. No. 12/835,441, dated Mar. 27, 2012.
Notice of Allowance from the United States Patent and Trademark Office for U.S. Appl. No. 12/488,360, dated Mar. 29, 2012.
Office Action from the United States Patent and Trademark Office for U.S. Appl. No. 12/488,316, dated Apr. 9, 2012.
Final Office Action from the United States Patent and Trademark Office for U.S. Appl. No. 12/481,098, dated Apr. 17, 2012.
Office Action from the United States Patent and Trademark Office for U.S. Appl. No. 12/693,114, dated Apr. 19, 2012.
Office Action from the United States Patent and Trademark Office for U.S. Appl. No. 12/488,349, dated Apr. 24, 2012.
Office Action dated Jul. 12, 2012 for corresponding Mexican Patent Application No. MX/a/2011/002261.

* cited by examiner

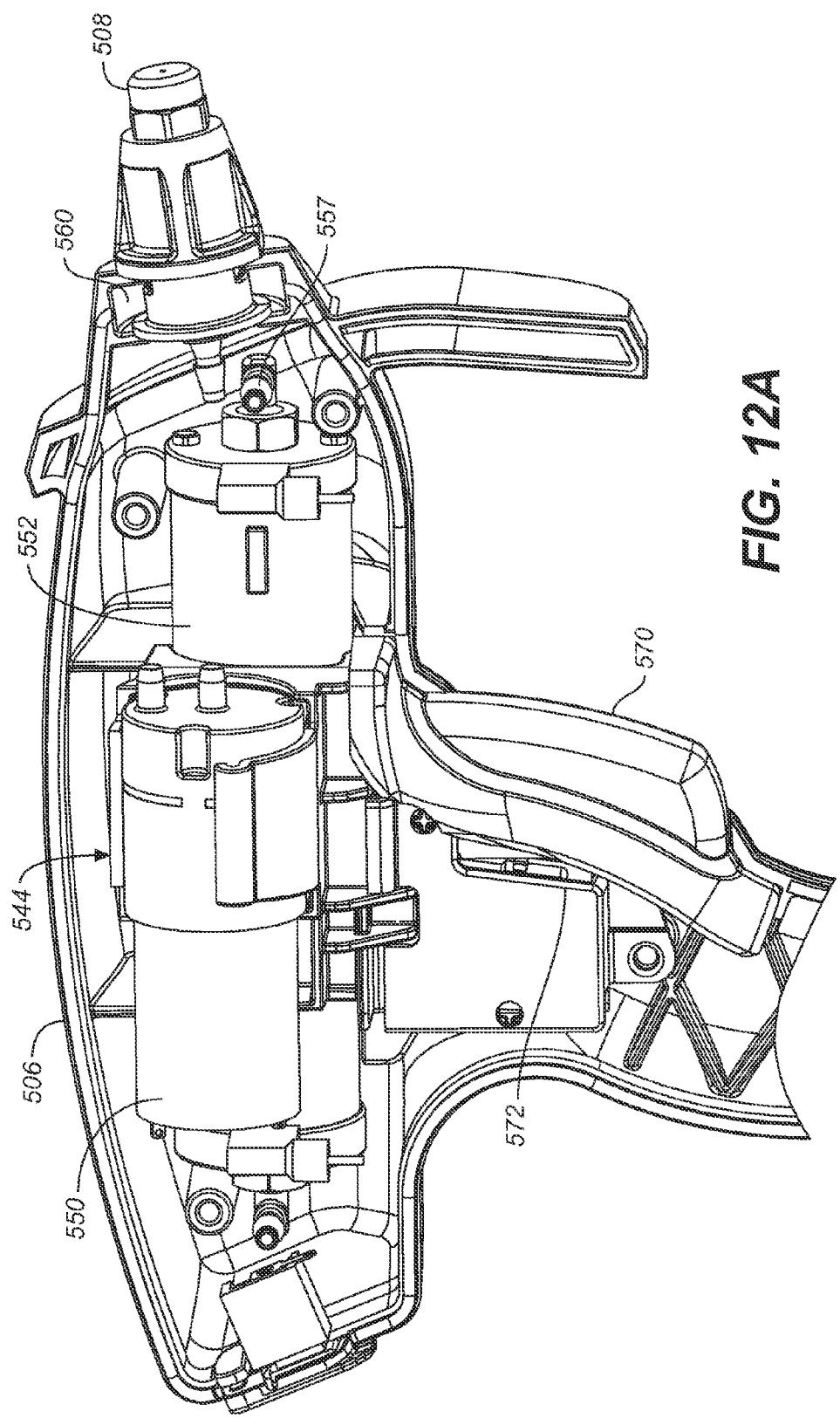

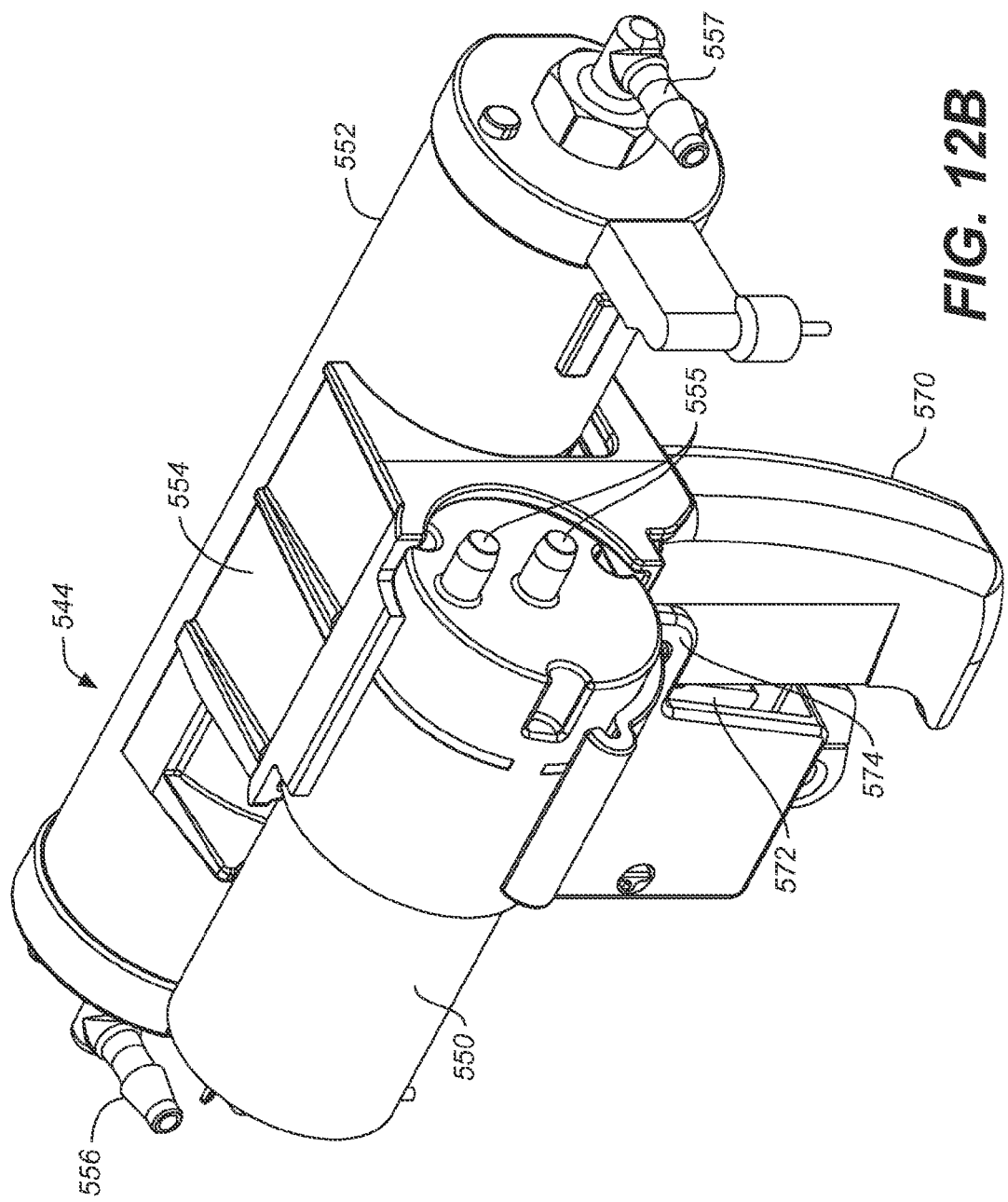

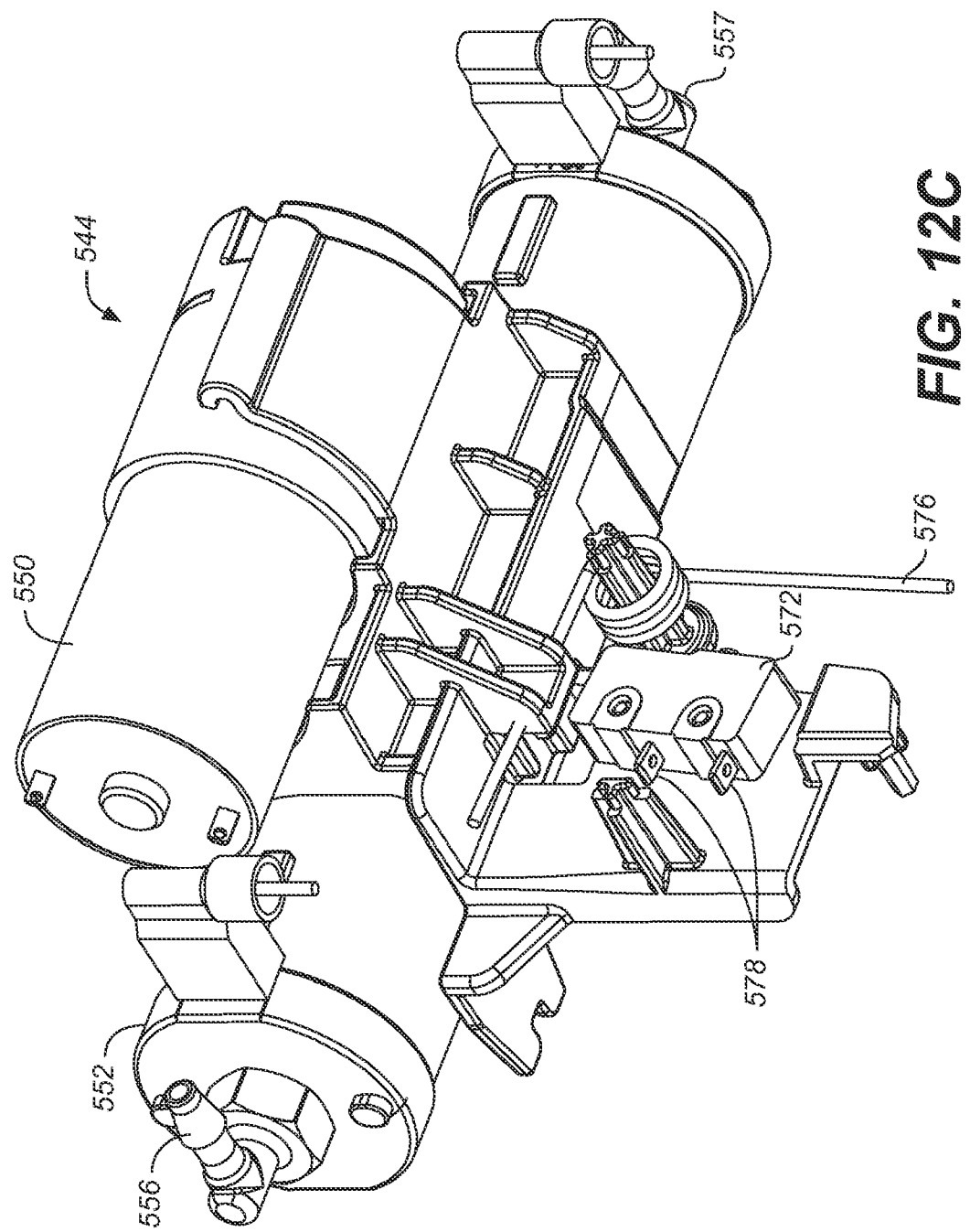

APPARATUS HAVING ELECTROLYSIS CELL AND INDICATOR LIGHT ILLUMINATING THROUGH LIQUID

CROSS-REFERENCE TO RELATED APPLICATIONS

The present application is based on and claims the benefit of the following applications:

1) U.S. Provisional patent application Ser. No. 61/092,586, filed Aug. 28, 2008, entitled APPARATUS HAVING ELECTROLYSIS CELL AND INDICATOR LIGHT ILLUMINATING THROUGH LIQUID;

the contents of which are hereby incorporated by reference in their entirety.

FIELD OF THE DISCLOSURE

The present disclosure relates to electrochemical activation of fluids and, more particularly, to electrolysis cells and corresponding methods.

BACKGROUND

Electrolysis cells are used in a variety of different applications for changing one or more characteristics of a fluid. For example, electrolysis cells have been used in cleaning/sanitizing applications, medical industries, and semiconductor manufacturing processes. Electrolysis cells have also been used in a variety of other applications and have had different configurations.

For cleaning/sanitizing applications, electrolysis cells are used to create anolyte electrochemically activated (EA) liquid and catholyte EA liquid. Anolyte EA liquids have known sanitizing properties, and catholyte EA liquids have known cleaning properties. Examples of cleaning and/or sanitizing systems are disclosed in Field et al. U.S. Publication No. 2007/0186368 A1, published Aug. 16, 2007.

SUMMARY

An aspect of the disclosure relates to an apparatus, which includes an electrolysis cell, a liquid flow path that passes through the electrolysis cell, and an indicator light. The indicator light is illuminated as a function of an operating characteristic of the electrolysis cell, and luminous flux radiated from the light illuminates liquid along at least a portion of the flow path.

Another aspect of the disclosure relates to a method. The method includes: carrying a liquid in a hand-held spray bottle; electrolyzing the liquid with an electrolysis cell carried by the bottle to produce electrolyzed liquid; dispensing the electrolyzed liquid; sensing an operating characteristic of the electrolysis cell; illuminating at least a portion of at least one of the liquid or the electrolyzed liquid as a function of the operating characteristic.

Another aspect of the disclosure relates to a hand-held spray bottle. The bottle includes a container, a nozzle, and a liquid flow path from the container to the nozzle. An electrolysis cell and a pump are coupled in the flow path. An indicator light is positioned to illuminate at least one of the container or the flow path.

In a specific example, the indicator light is illuminated as a function of an operating characteristic of the electrolysis cell. For example, the operating characteristic includes an electrical current drawn by the electrolysis cell.

In a specific example, the indicator light includes:

a first indicator light, which has a first color and which is illuminated when the electrical current is within a first current range and is off when the electrical current is outside the first current range; and a second indicator light, which has a second, different color and which is illuminated when the electrical current is outside the first current range and is off when the electrical current is within the first current range.

In a specific example, illumination of at least one of the container or the flow path is visible from a viewpoint that is external to the bottle.

For example, the indicator light is positioned such that luminous flux from the indicator light passes through liquid contained in at least one of the container or the flow path and is visible from a viewpoint that is external to the bottle.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIG. 12A illustrates a fragmentary, close-up view of a pump/cell assembly installed in a barrel of the housing.

FIG. 12B is a perspective view of the pump/cell assembly removed from the housing.

FIG. 12C is a bottom, perspective view of the pump/cell assembly with the trigger removed.

DETAILED DESCRIPTION OF ILLUSTRATIVE EMBODIMENTS

An aspect of the present disclosure is directed to a method and apparatus for electrolyzing liquids.

1. Hand-Held Spray Bottle

Electrolysis cells can be used in a variety of different applications and housed in a variety of different types of apparatus, which can be hand-held, mobile, immobile, wall-mounted, motorized or non-motorized cleaning/sanitizing vehicle, wheeled, etc, for example. In this example, an electrolysis cell is incorporated in a hand-held spray bottle.

Figure 1:
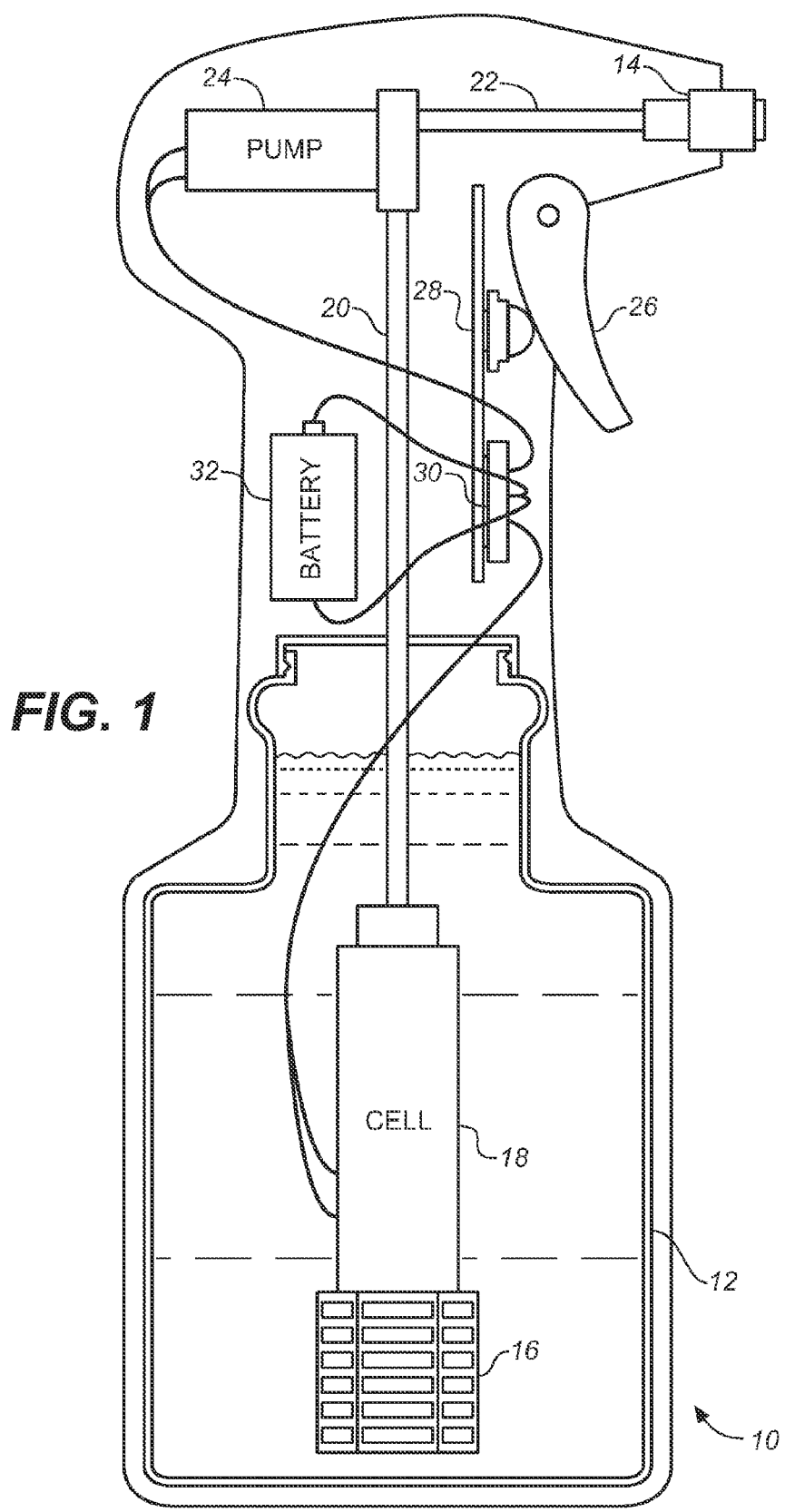
FIG. 1 is a simplified, schematic diagram of a hand-held spray bottle according to an exemplary aspect of the present disclosure.

FIG. 1 is a simplified, schematic diagram of a hand-held spray bottle 10 according to an exemplary aspect of the present disclosure. Spray bottle 10 includes a reservoir 12 for containing a liquid to be treated and then dispensed through a nozzle 14. In an example, the liquid to be treated includes an aqueous composition, such as regular tap water.

Spray bottle 10 further includes an inlet filter 16, one or more electrolysis cells 18, tubes 20 and 22, pump 24, actuator 26, switch 28, circuit board and control electronics 30 and batteries 32. Although not shown in FIG. 1, tubes 20 and 22 may be housed within a neck and barrel, respectively of bottle 10, for example. A cap 34 seals reservoir 12 around the neck of bottle 10. Batteries 32 can include disposable batteries and/or rechargeable batteries, for example, and provide electrical power to electrolysis cell 18 and pump 24 when energized by circuit board and control electronics 30.

In the example shown in FIG. 1, actuator 26 is a trigger-style actuator, which actuates momentary switch 28 between open and closed states. For example, when the user "squeezes" the hand trigger to a squeezed state, the trigger actuates the switch into the closed state. When the user releases the hand trigger, trigger actuates the switch into the open state. However, actuator 26 can have other styles in alternative embodiments and can be eliminated in further embodiments. In embodiments that lack a separate actuator, switch 28 can be actuated directly by the user. When switch 28 is in the open, non-conducting state, control electronics 30 de-energizes electrolysis cell 18 and pump 24. When switch 28 is in the closed, conducting state, control electronics 30 energizes electrolysis cell 18 and pump 24. Pump 24 draws liquid from reservoir 12 through filter 16, electrolysis cell 18, and tube 20 and forces the liquid out tube 22 and nozzle 14. Depending on the sprayer, nozzle 14 may or may not be adjustable, so as to select between squirting a stream, aerosolizing a mist, or dispensing a spray, for example.

Switch 28, itself, can have any suitable actuator type, such as a push-button switch as shown in FIG. 1, a toggle, a rocker, any mechanical linkage, and/or any non-mechanical sensor such as capacitive, resistive plastic, thermal, inductive, etc. Switch 28 can have any suitable contact arrangement, such such as momenary, single-pole single throw, etc.

In an alternative embodiment, pump 24 is replaced with a mechanical pump, such as a hand-triggered positive displacement pump, wherein actuator trigger 26 acts directly on the pump by mechanical action. In this embodiment, switch 28 could be separately actuated from the pump 24, such as a power switch, to energize electrolysis cell 18. In a further embodiment, batteries 32 are eliminated and power is delivered to spray bottle 10 from an external source, such as through a power cord, plug, and/or contact terminals.

The arrangement shown in FIG. 1 is provided merely as a non-limiting example. Spray bottle 10 can have any other structural and/or functional arrangement. For example, pump 24 can be located downstream of cell 18, as shown in FIG. 1, or upstream of cell 18 with respect to the direction of fluid flow from reservoir 12 to nozzle 14.

As described in more detail below, the spray bottle contains a liquid to be sprayed on a surface to be cleaned and/or sanitized. In one non-limiting example, electrolysis cell 18 converts the liquid to an anolyte EA liquid and a catholyte EA liquid prior to being dispensed from the bottle as an output spray. The anolyte and catholyte EA liquids can be dispensed as a combined mixture or as separate spray outputs, such as through separate tubes and/or nozzles. In the embodiment shown in FIG. 1, the anolyte and catholyte EA liquids are dispensed as a combined mixture. With a small and intermittent output flow rate provided the spray bottle, electrolysis cell 18 can have a small package and be powered by batteries carried by the package or spray bottle, for example.

2. Electrolysis Cells

An electrolysis cell includes any fluid treatment cell that is adapted to apply an electric field across the fluid between at least one anode electrode and at least one cathode electrode. An electrolysis cell can have any suitable number of electrodes, any suitable number of chambers for containing the fluid, and any suitable number of fluid inputs and fluid outputs. The cell can be adapted to treat any fluid (such as a liquid or gas-liquid combination). The cell can include one or more ion-selective membranes between the anode and cathode or can be configured without any ion selective membranes. An electrolysis cell having an ion-selective membrane is referred to herein as a "functional generator".

Electrolysis cells can be used in a variety of different applications and can have a variety of different structures, such as but not limited to a spray bottle as discussed with reference to FIG. 1, and/or the structures disclosed in Field et al. U.S. Patent Publication No. 2007/0186368, published Aug. 16, 2007. Thus, although various elements and processes relating to electrolysis are described herein relative to the context of a spray bottle, these elements and processes can be applied to, and incorporated in, other, non-spray bottle applications.

3. Electrolysis Cell having a Membrane 3.1 Cell Structure

Figure 2:
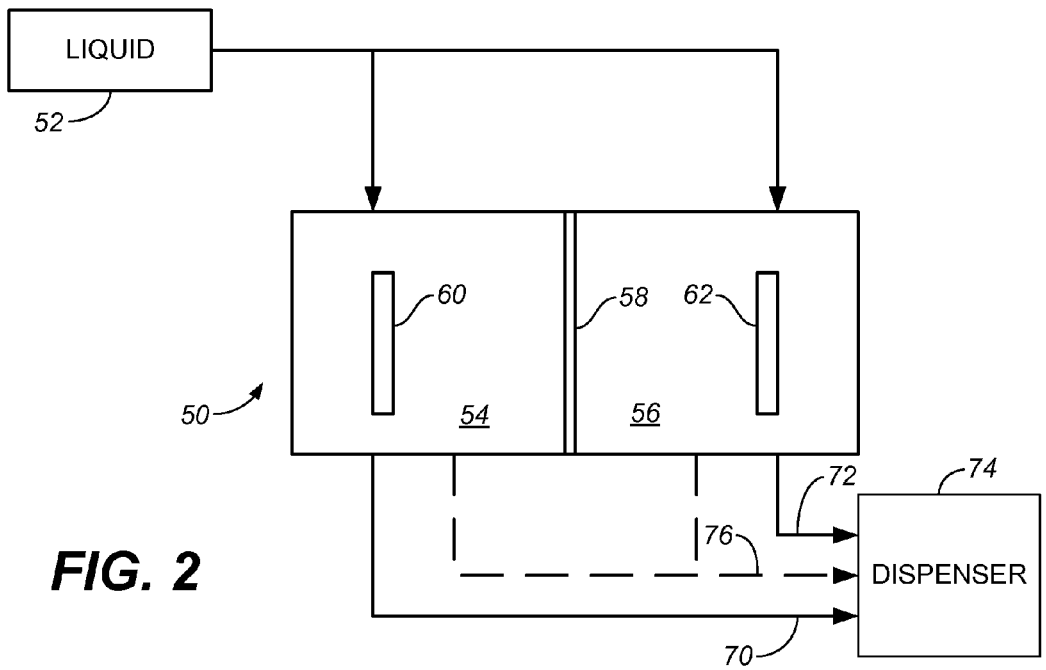
FIG. 2 illustrates an example of an electrolysis cell having an ion-selective membrane.

FIG. 2 is a schematic diagram illustrating an example of an electrolysis cell 50 that can be used in the spray bottle shown in FIG. 1, for example. Electrolysis cell 50 and which receives liquid to be treated from a liquid source 52. Liquid source 52 can include a tank or other solution reservoir, such as reservoir 12 in FIG. 1, or can include a fitting or other inlet for receiving a liquid from an external source.

Cell 50 has one or more anode chambers 54 and one or more cathode chambers 56 (known as reaction chambers), which are separated by an ion exchange membrane 58, such as a cation or anion exchange membrane. One or more anode electrodes 60 and cathode electrodes 62 (one of each electrode shown) are disposed in each anode chamber 54 and each cathode chamber 56, respectively. The anode and cathode electrodes 60, 62 can be made from any suitable material, such as a conductive polymer, titanium and/or titanium coated with a precious metal, such as platinum, or any other suitable electrode material. In one example, at least one of the anode or cathode is at least partially or wholly made from a conductive polymer. The electrodes and respective chambers can have any suitable shape and construction. For example, the electrodes can be flat plates, coaxial plates, rods, or a combination thereof. Each electrode can have, for example, a solid construction or can have one or more apertures. In one example, each electrode is formed as a mesh. In addition, multiple cells 50 can be coupled in series or in parallel with one another, for example.

The electrodes 60, 62 are electrically connected to opposite terminals of a conventional power supply (not shown). Ion exchange membrane 58 is located between electrodes 60 and 62. The power supply can provide a constant DC output voltage, a pulsed or otherwise modulated DC output voltage, and/or a pulsed or otherwise modulated AC output voltage to the anode and cathode electrodes. The power supply can have any suitable output voltage level, current level, duty cycle or waveform.

For example in one embodiment, the power supply applies the voltage supplied to the plates at a relative steady state. The power supply (and/or control electronics) includes a DC/DC converter that uses a pulse-width modulation (PWM) control scheme to control voltage and current output. Other types of power supplies can also be used, which can be pulsed or not pulsed and at other voltage and power ranges. The parameters are application-specific.

During operation, feed water (or other liquid to be treated) is supplied from source 52 to both anode chamber 54 and cathode chamber 56. In the case of a cation exchange membrane, upon application of a DC voltage potential across anode 60 and cathode 62, such as a voltage in a range of about 5 Volts (V) to about 28V, cations originally present in the anode chamber 54 move across the ion-exchange membrane 58 towards cathode 62 while anions in anode chamber 54 move towards anode 60. However, anions present in cathode chamber 56 are not able to pass through the cation-exchange membrane, and therefore remain confined within cathode chamber 56.

As a result, cell 50 electrochemically activates the feed water by at least partially utilizing electrolysis and produces electrochemically-activated water in the form of an acidic anolyte composition 70 and a basic catholyte composition 72.

If desired, the anolyte and catholyte can be generated in different ratios to one another through modifications to the structure of the electrolysis cell, for example. For example, the cell can be configured to produce a greater volume of catholyte than anolyte if the primary function of the EA water is cleaning. Alternatively, for example, the cell can be configured to produce a greater volume of anolyte than catholyte if the primary function of the EA water is sanitizing. Also, the concentrations of reactive species in each can be varied.

For example, the cell can have a 3:2 ratio of cathode plates to anode plates for producing a greater volume of catholyte than anolyte. Each cathode plate is separated from a respective anode plate by a respective ion exchange membrane. Thus, there are three cathode chambers for two anode chambers. This configuration produces roughly 60% catholyte to 40% anolyte. Other ratios can also be used.

3.2 Example Reactions

In addition, water molecules in contact with anode 60 are electrochemically oxidized to oxygen ($O_2$) and hydrogen ions ($H^+$) in the anode chamber 54 while water molecules in contact with the cathode 62 are electrochemically reduced to hydrogen gas ($H_2$) and hydroxyl ions ($OH^-$) in the cathode chamber 56. The hydrogen ions in the anode chamber 54 are allowed to pass through the cation-exchange membrane 58 into the cathode chamber 56 where the hydrogen ions are reduced to hydrogen gas while the oxygen gas in the anode chamber 54 oxygenates the feed water to form the anolyte 70. Furthermore, since regular tap water typically includes sodium chloride and/or other chlorides, the anode 60 oxidizes the chlorides present to form chlorine gas. As a result, a substantial amount of chlorine is produced and the pH of the anolyte composition 70 becomes increasingly acidic over time.

As noted, water molecules in contact with the cathode 62 are electrochemically reduced to hydrogen gas and hydroxyl ions ($OH^-$) while cations in the anode chamber 54 pass through the cation-exchange membrane 58 into the cathode chamber 56 when the voltage potential is applied. These cations are available to ionically associate with the hydroxyl ions produced at the cathode 62, while hydrogen gas bubbles form in the liquid. A substantial amount of hydroxyl ions accumulates over time in the cathode chamber 56 and reacts with cations to form basic hydroxides. In addition, the hydroxides remain confined to the cathode chamber 56 since the cation-exchange membrane does not allow the negatively charged hydroxyl ions pass through the cation-exchange membrane. Consequently, a substantial amount of hydroxides is produced in the cathode chamber 56, and the pH of the catholyte composition 72 becomes increasingly alkaline over time.

The electrolysis process in the functional generator 50 allow concentration of reactive species and the formation of metastable ions and radicals in the anode chamber 54 and cathode chamber 56.

The electrochemical activation process typically occurs by either electron withdrawal (at anode 60) or electron introduction (at cathode 62), which leads to alteration of physiochemical (including structural, energetic and catalytic) properties of the feed water. It is believed that the feed water (anolyte or catholyte) gets activated in the immediate proximity of the electrode surface where the electric field intensity can reach a very high level. This area can be referred to as an electric double layer (EDL).

While the electrochemical activation process continues, the water dipoles generally align with the field, and a proportion of the hydrogen bonds of the water molecules consequentially break. Furthermore, singly-linked hydrogen atoms bind to the metal atoms (e.g., platinum atoms) at cathode electrode 62, and single-linked oxygen atoms bind to the metal atoms (e.g., platinum atoms) at the anode electrode 60. These bound atoms diffuse around in two dimensions on the surfaces of the respective electrodes until they take part in further reactions. Other atoms and polyatomic groups may also bind similarly to the surfaces of anode electrode 60 and cathode electrode 62, and may also subsequently undergo reactions. Molecules such as oxygen ($O_2$) and hydrogen ($H_2$) produced at the surfaces may enter small cavities in the liquid phase of the water (i.e., bubbles) as gases and/or may become solvated by the liquid phase of the water. These gas-phase bubbles are thereby dispersed or otherwise suspended throughout the liquid phase of the feed water.

The sizes of the gas-phase bubbles may vary depending on a variety of factors, such as the pressure applied to the feed water, the composition of the salts and other compounds in the feed water, and the extent of the electrochemical activation. Accordingly, the gas-phase bubbles may have a variety of different sizes, including, but not limited to macrobubbles, microbubbles, nanobubbles, and mixtures thereof. In embodiments including macrobubbles, examples of suitable average bubble diameters for the generated bubbles include diameters ranging from about 500 micrometers to about one millimeter. In embodiments including microbubbles, examples of suitable average bubble diameters for the generated bubbles include diameters ranging from about one micrometer to less than about 500 micrometers. In embodiments including nanobubbles, examples of suitable average bubble diameters for the generated bubbles include diameters less than about one micrometer, with particularly suitable average bubble diameters including diameters less than about 500 nanometers, and with even more particularly suitable average bubble diameters including diameters less than about 100 nanometers.

Surface tension at a gas-liquid interface is produced by the attraction between the molecules being directed away from the surfaces of anode electrode 60 and cathode electrode 62 as the surface molecules are more attracted to the molecules within the water than they are to molecules of the gas at the electrode surfaces. In contrast, molecules of the bulk of the water are equally attracted in all directions. Thus, in order to increase the possible interaction energy, surface tension causes the molecules at the electrode surfaces to enter the bulk of the liquid.

In the embodiments in which gas-phase nanobubbles are generated, the gas contained in the nanobubbles (i.e., bubbles having diameters of less than about one micrometer) are also believed to be stable for substantial durations in the feed water, despite their small diameters. While not wishing to be bound by theory, it is believed that the surface tension of the water, at the gas/liquid interface, drops when curved surfaces of the gas bubbles approach molecular dimensions. This reduces the natural tendency of the nanobubbles to dissipate.

Furthermore, nanobubble gas/liquid interface is charged due to the voltage potential applied across membrane 58. The charge introduces an opposing force to the surface tension, which also slows or prevents the dissipation of the nanobubbles. The presence of like charges at the interface reduces the apparent surface tension, with charge repulsion acting in the opposite direction to surface minimization due to surface tension. Any effect may be increased by the presence of additional charged materials that favor the gas/liquid interface.

The natural state of the gas/liquid interfaces appears to be negative. Other ions with low surface charge density and/or high polarizability (such as $Cl^-$, $ClO^-$, $HO_2^-$, and $O_0^-$) also favor the gas/liquid interfaces, as do hydrated electrons. Aqueous radicals also prefer to reside at such interfaces. Thus, it is believed that the nanobubbles present in the catholyte (i.e., the water flowing through cathode chamber 56) are negatively charged, but those in the anolyte (i.e., the water flowing through anode chamber 54) will possess little charge (the excess cations cancelling out the natural negative charge). Accordingly, catholyte nanobubbles are not likely to lose their charge on mixing with the anolyte.

Additionally, gas molecules may become charged within the nanobubbles (such as $O_2^-$), due to the excess potential on the cathode, thereby increasing the overall charge of the nanobubbles. The surface tension at the gas/liquid interface of charged nanobubbles can be reduced relative to uncharged nanobubbles, and their sizes stabilized. This can be qualitatively appreciated as surface tension causes surfaces to be minimized, whereas charged surfaces tend to expand to minimize repulsions between similar charges. Raised temperature at the electrode surface, due to the excess power loss over that required for the electrolysis, may also increase nanobubble formation by reducing local gas solubility.

As the repulsion force between like charges increases inversely as the square of their distances apart, there is an increasing outwards pressure as a bubble diameter decreases. The effect of the charges is to reduce the effect of the surface tension, and the surface tension tends to reduce the surface whereas the surface charge tends to expand it. Thus, equilibrium is reached when these opposing forces are equal. For example, assuming the surface charge density on the inner surface of a gas bubble (radius r) is $\phi(e^-/meter^2)$, the outwards pressure ("$P_{out}$"), can be found by solving the NavierStokes equations to give:

$$P_{out} = \phi^2/2D\epsilon_0 \quad (Equation\ 1)$$

where D is the relative dielectric constant of the gas bubble (assumed unity), "$\epsilon_0$" is the permittivity of a vacuum (i.e., 8.854 pF/meter). The inwards pressure ("$P_{in}$") due to the surface tension on the gas is:

$$P_{in} = 2\ g/r\ P_{out} \quad (Equation\ 2)$$

where "g" is the surface tension (0.07198 Joules/meter² at 25° C.). Therefore if these pressures are equal, the radius of the gas bubble is:

$$r = 0.28792\ \epsilon_0/\phi^2. \quad (Equation\ 3)$$

Accordingly, for nanobubble diameters of 5 nanometers, 10 nanometers, 20 nanometers, 50 nanometers, and 100 nanometers the calculated charge density for zero excess internal pressure is 0.20, 0.14, 0.10, 0.06 and 0.04 $e^-$/nanometer² bubble surface area, respectively. Such charge densities are readily achievable with the use of an electrolysis cell (e.g., electrolysis cell 18). The nanobubble radius increases as the total charge on the bubble increases to the power ⅔. Under these circumstances at equilibrium, the effective surface tension of the fuel at the nanobubble surface is zero, and the presence of charged gas in the bubble increases the size of the stable nanobubble. Further reduction in the bubble size would not be indicated as it would cause the reduction of the internal pressure to fall below atmospheric pressure.

In various situations within the electrolysis cell (e.g., electrolysis cell 18), the nanobubbles may divide into even smaller bubbles due to the surface charges. For example, assuming that a bubble of radius "r" and total charge "q" divides into two bubbles of shared volume and charge (radius $r_{1/2} = r/2^{1/3}$, and charge $q_{1/2} = q/2$), and ignoring the Coulomb interaction between the bubbles, calculation of the change in energy due to surface tension ($\Delta E_{ST}$) and surface charge ($\Delta E_q$) gives:

$$\Delta E_{ST} = +2(4\pi\gamma r_{1/2}^2) - 4\pi\gamma r^2 = 4\pi\gamma r^2(2^{1/3} - 1) \quad \text{(Equation 3)}$$

and $$\Delta E_q = -2\left(\frac{1}{2} \times \frac{(q/2)^2}{4\pi\varepsilon_0 r_{1/2}}\right) - \frac{1}{2} \times \frac{q^2}{4\pi\varepsilon_0 r} = \frac{q^2}{8\pi\varepsilon_0 r}(1 - 2^{-2/3}) \quad \text{(Equation 4)}$$

The bubble is metastable if the overall energy change is negative which occurs when $\Delta E_{ST}+\Delta E_q$ is negative, thereby providing:

$$\frac{q^2}{8\pi\varepsilon_0 r}(1 - 2^{-2/3}) + 4\pi\gamma r^2(2^{1/3} - 1) \leq 0 \quad \text{(Equation 5)}$$

which provides the relationship between the radius and the charge density ($\phi$):

$$\phi = \frac{q}{4\pi r^2} \geq \sqrt{\left(\frac{2\gamma\varepsilon_0}{r}\frac{(2^{1/3}-1)}{(1-2^{-2/3})}\right)} \quad \text{(Equation 6)}$$

Accordingly, for nanobubble diameters of 5 nanometers, 10 nanometers, 20 nanometers, 50 nanometers, and 100 nanometers the calculated charge density for bubble splitting 0.12, 0.08, 0.06, 0.04 and 0.03 $e^-$/nanometer$^2$ bubble surface area, respectively. For the same surface charge density, the bubble diameter is typically about three times larger for reducing the apparent surface tension to zero than for splitting the bubble in two. Thus, the nanobubbles will generally not divide unless there is a further energy input.

The above-discussed gas-phase nanobubbles are adapted to attach to dirt particles, thereby transferring their ionic charges. The nanobubbles stick to hydrophobic surfaces, which are typically found on typical dirt particles, which releases water molecules from the high energy water/hydrophobic surface interface with a favorable negative free energy change. Additionally, the nanobubbles spread out and flatten on contact with the hydrophobic surface, thereby reducing the curvatures of the nanobubbles with consequential lowering of the internal pressure caused by the surface tension. This provides additional favorable free energy release. The charged and coated dirt particles are then more easily separated one from another due to repulsion between similar charges, and the dirt particles enter the solution as colloidal particles.

Furthermore, the presence of nanobubbles on the surface of particles increases the pickup of the particle by micron-sized gas-phase bubbles, which may also be generated during the electrochemical activation process. The presence of surface nanobubbles also reduces the size of the dirt particle that can be picked up by this action. Such pickup assist in the removal of the dirt particles from floor surfaces and prevents re-deposition. Moreover, due to the large gas/liquid surface area-to-volume ratios that are attained with gas-phase nanobubbles, water molecules located at this interface are held by fewer hydrogen bonds, as recognized by water's high surface tension. Due to this reduction in hydrogen bonding to other water molecules, this interface water is more reactive than normal water and will hydrogen bond to other molecules more rapidly, thereby showing faster hydration.

For example, at 100% efficiency a current of one ampere is sufficient to produce 0.5/96,485.3 moles of hydrogen ($H_2$) per second, which equates to 5.18 micromoles of hydrogen per second, which correspondingly equates to 5.18×22.429 microliters of gas-phase hydrogen per second at a temperature of 0° C. and a pressure of one atmosphere. This also equates to 125 microliters of gas-phase hydrogen per second at a temperature of 20° C. and a pressure of one atmosphere. As the partial pressure of hydrogen in the atmosphere is effectively zero, the equilibrium solubility of hydrogen in the electrolyzed solution is also effectively zero and the hydrogen is held in gas cavities (e.g., macrobubbles, microbubbles, and/or nanobubbles).

Assuming the flow rate of the electrolyzed solution is 0.12 U.S. gallons per minute, there is 7.571 milliliters of water flowing through the electrolysis cell each second. Therefore, there are 0.125/7.571 liters of gas-phase hydrogen within the bubbles contained in each liter of electrolyzed solution at a temperature of 20° C. and a pressure of one atmosphere. This equates to 0.0165 liters of gas-phase hydrogen per liter of solution less any of gas-phase hydrogen that escapes from the liquid surface and any that dissolves to supersaturate the solution.

The volume of a 10 nanometer-diameter nanobubble is $5.24\times10^{-22}$ liters, which, on binding to a hydrophobic surface covers about $1.25\times10^{-16}$ square meters. Thus, in each liter of solution there would be a maximum of about $3\times10^{-19}$ bubbles (at 20° C. and one atmosphere) with combined surface covering potential of about 4000 square meters. Assuming a surface layer just one molecule thick, this provides a concentration of active surface water molecules of over 50 millimoles. While this concentration represents a maximum amount, even if the nanobubbles have greater volume and greater internal pressure, the potential for surface covering remains large. Furthermore, only a small percentage of the dirt particles surfaces need to be covered by the nanobubbles for the nanobubbles to have a cleaning effect.

Accordingly, the gas-phase nanobubbles, generated during the electrochemical activation process, are beneficial for attaching to dirt particles so transferring their charge. The resulting charged and coated dirt particles are more readily separated one from another due to the repulsion between their similar charges. They will enter the solution to form a colloidal suspension. Furthermore, the charges at the gas/water interfaces oppose the surface tension, thereby reducing its effect and the consequent contact angles. Also, the nanobubbles coating of the dirt particles promotes the pickup of larger buoyant gas-phase macrobubbles and microbubbles that are introduced. In addition, the large surface area of the nanobubbles provides significant amounts of higher reactive water, which is capable of the more rapid hydration of suitable molecules.

4. Ion Exchange Membrane

As mentioned above, the ion exchange membrane 58 can include a cation exchange membrane (i.e., a proton exchange membrane) or an anion exchange membrane. Suitable cation exchange membranes for membrane 38 include partially and fully fluorinated ionomers, polyaromatic ionomers, and combinations thereof. Examples of suitable commercially available ionomers for membrane 38 include sulfonated tetrafluorethylene copolymers available under the trademark "NAFION" from E.I. du Pont de Nemours and Company, Wilmington, Del.; perfluorinated carboxylic acid ionomers available under the trademark "FLEMION" from Asahi Glass Co., Ltd., Japan; perfluorinated sulfonic acid ionomers available under the trademark "ACIPLEX" Aciplex from Asahi Chemical Industries Co. Ltd., Japan; and combinations thereof. However, any ion exchange membrane can be used in other examples.

5. Dispenser

The anolyte and catholyte EA liquid outputs can be coupled to a dispenser 74, which can include any type of dispenser or dispensers, such as an outlet, fitting, spigot, spray head, a cleaning/sanitizing tool or head, etc. In the example shown in FIG. 1, dispenser 34 includes spray nozzle 14. There can be a dispenser for each output 70 and 72 or a combined dispenser for both outputs.

In one example, the anolyte and catholyte outputs are blended into a common output stream 76, which is supplied to dispenser 74. As described in Field et al. U.S. Patent Publication No. 2007/0186368, it has been found that the anolyte and catholyte can be blended together within the distribution system of a cleaning apparatus and/or on the surface or item being cleaned while at least temporarily retaining beneficial cleaning and/or sanitizing properties. Although the anolyte and catholyte are blended, they are initially not in equilibrium and therefore temporarily retain their enhanced cleaning and/or sanitizing properties.

For example, in one embodiment, the catholyte EA water and the anolyte EA water maintain their distinct electrochemically activated properties for at least 30 seconds, for example, even though the two liquids are blended together. During this time, the distinct electrochemically activated properties of the two types of liquids do not neutralize immediately. This allows the advantageous properties of each liquid to be utilized during a common cleaning operation. After a relatively short period of time, the blended anolyte and catholyte EA liquid on the surface being cleaned quickly neutralize substantially to the original pH and ORP of the source liquid (e.g., those of normal tap water). In one example, the blended anolyte and catholyte EA liquid neutralize substantially to a pH between pH6 and pH8 and an ORP between ±50 mV within a time window of less than 1 minute from the time the anolyte and catholyte EA outputs are produced by the electrolysis cell. Thereafter, the recovered liquid can be disposed in any suitable manner.

However, in other embodiments, the blended anolyte and catholyte EA liquid can maintain pHs outside of the range between pH6 and pH8 and ORPs outside the range of ±50 mV for a time greater than 30 seconds, and/or can neutralize after a time range that is outside of 1 minute, depending on the properties of the liquid.

6. Electrolysis Cell with No Ion-Selective Membrane

Figure 3:
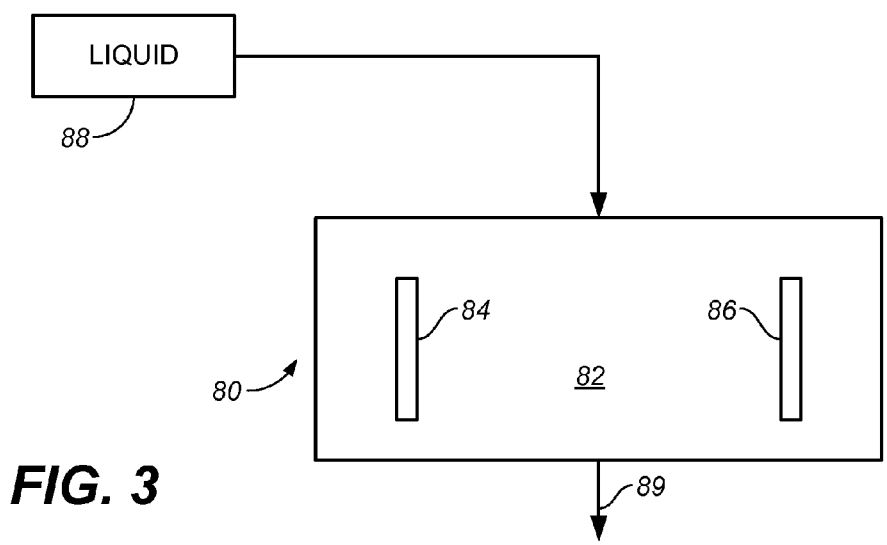
FIG. 3 illustrates an electrolysis cell having no ion-selective membrane according to a further example of the disclosure.

FIG. 3 illustrates an electrolysis cell 80 having no ion-selective membrane according to a further example of the disclosure. Cell 80 includes a reaction chamber 82, an anode 84 and a cathode 86. Chamber 82 can be defined by the walls of cell 80, by the walls of a container or conduit in which electrodes 84 and 86 are placed, or by the electrodes themselves, for example. Anode 84 and cathode 86 may be made from any suitable material or a combination of materials, such as a conductive polymer, titanium and/or titanium coated with a precious metal, such as platinum. Anode 84 and cathode 86 are connected to a conventional electrical power supply, such as batteries 32 shown in FIG. 1. In one embodiment, electrolytic cell 80 includes its own container that defines chamber 82 and is located in the flow path of the liquid to be treated, such as within the flow path of a hand-held spray bottle or mobile floor cleaning apparatus.

During operation, liquid is supplied by a source 88 and introduced into reaction chamber 82 of electrolysis cell 80. In the embodiment shown in FIG. 3, electrolysis cell 80 does not include an ion exchange membrane that separates reaction products at anode 84 from reaction products at cathode 86. In the example in which tap water is used as the liquid to be treated for use in cleaning, after introducing the water into chamber 82 and applying a voltage potential between anode 84 and cathode 86, water molecules in contact with or near anode 84 are electrochemically oxidized to oxygen ($O_2$) and hydrogen ions ($H^+$) while water molecules in contact or near cathode 86 are electrochemically reduced to hydrogen gas ($H_2$) and hydroxyl ions ($OH^-$). Other reactions can also occur and the particular reactions depend on the components of the liquid. The reaction products from both electrodes are able to mix and form an oxygenated fluid 89 (for example) since there is no physical barrier, for example, separating the reaction products from each other. Alternatively, for example, anode 84 can be separated from cathode 84 by using a dielectric barrier such as a non-permeable membrane (not shown) disposed between the anode and cathode.

7. Electrode Pattern Examples

As mentioned above, at least one of the anode or cathode electrodes can be formed at least partially or wholly of a conductive polymer, such as those used for static dissipating devices. Examples of suitable conductive polymers are commercially available from RTP Company of Winona, Minn., USA. For example, the electrodes can be formed of a conductive plastic compound having a surface resistivity of $10^0$ to $10^{12}$ ohm/sq, such as $10^1$ to $10^6$ ohm/sq. However, electrodes having surface resistivities outside those ranges can be used in other examples.

With conductive polymer, the electrodes can be easily molded or otherwise formed in any desired shape. For example, the electrodes can be injection molded. As mentioned above, one or more of the electrodes can form a mesh, with regular-sized rectangular openings in the form of a grid. However, the openings or apertures can have any shape, such as circular, triangular, curvilinear, rectilinear, regular and/or irregular. Curvilinear apertures have at least one curved edge. When injection molded, for example, the shapes and sizes of the apertures can be easily tailored to a particular pattern. However, these patterns can also be formed in metallic electrodes in other examples of the present disclosure.

The apertures can be sized and positioned to increase the surface area of the electrode for electrolysis and thereby promote generation of gas bubbles in the liquid being treated.

Figure 4A:
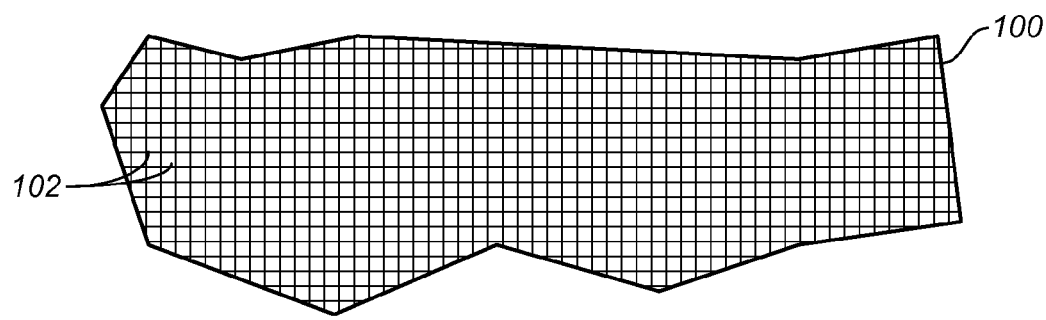
FIG. 4A is a fragmentary view of a conductive polymer electrode having a plurality of rectilinear apertures in a regular grid pattern according to an aspect of the disclosure.

FIG. 4A is a fragmentary view of a conductive polymer electrode 100 having a plurality of rectilinear (e.g., rectangular) apertures 102 in a regular grid pattern according to an aspect of the disclosure.

Figure 4B:
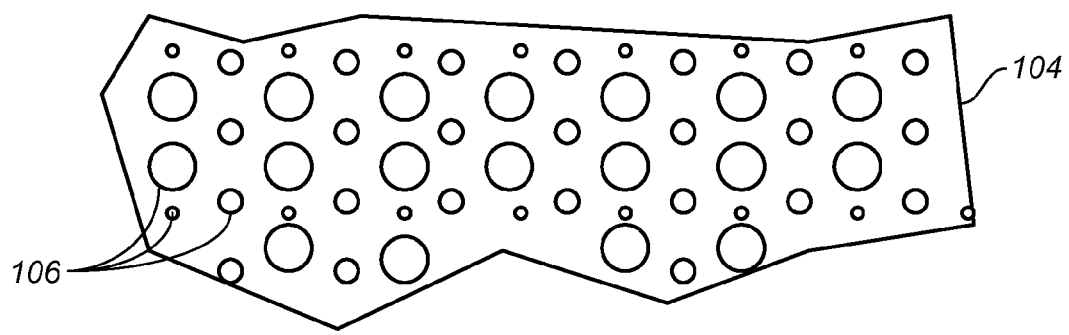
FIG. 4B is a fragmentary view of a conductive polymer electrode having a plurality of curvilinear apertures of different sizes in a regular grid pattern according to another example.

FIG. 4B is a fragmentary view of a conductive polymer electrode 104 having a plurality of curvilinear (e.g., circular) apertures 106 of different sizes in a regular grid pattern according to another example. The use of differently sized apertures in the same electrode may promote generation of differently sized gas bubbles along the edges of the apertures during electrolysis.

Figure 4C:
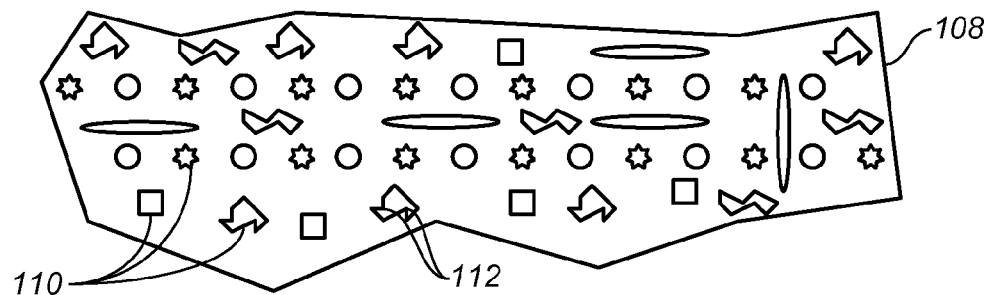
FIG. 4C is a fragmentary view of a conductive polymer electrode having a plurality of irregular and regular shaped apertures having a variety of different shapes and sizes according to another example.

FIG. 4C is a fragmentary view of a conductive polymer electrode 108 having a plurality of irregular and regular shaped apertures 110 having a variety of different shapes and sizes according to another example. In this example, various apertures 110 define various opening areas. One or more of the apertures 110 can include one or more internal points, such as points 112, that are believed to promote further gas bubble and reactive species generation during electrolysis. These apertures form polygons having at least one internal angle (e.g., at point 112) that is greater than 180 degrees. In an alternative embodiment, the apertures have a plurality of internal angles greater than 180 degrees.

In addition, the electrodes can be formed with one or more other non-uniform features, such as spikes or burs that further increase the electrode surface area. The spikes can be arranged in a regular pattern or an irregular pattern and can have the same sizes and shapes or can have different sizes and/or shapes.

For example, an electrolysis cell can be constructed to include an anode and a cathode, wherein at least one of the anode electrode or the cathode electrode comprises a first plurality of apertures having a first size (and/or shape) and a second plurality of apertures having a second, different size (and/or shape). In one example, the electrolysis cell also includes an ion selective membrane disposed between the anode electrode and the cathode electrode and which defines a respective anode chamber and cathode chamber.

In a further example, at least two apertures of a set comprising the first and second plurality of apertures have different shapes (and/or sizes) than one another. In a further example, at least three apertures of a set comprising the first and second plurality of apertures have different shapes (and/or sizes) than one another.

The first and second plurality of apertures can have polygon shapes and/or curvilinear shapes formed of at least one curved edge. At least one of the first plurality or the second plurality of apertures can be arranged in a regular pattern or in an irregular pattern.

At least one aperture of the first plurality or the second plurality of apertures can have a polygon shape with at least one internal angle that is greater than 180 degrees.

In a further example, the electrodes shown in FIGS. 4A-4C are fabricated of a conductive metallic material. For example as shown in FIG. 4A, the electrode 100 can be formed of a metallic mesh, which can be plated with another material such as platinum or can be unplated.

8. Tubular Electrode Example

Figure 5:
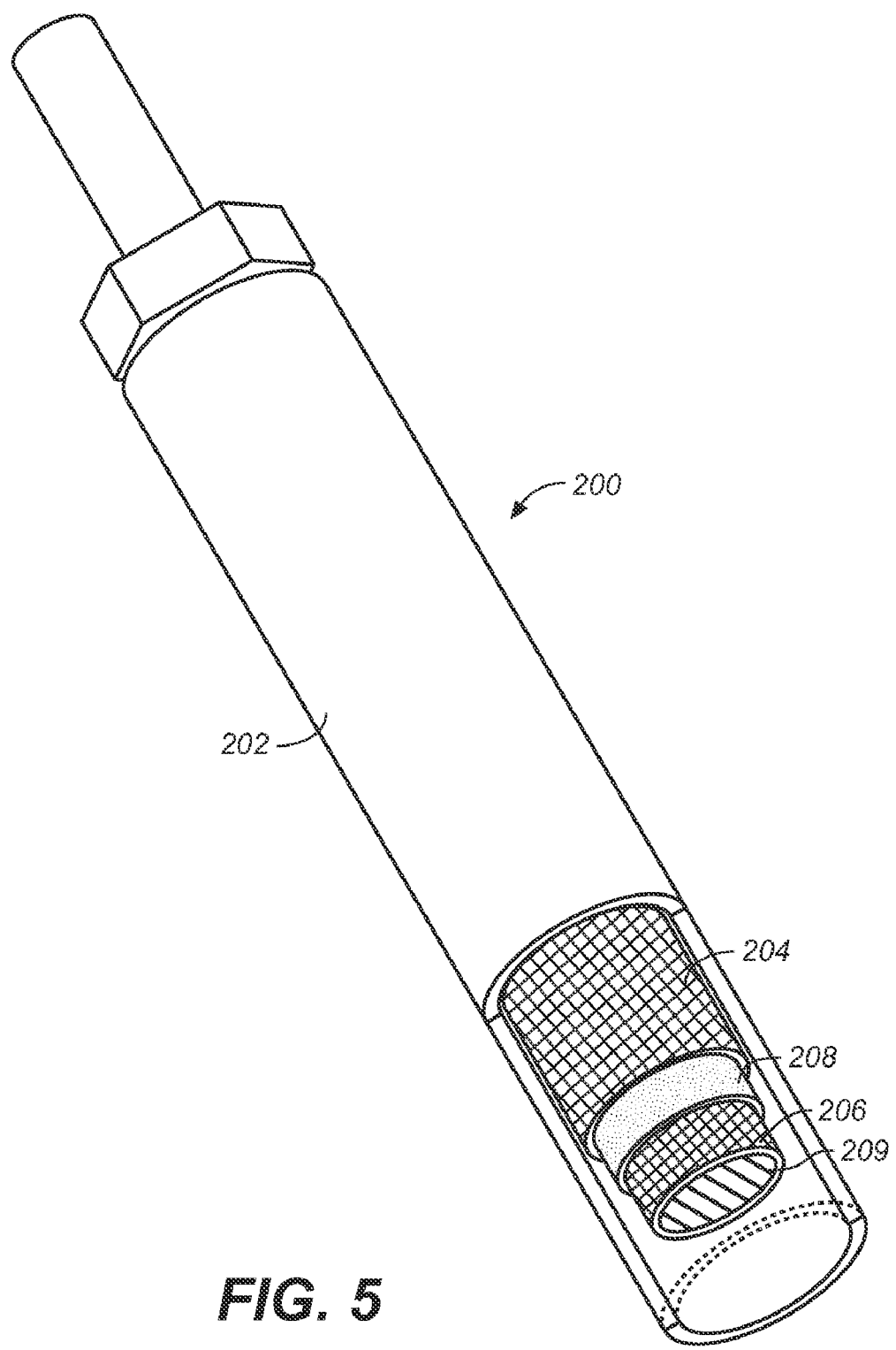
FIG. 5 illustrates an example of an electrolysis cell having a tubular shape according to one illustrative example.

The electrodes themselves can have any suitable shape, such as planar, coaxial plates, cylindrical rods, or a combination thereof. FIG. 5 illustrates an example of an electrolysis cell 200 having a tubular shape according to one illustrative example. Portions of cell 200 are cut away for illustration purposes. In this example, cell 200 is an electrolysis cell having a tubular housing 202, a tubular outer electrode 204, and a tubular inner electrode 206, which is separated from the outer electrode by a suitable gap, such as 0.040 inches. Other gap sizes can also be used, such as but not limited to gaps in the range of 0.020 inches to 0.080 inches. Either of the inner or outer electrode can serve as the anode/cathode, depending upon the relative polarities of the applied voltages.

In one example, outer electrode 204 and inner electrode 206 have conductive polymer constructions with apertures such as those shown in FIGS. 4A-4C, for example. However, one or both electrodes can have a solid construction in another example.

The electrodes 206 and 206 can be made from any suitable material, such as a conductive polymer, titanium and/or titanium coated with a precious metal, such as platinum, or any other suitable electrode material. In addition, multiple cells 200 can be coupled in series or in parallel with one another, for example.

In a specific example, at least one of the anode or cathode electrodes is formed of a metallic mesh, with regular-sized rectangular openings in the form of a grid. In one specific example, the mesh is formed of 0.023-inch diameter T316 stainless steel having a grid pattern of 20×20 grid openings per square inch. However, other dimensions, arrangements and materials can be used in other examples.

An ion-selective membrane 208 is positioned between the outer and inner electrodes 204 and 206. In one specific example, the ion-selective membrane includes a "NAFION" from E.I. du Pont de Nemours and Company, which has been cut to 2.55 inches by 2.55 inches and then wrapped around inner tubular electrode 206 and secured at the seam overlap with a contact adhesive, for example, such as a #1357 adhesive from 3M Company. Again, other dimensions and materials can be used in other examples.

In this example, the volume of space within the interior of tubular electrode 206 is blocked by a solid inner core 209 to promote liquid flow along and between electrodes 204 and 206 and ion-selective membrane 208. This liquid flow is conductive and completes an electrical circuit between the two electrodes. Electrolysis cell 200 can have any suitable dimensions. In one example, cell 200 can have a length of about 4 inches long and an outer diameter of about ¾ inch. The length and diameter can be selected to control the treatment time and the quantity of bubbles, e.g., nanobubbles and/or microbubbles, generated per unit volume of the liquid.

Cell 200 can include a suitable fitting at one or both ends of the cell. Any method of attachment can be used, such as through plastic quick-connect fittings. For example, one fitting can be configured to connect to the output tube 20 shown in FIG. 1. Another fitting can be configured to connect to the inlet filter 16 or an inlet tube, for example. In another example, one end of cell 200 is left open to draw liquid directly from reservoir 12 in FIG. 1.

In the example shown in FIG. 5, cell 200 produces anolyte EA liquid in the anode chamber (between one of the electrodes 204 or 206 and ion-selective membrane 208) and catholyte EA liquid in the cathode chamber (between the other of the electrodes 204 or 206 and ion-selective membrane 208). The anolyte and catholyte EA liquid flow paths join at the outlet of cell 200 as the anolyte and catholyte EA liquids enter tube 20 (in the example shown in FIG. 1). As a result, spray bottle 10 dispenses a blended anolyte and catholyte EA liquid through nozzle 14.

In one example, the diameters of tubes 20 and 22 are kept small so that once pump 24 and electrolysis cell 18 (e.g., cell 200 shown in FIG. 5) are energized, tubes 20 and 22 are quickly primed with electrochemically-activated liquid. Any non-activated liquid contained in the tubes and pump are kept to a small volume. Thus, in the embodiment in which the control electronics 30 activate pump and electrolysis cell in response to actuation of switch 28, spray bottle 10 produces the blended EA liquid at nozzle 14 in an "on demand" fashion and dispenses substantially all of the combined anolyte and catholyte EA liquid (except that retained in tubes 20, 22 and pump 24) from the bottle without an intermediate step of storing the anolyte and catholyte EA liquids. When switch 28 is not actuated, pump 24 is in an "off" state and electrolysis cell 18 is de-energized. When switch 28 is actuated to a closed state, control electronics 30 switches pump 24 to an "on" state and energizes electrolysis cell 18. In the "on" state, pump 24 pumps water from reservoir 12 through cell 18 and out nozzle 14.

Other activation sequences can also be used. For example, control circuit 30 can be configured to energize electrolysis cell 18 for a period of time before energizing pump 24 in order to allow the feed water to become more electrochemically activated before dispensing.

The travel time from cell 18 to nozzle 14 can be made very short. In one example, spray bottle 10 dispenses the blended anolyte and catholyte liquid within a very small period of time from which the anolyte and catholyte liquids are produced by electrolysis cell 18. For example, the blended liquid can be dispensed within time periods such as within 5 seconds, within 3 seconds, and within 1 second of the time at which the anolyte and catholyte liquids are produced.

9. Control Circuit

Referring back to FIG. 1, control electronics 30 can include any suitable control circuit, which can be implemented in hardware, software, or a combination of both, for example.

Control circuit 30 includes a printed circuit board containing electronic devices for powering and controlling the operation of pump 24 and electrolysis cell 18. In one example, control circuit 30 includes a power supply having an output that is coupled to pump 24 and electrolysis cell 18 and which controls the power delivered to the two devices. Control circuit 30 also includes an H-bridge, for example, that is capable of selectively reversing the polarity of the voltage applied to electrolysis cell 18 as a function of a control signal generated by the control circuit. For example, control circuit 30 can be configured to alternate polarity in a predetermined pattern, such as every 5 seconds with a 50% duty cycle. In another example, described in more detail below, control circuit 30 is configured to apply a voltage to the cell with primarily a first polarity and periodically reverse the polarity for only very brief periods of time. Frequent reversals of polarity can provide a self-cleaning function to the electrodes, which can reduce scaling or build-up of deposits on the electrode surfaces and can extend the life of the electrodes.

In the context of a hand-held spray bottle, it is inconvenient to carry large batteries Therefore, the available power to the pump and cell is somewhat limited. In one example, the driving voltage for the cell is in the range of about 8 Volts to about 28 Volts. But since typical flow rates through the spray bottle and electrolysis cell are fairly low, only relatively small currents are necessary to effectively activate the liquid passing through the cell. With low flow rates, the residence time within the cell is relatively large. The longer the liquid resides in the cell while the cell is energized, the greater the electrochemical activation (within practical limits). This allows the spray bottle to employ smaller capacity batteries and a DC-to-DC converter, which steps the voltage up to the desired output voltage at a low current.

For example, the spray bottle can carry one or more batteries having an output voltage of about 3-9 Volts. In one particular example, the spray bottle can carry four AA batteries, each having a nominal output voltage of 1.5 Volts at about 500 milliampere-hours to about 3 ampere-hours. If the batteries are connected in series, then the nominal output voltage would be about 6V with a capacity of about 500 milliampere-hours to about 3 ampere-hours. This voltage can be stepped up to the range of 18 Volts to 28 Volts, for example, through the DC-to-DC converter. Thus, the desired electrode voltage can be achieved at a sufficient current.

In another particular example, the spray bottle carries 10 nickel-metal hydride batteries, each having a nominal output voltage of about 1.2 Volts. The batteries are connected in series, so the nominal output voltage is about 10V to 12.5V with a capacity of about 1800 milliampere-hours. This voltage is stepped up/down to a range of 8 Volts to at least 28 Volts, for example, through the DC-to-DC converter. Thus, the desired electrode voltage can be achieved at a sufficient current.

The ability to produce a large voltage and a suitable current through the cell can be beneficial for applications in which regular tap water is fed through the cell to be converted into a liquid having enhanced cleaning and/or sanitizing properties. Regular tap water has a relatively low electrical conductivity between the electrodes of the cell.

Examples of suitable DC-to-DC converters include the Series A/SM surface mount converter from PICO Electronics, Inc. of Pelham, N.Y., U.S.A. and the NCP3064 1.5A Step-Up/Down/Inverting Switching regulator from ON Semiconductor of Phoenix, Ariz., U.S.A, connected in a boost application.

In one example, the control circuit controls the DC-to-DC converter based on a sensed current drawn from the electrolysis cell so that the DC-to-DC converter outputs a voltage that is controlled to achieve a current draw through the cell that is within a predetermined current range. For example, the target current draw is about 400 milliamperes in one specific example. In another example, the target current is 350 milliamperes. Other currents and ranges can be used in alternative embodiments. The desired current draw may depend on the geometry of the electrolysis cell, the properties of the liquid being treated and the desired properties of the resulting electrochemical reaction.

Block diagrams illustrating examples of the control electronics are described in more detail below with respect to FIGS. 7 and 20.

10. Driving Voltage for Electrolysis Cell

As described above, the electrodes of the electrolysis cell can be driven with a variety of different voltage and current patterns, depending on the particular application of the cell. It is desirable to limit scaling on the electrodes by periodically reversing the voltage polarity that is applied to the electrodes. Therefore, the terms "anode" and "cathode" and the terms "anolyte" and "catholyte" as used in the description and claims are respectively interchangeable. This tends to repel oppositely-charged scaling deposits.

In one example, the electrodes are driven at one polarity for a specified period of time (e.g., about 5 seconds) and then driven at the reverse polarity for approximately the same period of time. Since the anolyte and cathotlyte EA liquids are blended at the outlet of the cell, this process produces essentially one part anolyte EA liquid to one part catholyte EA liquid.

In another example, the electrolysis cell is controlled to produce a substantially constant anolyte EA liquid or catholyte EA liquid from each chamber without complicated valving. In prior art electrolysis systems, complicated and expensive valving is used to maintain constant anolyte and catholyte through respective outlets while still allowing the polarity to be reversed to minimize scaling. For example, looking at FIG. 2, when the polarity of the voltage applied to the electrodes is reversed, the anode 60 becomes a cathode, and the cathode 62 becomes an anode. Outlet 70 will deliver catholyte instead of anolyte, and outlet 72 will deliver anolyte instead of catholyte. Therefore, with the prior art approach, valving could be used to connect outlet 70 to cathode chamber 56 and outlet 72 to anode chamber 54 when the voltage is reversed. This results in a constant anolyte or catholyte flow through each output. Instead of using this complicated valving, one example of the present disclosure achieves substantially constant outputs through the voltage pattern supplied to the electrodes.

Figure 6:
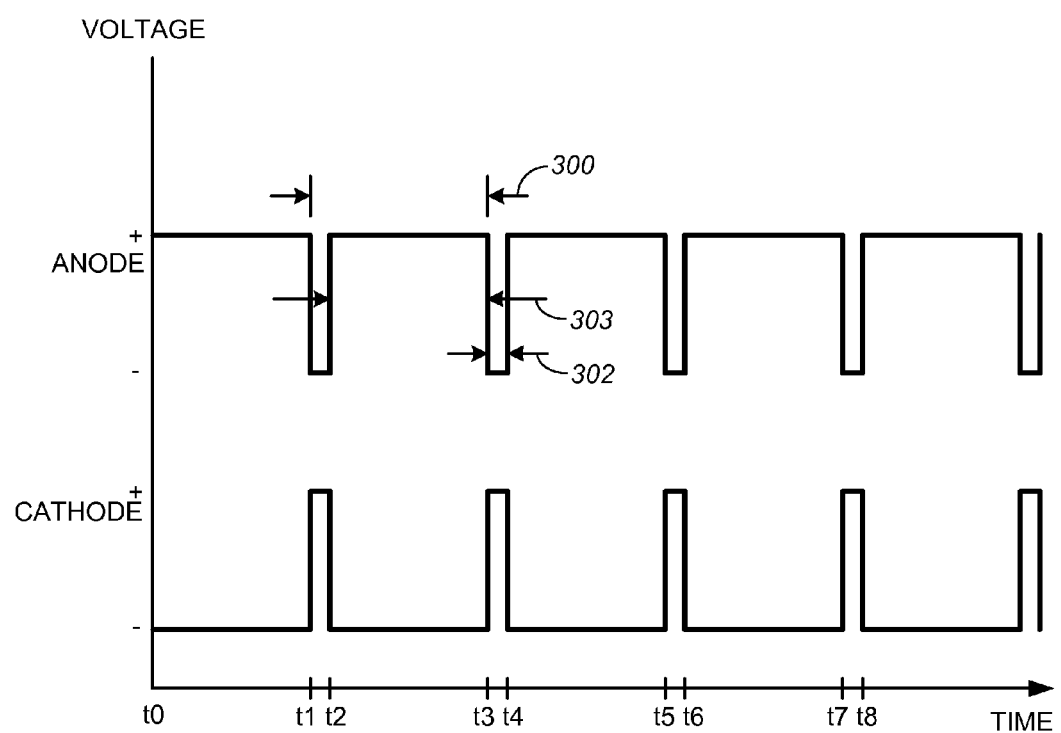
FIG. 6 is a waveform diagram illustrating the voltage pattern applied to the anode and cathode according to an exemplary aspect of the present disclosure.

FIG. 6 is a waveform diagram illustrating the voltage pattern applied to the anode and cathode according to an exemplary aspect of the present disclosure. A substantially constant, relatively positive voltage is applied to the anode, while a substantially constant, relatively negative voltage is applied to the cathode. However, periodically each voltage is briefly pulsed to a relatively opposite polarity to repel scale deposits. In this example, a relatively positive voltage is applied to the anode and a relatively negative voltage is applied to the cathode from times t0-t1, t2-t3, t4-t5 and t6-t7. During times t1-t2, t3-t4, t5-t6 and t7-t8, the voltages applied to each electrode is reversed. The reversed voltage level can have the same magnitude as the non-reversed voltage level or can have a different magnitude if desired.

The frequency of each brief polarity switch can be selected as desired. As the frequency of reversal increases, the amount of scaling decreases. However, the electrodes may loose small amounts of platinum (in the case of platinum coated electrodes) with each reversal. As the frequency of reversals decreases, scaling may increase. In one example, the time period between reversals, as shown by arrow 300, is in the range of about 1 second to about 600 seconds. Other periods outside this range can also be used.

The time period at which the voltages are reversed can also be selected as desired. In one example, the reversal time period, represented by arrow 302, is in the range of about 50 milliseconds to about 100 milliseconds. Other periods outside this range can also be used. In this example, time period of normal polarity 303, such as between times t2 and t3, is at least 900 milliseconds.

Also, the voltage can be selectively reversed periodically or non-periodically. In one particular example, the time period 300 between reversals is 1 second, and during each period of the waveform, the voltage between the electrodes is applied with the normal polarity for 900 milliseconds and then with the reversed polarity for 100 milliseconds.

With these ranges, for example, each anode chamber produces a substantially constant anolyte EA liquid output, and each cathode chamber produces a substantially constant catholyte EA output without requiring valving.

If the number of anode electrodes is different than the number of cathode electrodes, e.g., a ratio of 3:2, or if the surface area of the anode electrode is different than the surface area of the cathode electrode, then the applied voltage pattern can be used in the above-manner to produce a greater amount of either anolyte or catholyte to emphasize cleaning or sanitizing properties of the produced liquid. For example, if cleaning is to be emphasized, then a greater number of electrodes can be driven to the relatively negative polarity (to produce more catholyte) and a lesser number of electrodes can be driven to the relatively positive polarity (to produce less anolyte). If sanitizing is to be emphasized, then a greater number of electrodes can be driven to the relatively positive polarity (to produce more anolyte) and a lesser number of electrodes can be driven to the relatively negative polarity (to produce less catholyte).

If the anolyte and catholyte outputs are blended into a single output stream prior to dispensing, then the combined anolyte and catholyte output liquid can be tailored to emphasize cleaning over sanitizing or to emphasize sanitizing over cleaning. In one embodiment, the control circuit includes a further switch, which allows the user to select between cleaning and sanitizing modes. For example, in the embodiment shown in FIG. 1, spray bottle 10 can include a user-operable cleaning/sanitizing mode switch that is mounted to the bottle.

In one exemplary embodiment of the disclosure, a handheld spray bottle such as those shown in FIGS. 1 and 8 carries tubular electrolysis cell such as cell 200 shown in FIG. 5. The electrolysis cell is driven with a voltage to emphasize enhanced cleaning properties by generating a greater amount of catholyte EA liquid than anolyte EA liquid per unit of time. In cell 200, outer cylindrical electrode 204 has a greater diameter and therefore a greater surface area than inner cylindrical electrode 206. To emphasize enhanced cleaning properties, the control circuit drives cell 200 so that, for the majority of period of the driving voltage pattern, outer electrode 204 serves as the cathode and inner electrode 206 serves as the anode. Since the cathode has a larger surface area than the anode, cell 200 will generate more catholyte than anolyte per unit of time through the combined outlet of the cell. Referring to FIG. 6, in this example, the control circuit applies a relatively positive voltage to the anode (electrode 206) and a relatively negative voltage to the cathode (electrode 204) from times t0-t1, t2-t3, t4-t5 and t6-t7. During times t1-t2, t3-t4, t5-t6 and t7-t8, the voltages applied to each electrode is briefly reversed.

In this example, the spray bottle is filled with regular tap water only. Thus the liquid that is pumped through and electrochemically activated with cell 200 consists solely of regular tap water. The tap water is electrochemically activated, as discussed herein, and dispensed as a blended anolyte and catholyte stream through the spray nozzle. The spray output therefore has enhanced cleaning properties, wherein the amount of catholyte exceeds the amount of anolyte in the blended stream. Enhanced sanitizing properties can be emphasized in an alternative embodiment by making electrode 204 primarily an anode and electrode 206 primarily a cathode using the waveforms shown in FIG. 6, for example.

It has been found that such frequent, brief polarity reversals for de-scaling the electrodes may have a tendency also to shed materials often used for plating the electrodes, such as platinum, from the electrode surface. Thus in one embodiment, electrodes 204 and 206 comprise unplated electrodes, such as metallic electrodes or conductive plastic electrodes. For example, the electrodes can be unplated metallic mesh electrodes.

11. Status Indicator Light Illuminating Through Liquid 11.1 Control Circuit For Bottles Shown in FIGS. 1 and 8-16

Another aspect of the present disclosure relates to providing a humanly-perceptible indicator, which indicates a functional status of the electrolysis cell, such as the oxidation-reduction potential of the EA liquid. The spray bottle and/or other devices disclosed herein can be modified to include a visual indicator of the output liquid's oxidation-reduction potential.

The level of power consumed by the electrolysis cell can be used to determine whether the cell is operating correctly and therefore whether the liquid (sparged water, EA anolyte, and/or EA catholyte) produced by the cell is electrochemically activated to a sufficient level. Power consumption below a reasonable level can reflect various potential problems such as use of ultra-pure feed water or feed water having a generally low electrolyte content (e.g., low sodium/mineral content) such that the water does not conduct a sufficient level of electrical current within the functional generator. The current consumption can therefore also indicate high or low levels of oxidation-reduction potential, for example. Also, the current drawn by the pump may be used to indicate whether the pump is operating correctly or whether there is a problem, such as the pump being stalled.

Figure 7:
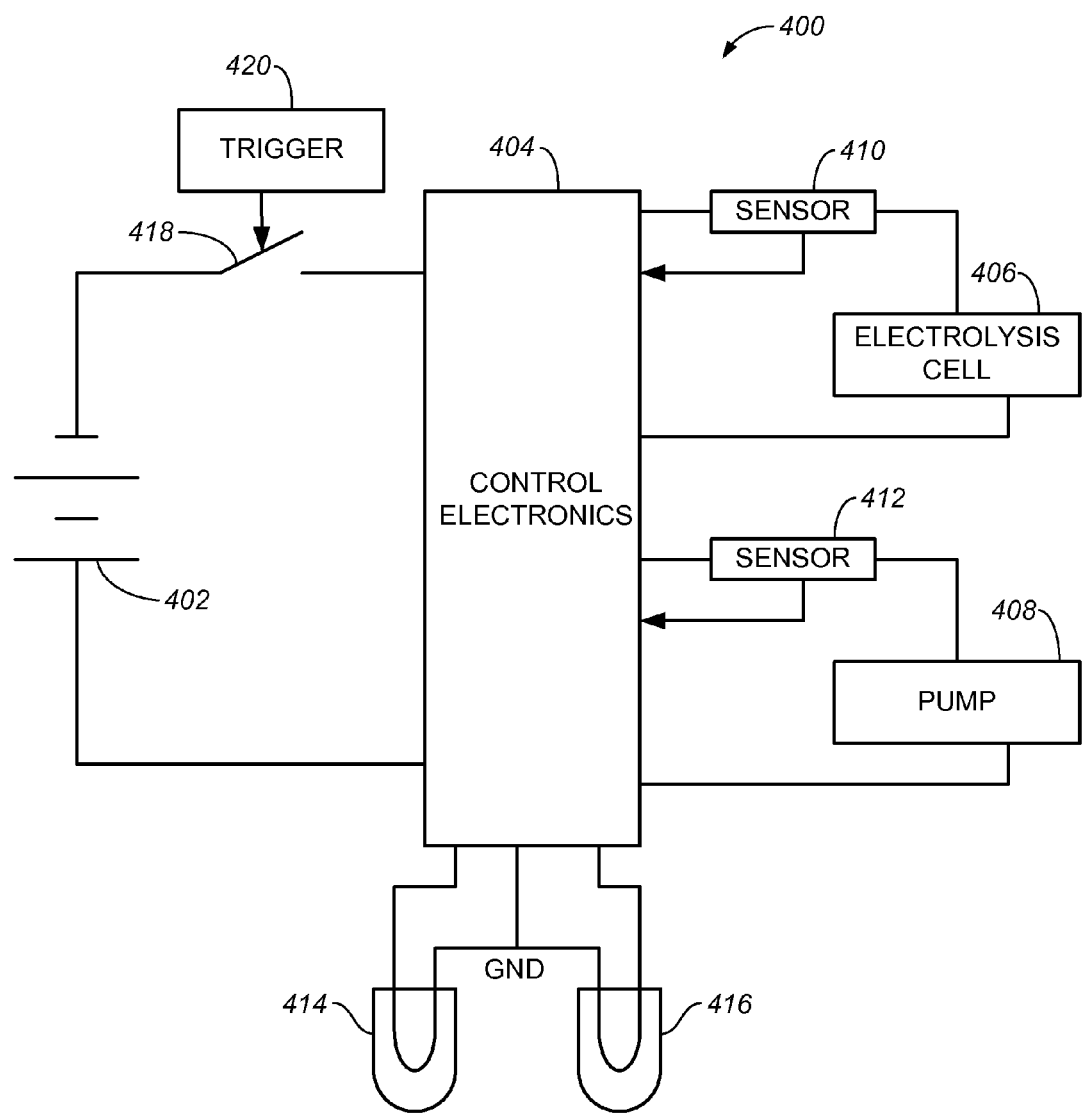
FIG. 7 is a block diagram of a system having an indicator according to an embodiment of the disclosure, which can be incorporated into any of the embodiments disclosed herein, for example.

FIG. 7 is a block diagram of a system 400 having an indicator according to an embodiment of the disclosure, which can be incorporated into any of the embodiments disclosed herein, for example. System 400 includes power supply (such as a battery) 402, control electronics 404, electrolysis cell 406, pump 408, current sensors 410 and 412, indicator lights 414 and 416, switch 418 and trigger 420. For simplicity, the liquid inputs and outputs of electrolysis cell 404 are not shown in FIG. 7. All elements of system 400 can be powered by the same power supply 402 or by two or more separate power supplies, for example.

Control electronics 404 are coupled to control the operating state of electrolysis cell 406, pump 408 and indicator lights 414 and 416 based on the present operating mode of system 400 and user control inputs, such as trigger 420. In this example, switch 418 is coupled in series between power supply 402 and control electronics 404 and serves to couple and decouple power supply 402 to and from power inputs of control electronics 404 depending on the state of trigger 420. In one embodiment, switch 418 includes a momentary, normally-open switch that closes when trigger 420 is depressed and opens when trigger 420 is released.

In an alternative example, switch 418 is configured as an on/off toggle switch, for example, that is actuated separately from trigger 420. Trigger 420 actuates a second switch that is coupled to an enable input of control electronics 404. Other configurations can also be used.

In both embodiments, when trigger 420 is depressed, control electronics 404 is enabled and generates appropriate voltage outputs for driving electrolysis cell 406 and pump 408. For example, control electronics 404 can produce a first voltage pattern for driving the electrolysis cell 406, such as those patterns described herein, and a second voltage pattern for driving pump 408. When trigger 420 is released, control electronics is powered off and/or otherwise disabled from producing the output voltages to cell 406 and pump 408.

Current sensors 410 and 412 are coupled in electrical series with electrolysis cell 406 and pump 408, respectively, and each provide a signal to control electronics 404 that is representative of the respective electrical current drawn through cell 406 or pump 406. For example, these signals can be analog or digital signals.

In one particular example, system 400 includes a sensor 410 for sensing the current drawn by electrolysis cell 406, but no sensor 412 for sensing current drawn by pump 408. The control electronics 404 includes a microcontroller, such as an MC9S08SH4CTG-ND Microcontroller available from Digi-Key Corporation of Thief River Falls, Minn., U.S.A., which controls a DRV8800 full bridge motor driver circuit available from Texas Instruments Corporation of Dallas, Tex., U.S.A. The driver circuit has an H-switch that drives the output voltage to electrolysis cell 406 according to a voltage pattern controlled by the microcontroller. The H-switch has a current sense output that can be used by the microcontroller to sense the current drawn by cell 406.

Control electronics 404 compares the sensor outputs to predetermined threshold current levels or ranges and then operates indicators 414 and 416 as a function of one or both of the comparisons. The threshold current levels or ranges can be selected to represent predetermined power consumption levels, for example.

Indicators 414 and 416 each can include any visually perceptible indicator, such as an LED. In one example, indicator lights 414 and 416 have different colors to indicate different operating states. For example, indicator light 414 might be green, which when illuminated indicates a normal, properly functioning electrolysis cell and/or pump, and indicator 416 might be red, which when illuminated indicates a problem in the operating state of the electrolysis cell and/or pump. In a particular example, the bottle contains four green LEDs 414 and four red LEDs 416 for a strong illumination of the liquid contained in the bottle.

In the example shown in FIG. 7, control electronics 404 operate the indicator lights 414 and 416 as a function of the current levels sensed by current sensors 410 and/or 412. For example, control electronics 404 can turn off (or alternatively, turn on) one or both of the indicator lights as a function of whether the current level sensed is above or below a threshold level or within a range. Indicator lights 414 and 416 can be operated by separate power signals and a common ground, for example, provided by control electronics 404 in one embodiment, control electronics 404 illuminates the green indicator light 414 in a steady "on" state and turns off the red indicator light 416 when the sensed current level the cell 406 is above the respective threshold level (or within the predefined range). In contrast, control electronics 404 illuminates the red indicator light 416 in a steady "on" state and the green indicator light 414 in a steady "off" state when the sensed current level of cell 406 is below the respective threshold level.

The control electronics 404 modulates the green indicator light 414 between the on and off states when the current drawn by pump 408 is outside of a predetermined range. Any suitable range can be used for the pump current, such as between 1.5 Amps and 0.1 Amps. Other ranges can also be used. In a further example, control electronics 404 illuminates the green indicator light 414 in a steady "on" state and turns off the red indicator light 416 when the sensed current levels of both the cell 406 and the pump 408 are within their respective predetermined, and if not, illuminates the red indicator light 416 and turns off the green indicator light 414.

In another embodiment, one or more indicator lights are operated in a steady "on" state when the sensed current level is above the threshold level, and are cycled between the "on" state and "off" state at a selected frequency to indicate a problem when the sensed current level of electrolysis cell 406 is below the threshold level. Multiple threshold levels and frequencies can be used in other embodiments. Also, a plurality of separately-controlled indicator lights can be used, each indicating operation within a predefined range. Alternatively or in addition, the control electronics can be configured to alter the illumination level of one or more indicator lights as a function of the sensed current level relative to one or more thresholds or ranges, for example. In a further example, separate indicator lights can be used for separately indicating the operating state of the electrolysis cell and the pump. Other configurations can also be used.

11.2 Illumination Through the Liquid

As described in more detail below, indicator lights 414 and/or 416 can be positioned on the apparatus (such as on the spray bottle) to illuminate the liquid itself, either prior to treatment by electrolysis cell 404 and/or after treatment. For example, the indicator light, when illuminated, generates luminous flux in the visible wavelength range that is visually perceptible through the liquid from a viewpoint that is exterior to the apparatus. For example, the liquid may diffuse at least a portion of the light, giving a visual impression that the liquid, itself, is illuminated. In one embodiment, the apparatus comprises a container, lumen or other element that contains the liquid and comprises a material and/or portion that is at least translucent and positioned to transmit at least some of the light produced by indicator 414 and/or 416 when illuminated. This container, lumen or other element is at least partially visible from an exterior of the apparatus.

The term "at least translucent" includes translucent, semi-transparent, fully transparent, and any term that means at least some of the light illuminating from the indicator is humanly perceptible through the material.

FIGS. 8-16 illustrate examples of a hand-held spray bottle 500 and 500' having an electrolysis cell and at least one indicator light, wherein at least some of the light illuminating from the indicator is humanly perceptible from a viewpoint that is external to the bottle. The particular bottle configurations and constructions shown in the drawings are provided as non-limiting examples only. The same reference numerals are used in FIGS. 8-16 for the same or similar elements.

Figure 8A:
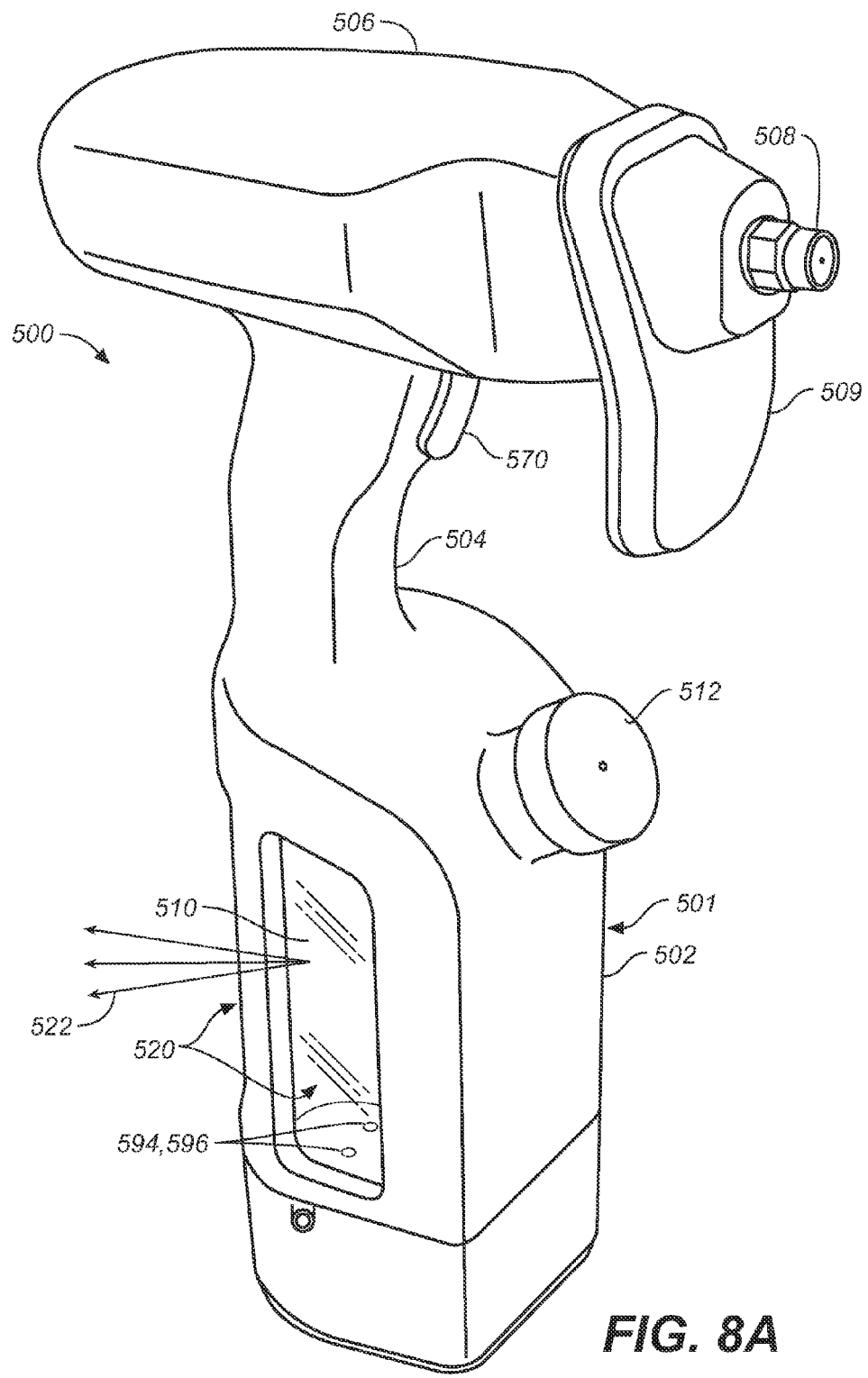
FIG. 8A is a perspective view of a spray bottle having an indicator light that illuminates through liquid carried by the bottle.

Referring to FIG. 8A, bottle 500 includes a housing 501 forming a base 502, a neck 504, and a barrel or head 506. The tip of barrel 506 includes a nozzle 508 and a drip/splash guard 509. Drip/splash guard 509 also serves as a convenient hook for hanging bottle 500 on a utility cart, for example. As shown in more detail below, housing 501 has a clamshell-type construction with substantially symmetrical left and right hand sides attached together, such as by screws. Base 502 houses a container 510, which serves as a reservoir for liquid to be treated and then dispensed through nozzle 508. Container 510 has a neck and threaded inlet (with a screw cap) 512 that extends through base 502 to allow container 510 to be filled with a liquid. Inlet 512 is threaded to receive a cap seal.

In this example, the side walls of housing base 502 have a plurality of openings or windows 520 about its circumference through which container 510 is visible. In this example, the openings 520 are formed by an absence of the housing material within the opening. In another example, the openings are formed by a material that is at least translucent. In another example, shown in FIG. 8B, the entire housing or a portion of the housing is at least translucent.

Similarly, container 510 is formed of a material that is at least translucent. For example, container 510 can be fabricated as a blow mold of a clear polyester material. As explained in more detail below, housing 501 also contains a circuit board carrying a plurality of LED indicator lights 594, 596 (corresponding to lights 414 and 416 shown in FIG. 7). The lights are positioned beneath the base of container 510 to transmit light through a base wall of container 510 and into any liquid contained in the container. The liquid diffuses at least a portion of the light, giving an appearance of the liquid being illuminated. This illumination is visible from a viewpoint external to housing 501, through openings 520. The color of the light and/or other illumination characteristics such as on/off modulation, intensity, etc. that are controlled by the control electronics are observable through openings 510 to give the user an indication of the functional status of the bottle. Arrows 522 represent illumination from the indicator light that is transmitted through the liquid in container 510 and visible from an exterior of the bottle, through openings 520 in housing 501.

For example, the liquid can be illuminated with a green LED to indicate that the electrolysis cell and/or pump are functioning properly. Thus, the user can be assured that the treated liquid dispensed from nozzle 508 has enhanced cleaning and/or sanitizing properties as compared to the source liquid contained in container 510. Also, illumination of the source liquid in container 510, although not yet treated, gives an impression that the liquid is "special" and has enhanced properties.

Similarly, if the electrolysis cell and/or pump are not functioning properly, the control electronics illuminates the red LED, giving the source liquid a red appearance. This gives the user an impression that there is a problem and that the dispensed liquid may not have enhanced cleaning and/or sanitizing properties.

Although in the example shown in FIG. 8A the illumination is visible through container 510, the indicator lights can be positioned to illuminate any portion of the flow path from a liquid inlet to the bottle and nozzle 508, including any elements upstream and/or downstream of the electrolysis cell. The housing can be modified in any manner to allow this illumination to be visible by a user. For example, the liquid can be illuminated in a delivery tube extending from the output of the electrolysis cell to the nozzle 508. Barrel 506 can be modified to include an opening to expose the delivery tube, or a portion of the tube can extend along the exterior of barrel 506, for example.

Figure 8B:
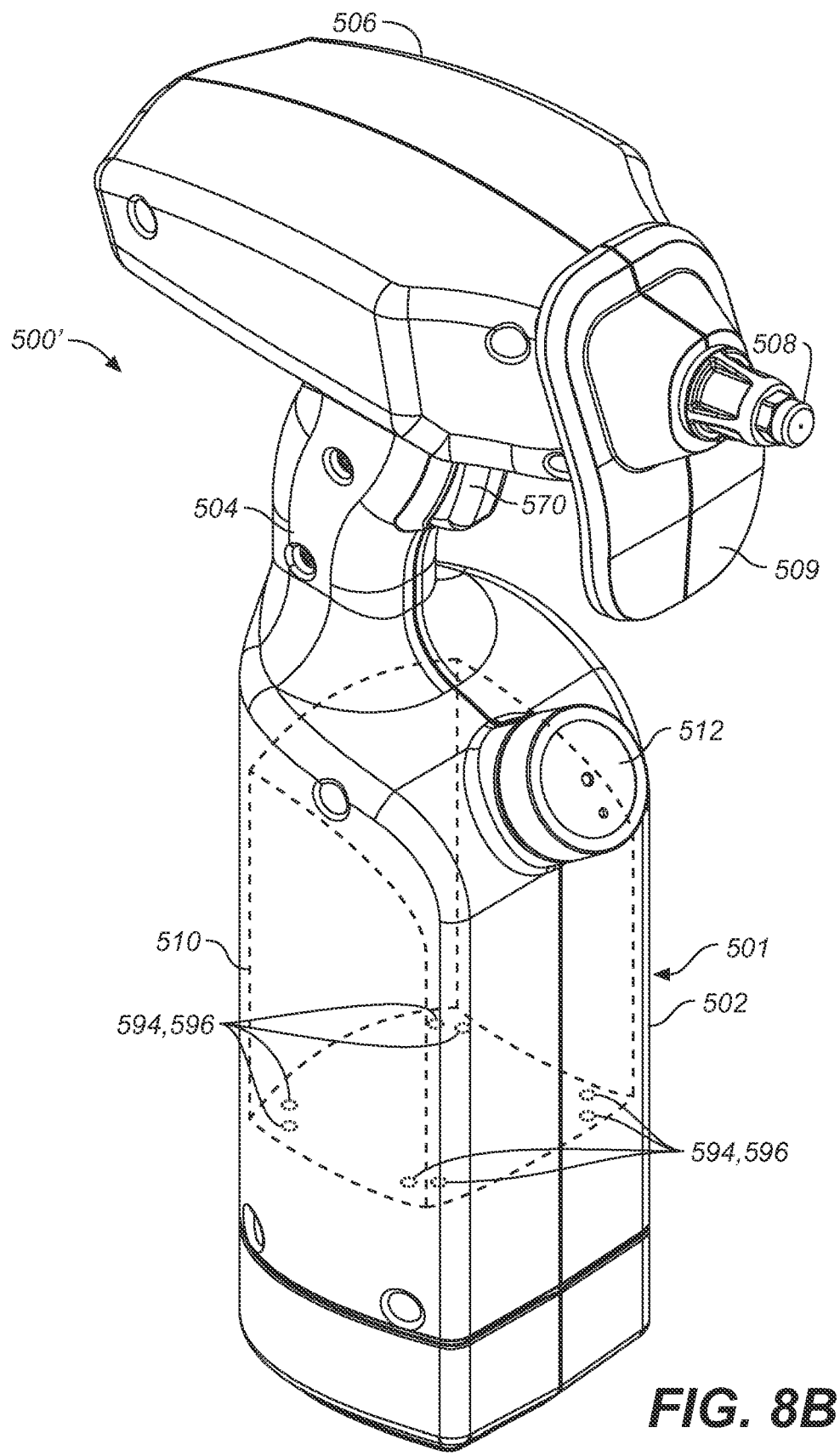
FIG. 8B is a perspective view of a spray bottle having an indicator light that illuminates through liquid carried by the bottle, according to an alternative embodiment of the disclosure.

FIG. 8B is a perspective view of a bottle 500' which lacks the windows 520 if the embodiment shown in FIG. 8A. In this example, the entire housing 501 or a portion of the housing is at least translucent. For example, housing 501 can be fabricated of polycarbonate. The same reference numerals are used in FIG. 8B as were used in FIG. 8A for the same or similar elements. Although not expressly shown in FIG. 8B, with a translucent housing, the internal components of bottle 500' are visible through housing 501 from a viewpoint that is external to the housing. For example, the container 510 (shown in phantom) and the liquid contained therein are visible through housing 501. In this example, there are four red LEDs 594 and four green LEDs 596 (also shown in phantom), arranged in pairs in each corner of the bottle. Thus, when LEDs 594 and/or 596 are illuminated, the liquid diffuses at least a portion of the light, giving an appearance of the liquid being illuminated. This illumination is visible from a viewpoint external to housing 501 in the same manner as shown in FIG. 8A, except illumination would not be limited to the "windows" 520.

Figure 8C:
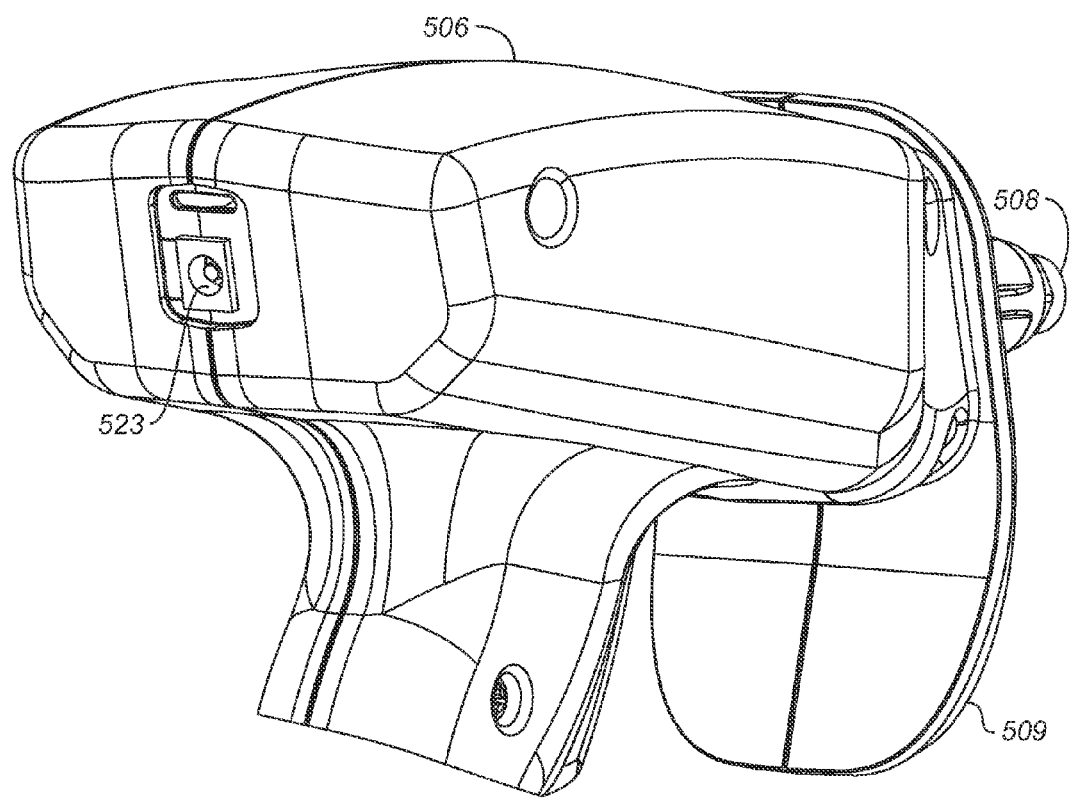
FIG. 8C is a rear, perspective view of a head of the bottle shown in FIG. 8B.

FIG. 8C is a perspective view of the back end of the barrel (or head) 506 of bottle 501', which illustrates an electrical power jack 523 for connecting to the cord of a battery charger (not shown). In the example in which bottle 500' carries rechargeable batteries, these batteries can be recharged through jack 523.

FIGS. 9-16 illustrate further details of the particular bottle 500' shown in FIG. 8B.

Figure 9A:
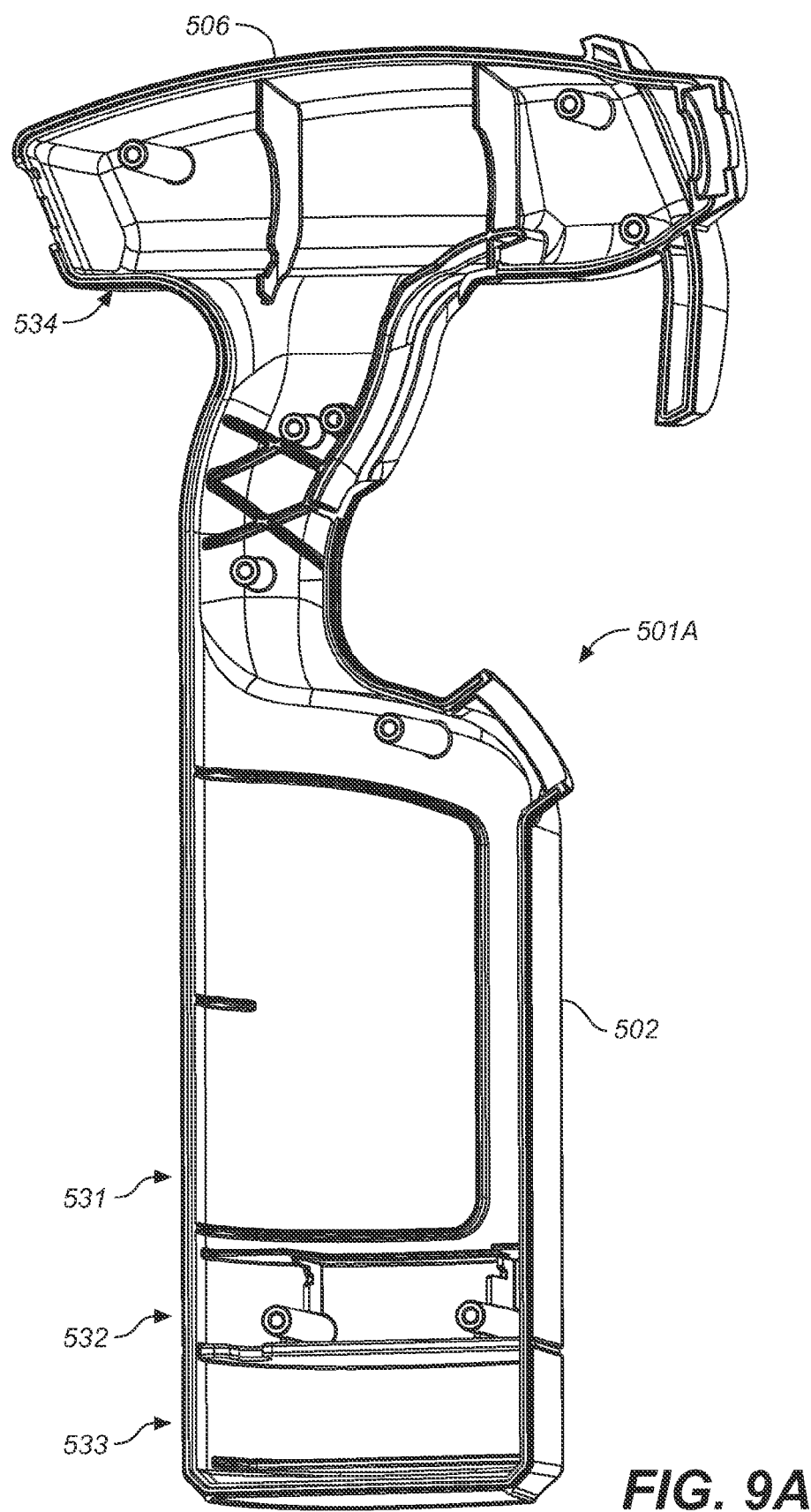
FIGS. 9A and 9B are perspective views of a left-hand side housing.
Figure 9B:
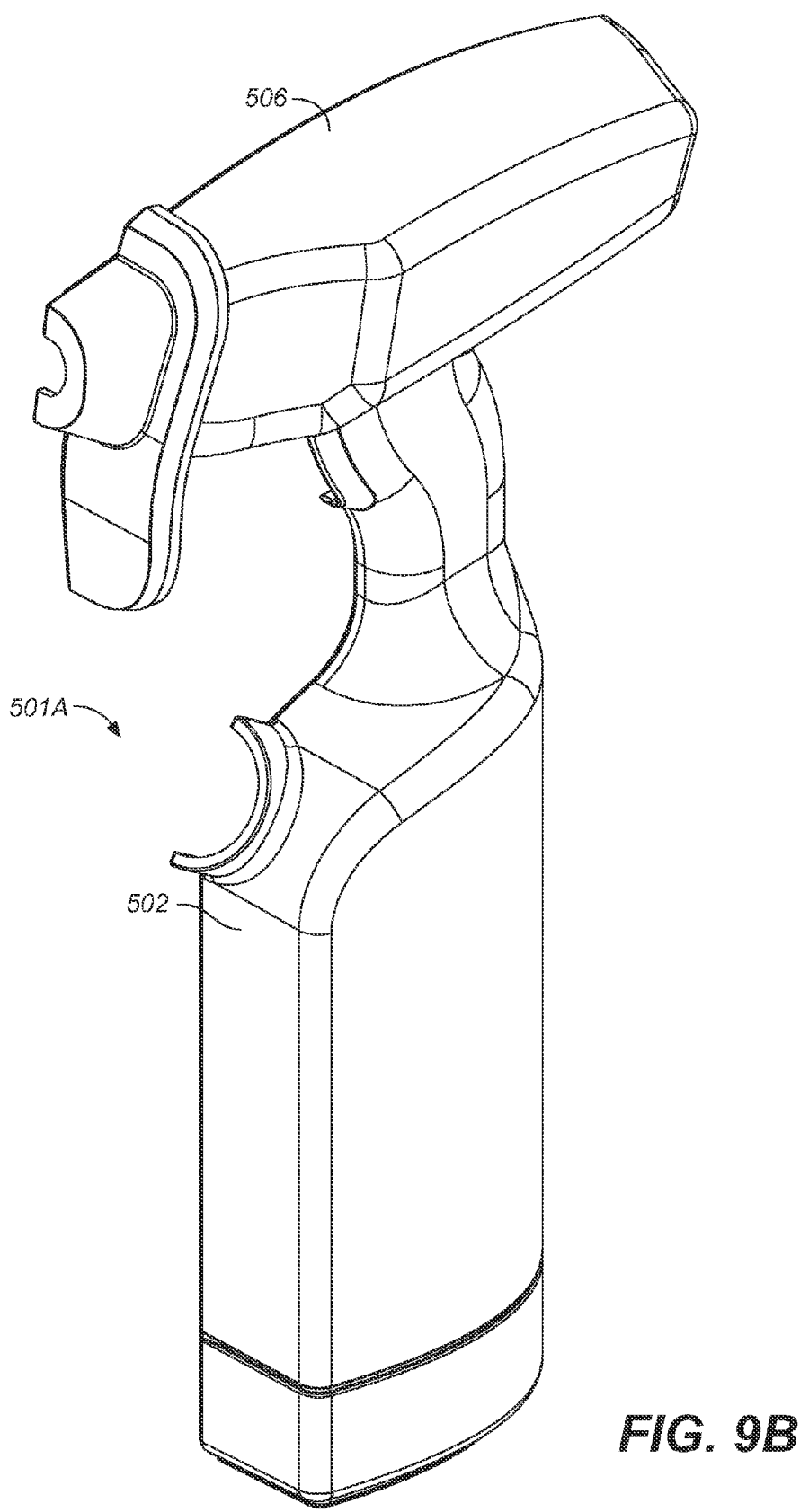
Figure 9C:
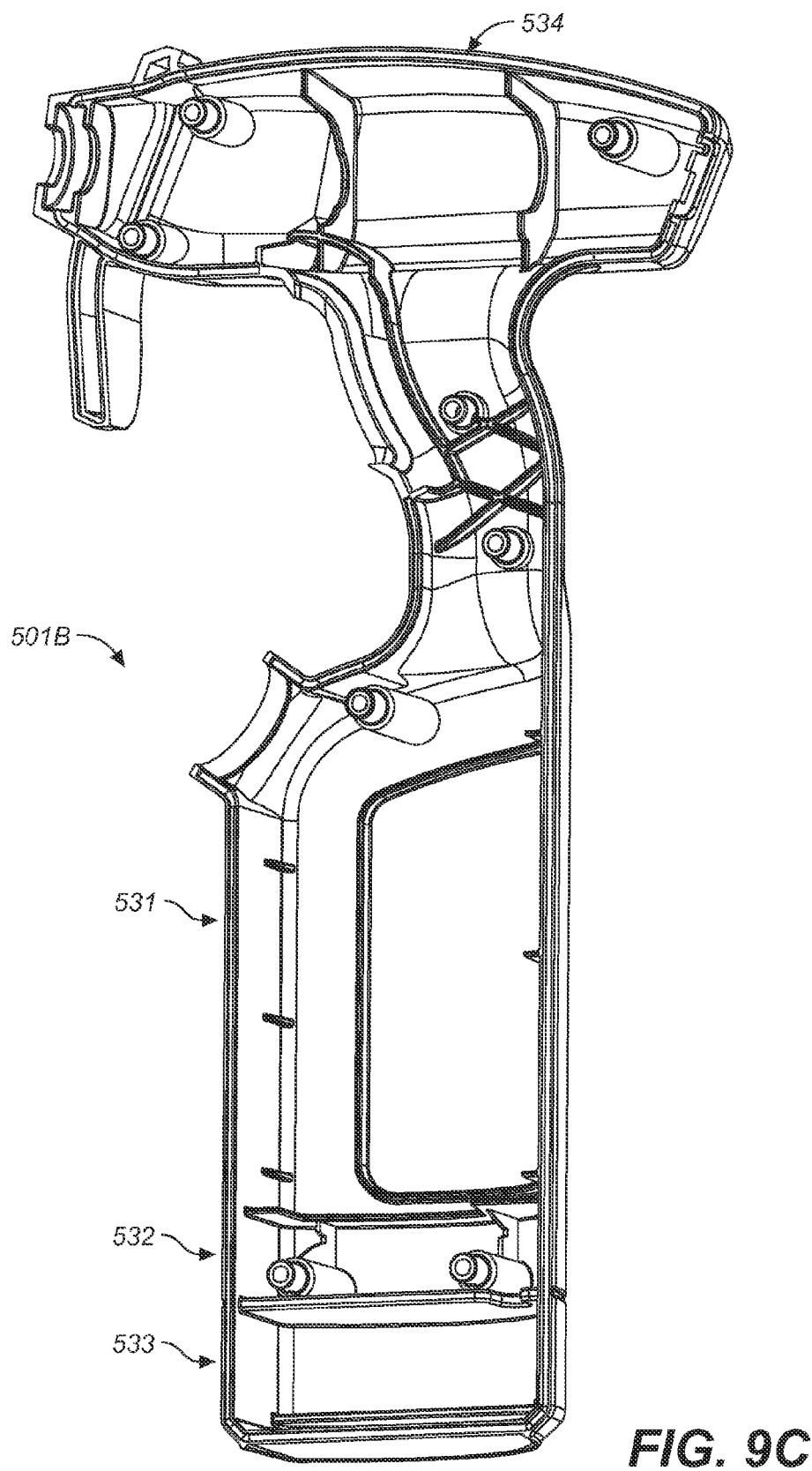
FIG. 9C is a perspective view of a right-hand side housing of the bottle shown in FIG. 8B.

FIGS. 9A and 9B are perspective views of the left-hand side 501A of housing 501, and FIG. 9C is a perspective view of the right-hand side 501B of housing 501.

The left and right hand sides 501A and 501B, when attached to one another form a plurality of compartments for containing various elements of the bottle. For example, housing base 502 includes a first compartment 531 for containing liquid container 510 (shown in FIGS. 8A, 8B), a second compartment 532 for containing a circuit board supporting the control electronics, and a third compartment 533 for containing a plurality of batteries to power the control electronics. Barrel 506 includes a compartment 534 for containing the electrolysis cell and pump.

Figure 10:
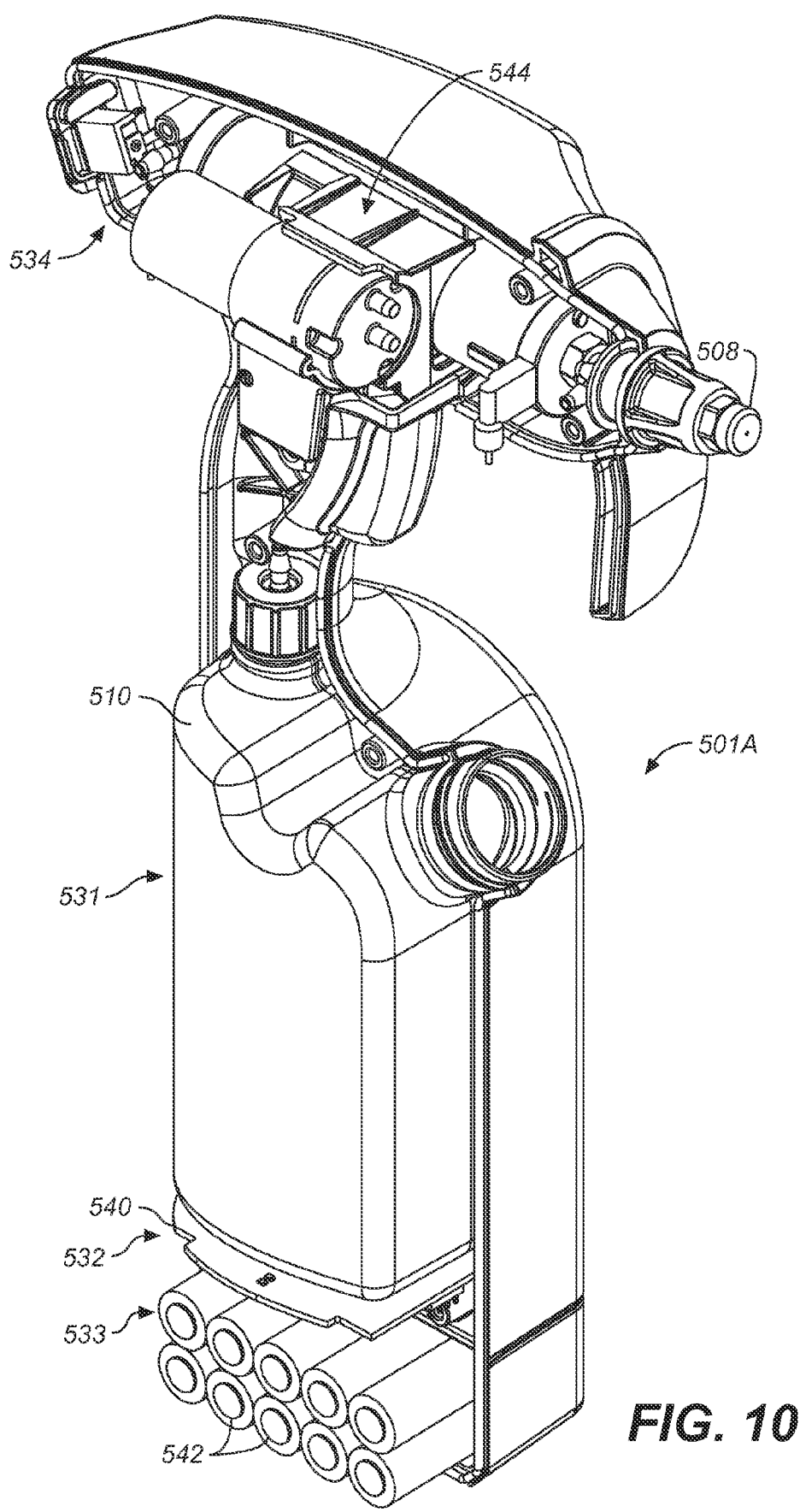
FIG. 10 illustrates various components installed in the left-hand side housing.

FIG. 10 illustrates various components installed in the left-hand side 501A of housing 50i. Container 510 is installed in compartment 531, circuit board 540 is installed in compartment 532, batteries 542 are installed in compartment 533, and pump/cell assembly 544 is installed in compartment 534. The various tubes that connect container 510, pump/cell assembly and nozzle 508 are not shown in FIG. 10.

Figure 11A:
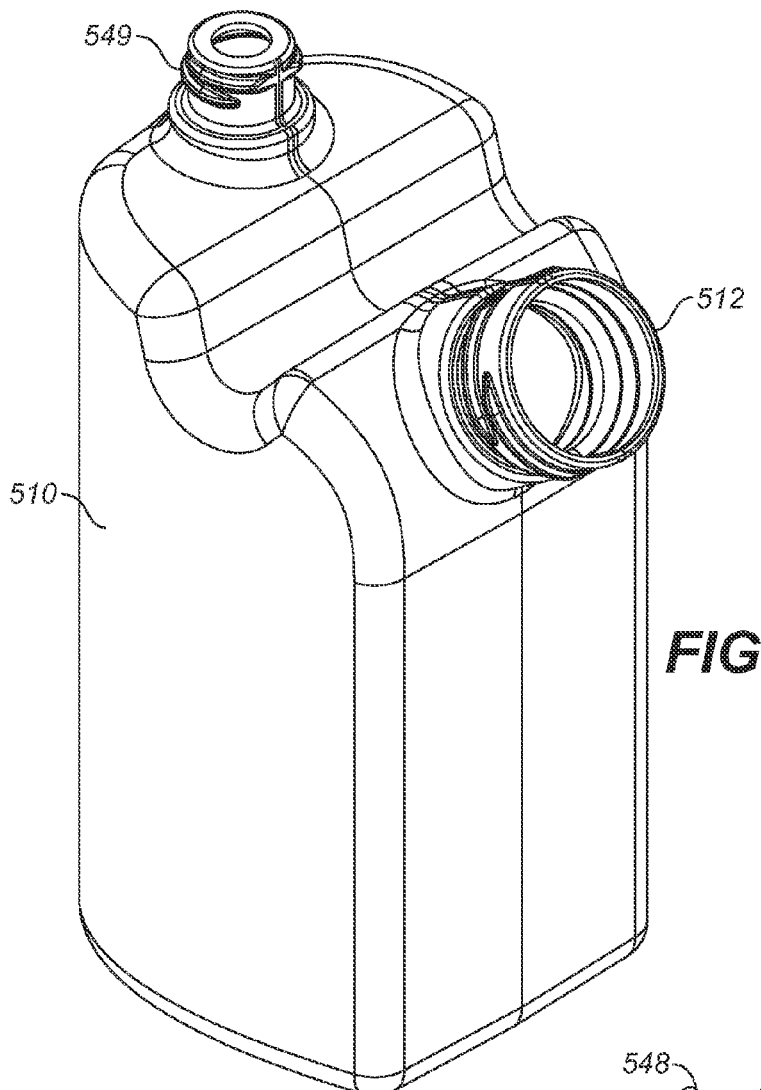
FIGS. 11A and 11B illustrate a liquid container carried by the bottle shown in FIG. 8B.
Figure 11B:
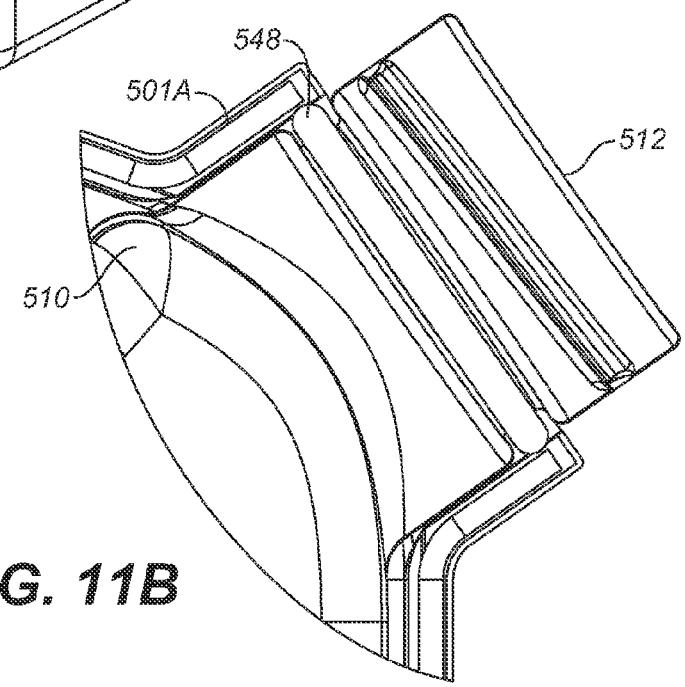

FIGS. 11A and 11B illustrate container 510 in greater detail. FIG. 11A is a perspective view of container 510, and FIG. 11B is a fragmentary, cross-sectional view of the inlet 512 of container 510 installed in housing 501A. An o-ring 548 seals the outer diameter surface of the neck of inlet 512 within housing 501A. The threads on inlet 512 receive a cap (not shown) to seal the inlet opening. Container 510 further includes an outlet 549 for receiving a tube (not shown) for drawing liquid from container 510. The tube may include an inlet filter as described with reference to FIG. 1, for example.

FIG. 12A illustrates a fragmentary, close-up view of pump/cell assembly 544 installed in the barrel 506 of housing half 501A. FIG. 12B is a perspective view of pump/cell assembly 544 removed from the housing. FIG. 12C shows a bottom, perspective view of the assembly with the trigger 570 removed.

Pump/cell assembly 544 includes a pump 550 and an electrolysis cell 552 mounted within a bracket 554. The pump 550 has a first port 555 that is fluidically coupled to the tube (not shown) extending from the outlet 549 of container 510 and a second port 555 that is fluidically coupled through another tube (also not shown) to the inlet 556 of electrolysis cell 552.

Electrolysis cell 552 has an outlet 557 that is fluidically coupled to nozzle 508. In one example, electrolysis cell 552 corresponds to the tubular electrolysis cell 200 discussed with reference to FIG. 5. However, any suitable electrolysis cell can be used in alternative embodiments, and the cell can have any shape and/or geometry. For example, the cell can have electrodes that are cylindrical as shown in FIG. 5 or substantially planar, parallel plates. O-ring 560 provides a seal about the nozzle 508 for housing 501.

Bottle 500' further includes a trigger 570, which actuates a momentary push-button on/off switch 572. Trigger 570 actuates about pivot 574 when depressed by a user. A spring 576 (shown in FIG. 12C) biases trigger 570 in a normally released state and thus switch 572 in an off state. Switch 572 has electrical leads 578 for connecting to the control electronics on circuit board 540, shown in FIG. 10.

As described with reference to the block diagram shown in FIG. 7, when trigger 570 is depressed, switch 572 actuates to the "on" state, thereby providing electrical power to the control electronics, which energizes pump 550 and electrolysis cell 552. When energized, pump 550 draws liquid from container 510 and pumps the liquid through electrolysis cell 552, which delivers a combined anolyte and catholyte EA liquid to nozzle 508. When pump 550 and/or electrolysis cell 552 are functioning properly, the control electronics also illuminate the liquid within container 510 with the LEDs installed on the circuit board or another location in or on bottle 500'.

Figure 13:
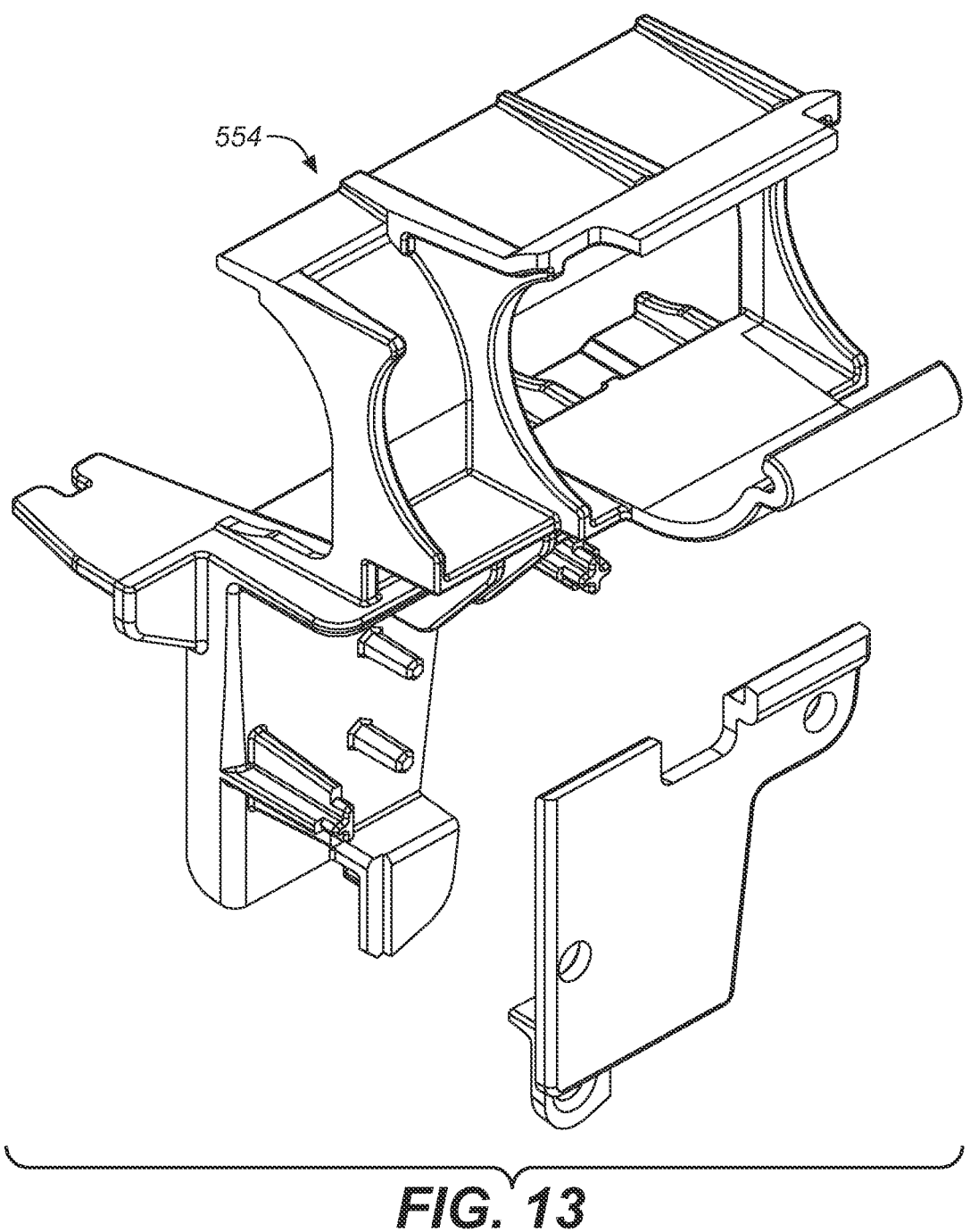
FIG. 13 illustrates an exploded, perspective view of a mounting bracket of the assembly shown in FIGS. 12A-12C.

FIG. 13 illustrates bracket 554 in greater detail.

Figure 14A:
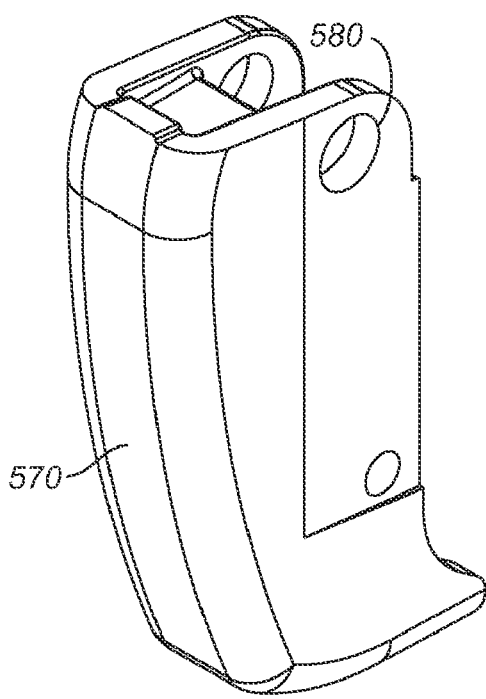
FIGS. 14A and 14B are perspective views of a trigger of the bottle shown in FIG. 8B.
Figure 14B:
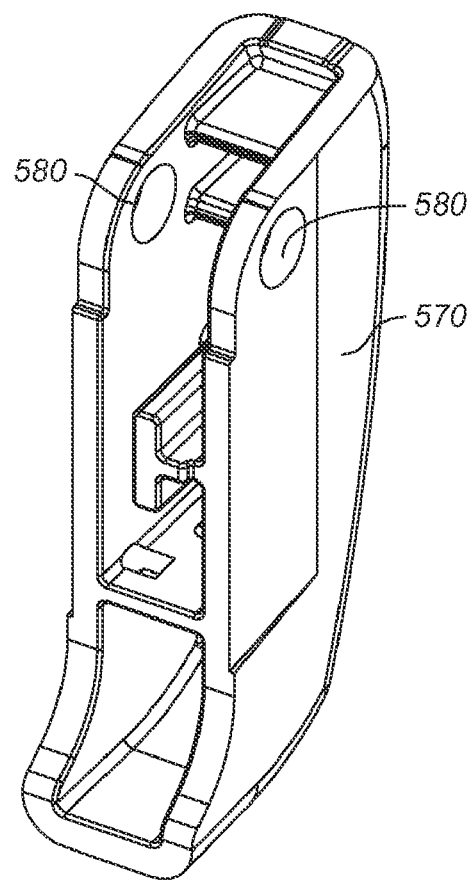

FIGS. 14A and 14B are perspective views of trigger 570. Trigger 570 has a set of apertures 580 for receiving a pin or pins that define the pivot point of the trigger.

Figure 15A:
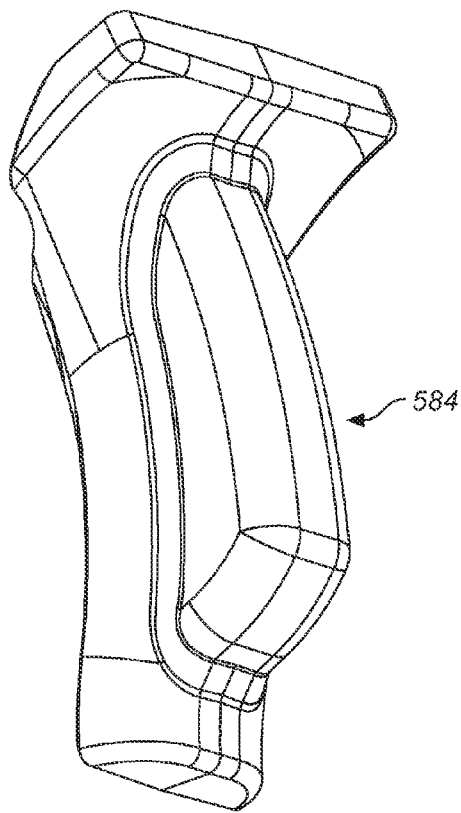
FIGS. 15A and 15B are perspective views of a trigger boot, which overlies the trigger.
Figure 15B:
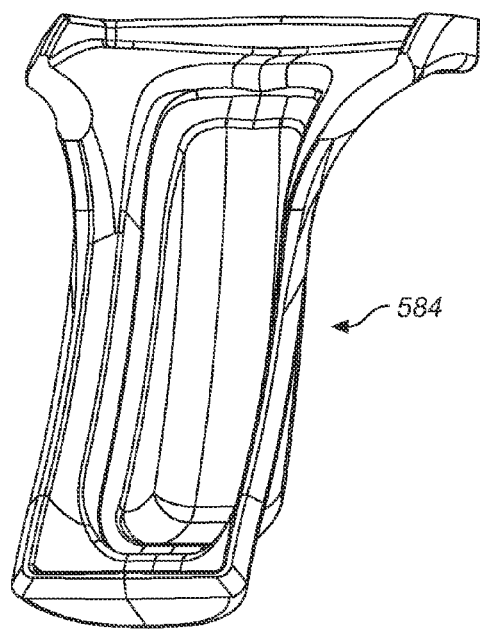

FIGS. 15A and 15B are perspective views of a trigger boot 584, which overlies trigger 570. Boot 584 provides a protective layer for trigger 570 and seals the edges of housing 501 about the trigger.

Figure 16A:
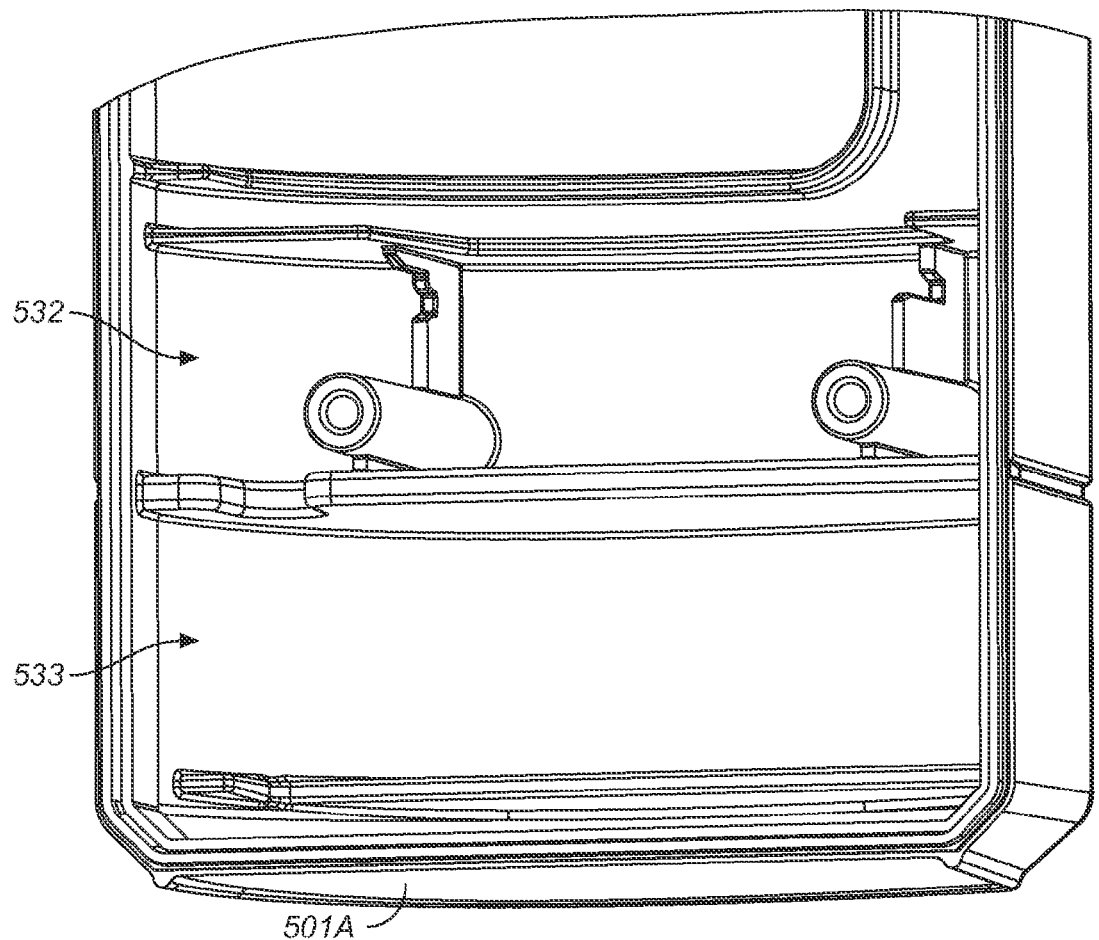
FIG. 16A illustrates lower compartments of a housing half in greater detail.
Figure 16B:
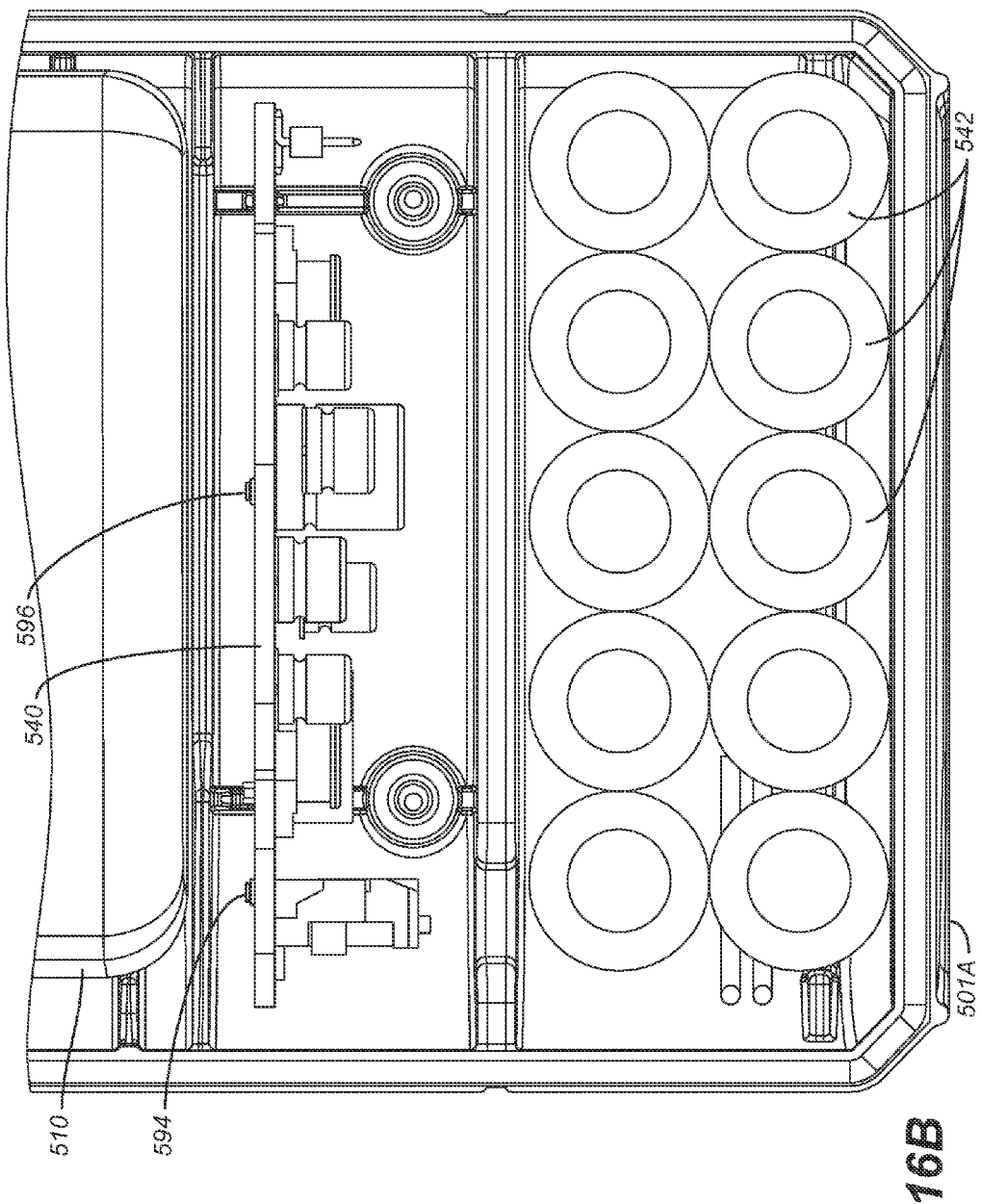
FIG. 16B illustrates a circuit board and batteries mounted within the compartments shown in FIG. 16A.

FIG. 16A illustrates compartments 532 and 533 of housing half 501A in greater detail. FIG. 16B illustrates the circuit board 540 mounted within compartment 532 and batteries 542 mounted within compartment 533.

In addition, circuit board 540 includes a plurality of light-emitting diodes (LEDs) 594 and 596. In this example, the LEDs are positioned on the top surface of circuit board 540 such that light radiating from the LEDs illuminates the liquid in container 510 through the base of the container. Other arrangements can also be used. The LEDs can have different colors and be controlled separately, as described above, to indicate different operating states or characteristics, for example.

12. Illumination Through the Liquid in Other Apparatus

The features and methods described herein, such as those of the electrolysis cell and the indicator light(s), can be used in a variety of different apparatus, such as on a spray bottle, a mobile surface cleaner, and/or a free-standing or wall-mount electrolysis platform. For example, they can be implemented onboard (or off-board) a mobile surface cleaner, such as a mobile hard floor surface cleaner, a mobile soft floor surface cleaner or a mobile surface cleaner that is adapted to clean both hard and soft floors or other surfaces, for example.

Field et al. U.S. Publication No. 2007/0186368 A1 discloses various apparatus in which the features and methods described herein can be used, such as a mobile surface cleaner having a mobile body configured to travel over a surface. The mobile body has a tank for containing a cleaning liquid, such as tap water, a liquid dispenser and a flowpath from the tank to the liquid dispenser. An electrolysis cell is coupled in the flowpath. The electrolysis cell has an anode chamber and a cathode chamber separated by an ion exchange membrane and electrochemically activates tap water that has passed through the functional generator.

The functional generator converts the tap water into an anolyte EA liquid and a catholyte EA liquid. The anolyte EA liquid and the catholyte EA liquid can be separately applied to the surface being cleaned and/or sanitized, or can be combined on-board the apparatus to form a combination anolyte and catholyte EA liquid and dispensed together through a cleaning head, for example.

Field et al. U.S. Publication No. 2007/0186368 A1 also discloses other structures on which the various structural elements and processes disclosed herein can be utilized either separately or together. For example, Field et al. disclose a wall mount platform for generating anolyte and catholyte EA liquid.

Any of these apparatus can be configured to provide a visual indication of a functional operating state or operating characteristic of the electrolysis cell, wherein illumination of the indicator is visible through the liquid from a viewpoint that is external to the apparatus. The indicator light is not required to be in a direct line of sight of the observer, but may be out of sight. For example, the illumination might be visible due to diffusion and/or diffraction of the light, such as through the liquid.

In one example, a wall-mounted platform supports an electrolysis cell and a liquid flow path from an inlet of the platform, through the electrolysis cell, to an outlet of the platform. At least a portion of the flow path is at least translucent and visible from an exterior of the platform. The platform further includes an indicator light, such as that shown in FIG. 7, that illuminates the liquid along at least a portion of the flow path, such as along a tube and/or a reservoir of the platform.

13. Mobile Surface Cleaner

The features and methods described herein, such as those of the electrolysis cell, can be used in a variety of different applications, such on a spray bottle, a mobile surface cleaner, and/or a free-standing or wall-mount electrolysis platform. For example, they can be implemented onboard (or off-board) a mobile surface cleaner, such as a mobile hard floor surface cleaner, a mobile soft floor surface cleaner or a mobile surface cleaner that is adapted to clean both hard and soft floors or other surfaces, for example.

Field et al. U.S. Publication No. 2007/0186368 A1 various apparatus in which the features and methods described herein can be used, such as a mobile surface cleaner having a mobile body configured to travel over a surface. The mobile body has a tank for containing a cleaning liquid, such as tap water, a liquid dispenser and a flowpath from the tank to the liquid dispenser. An electrolysis cell is coupled in the flowpath. The electrolysis cell has an anode chamber and a cathode chamber separated by an ion exchange membrane and electrochemically activates tap water that has passed through the functional generator.

The functional generator converts the tap water into an anolyte EA liquid and a catholyte EA liquid. The anolyte EA liquid and the catholyte EA liquid can be separately applied to the surface being cleaned and/or sanitized, or can be combined on-board the apparatus to form a combination anolyte and catholyte EA liquid and dispensed together through a cleaning head, for example.

Figure 17:
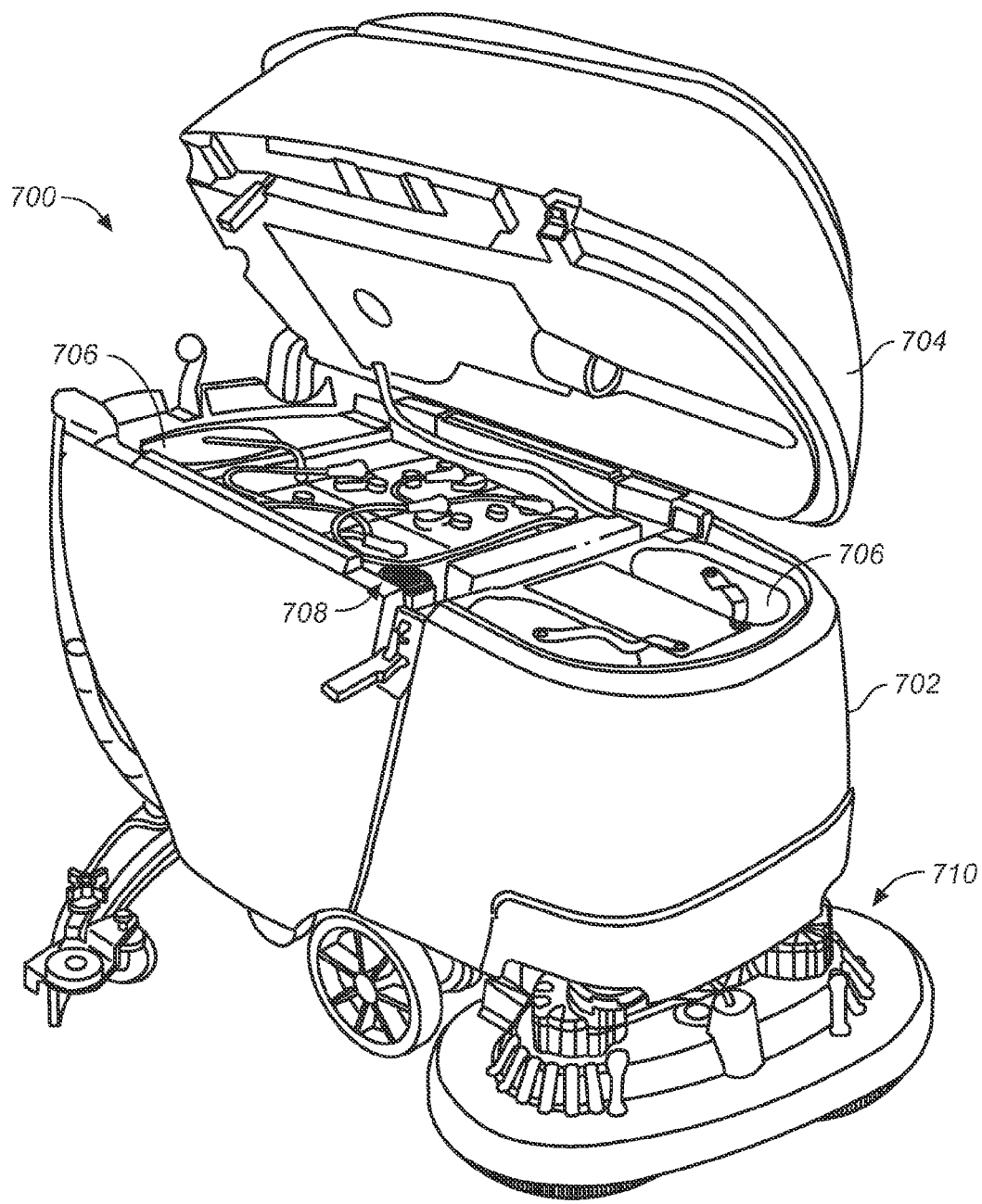
FIG. 17 is a perspective view of a mobile cleaning machine, which implements an electrolysis cell according to an example of the present disclosure.

FIG. 17 illustrates an example of a mobile hard and/or soft floor surface cleaner 700 disclosed in Field et al. U.S. Publication No. 2007/0186368 A1 in which one or more of the above-described features and/or methods can be implemented. FIG. 17 is a perspective view of cleaner 700 having its lid in an open position.

In this example, cleaner 700 is a walk-behind cleaner used to clean hard floor surfaces, such as concrete, tile, vinyl, terrazzo, etc. in other examples, cleaner 700 can be configured as a ride-on, attachable, or towed-behind cleaner for performing a cleaning and/or sanitizing operation as described herein. In a further example, cleaner 700 can be adapted to clean soft floors, such as carpet, or both hard and soft floors in further embodiments. Cleaner 700 may include electrical motors powered through an on-board power source, such as batteries, or through an electrical cord. Alternatively, for example, an internal combustion engine system could be used either alone, or in combination with, the electric motors.

Cleaner 700 generally includes a base 702 and a lid 704, which is attached along one side of the base 702 by hinges (not shown) so that lid 704 can be pivoted up to provide access to the interior of base 702. Base 702 includes a tank 706 for containing a liquid or a primary cleaning and/or sanitizing liquid component (such as regular tap water) to be treated and applied to the floor surface during cleaning/sanitizing operations. Alternatively, for example, the liquid can be treated onboard or offboard cleaner 700 prior to containment in tank 706. In addition, cleaner 700 includes an electrolysis cell 708, which treats the liquid prior to the liquid being applied to the floor being cleaned. The treated liquid can be applied to the floor directly and/or through a cleaning head 710, for example. The treated liquid that is applied to the floor can include an anolyte EA liquid stream, a catholyte EA liquid stream, both and anolyte and catholyte EA liquid streams and/or a combined anolyte and catholyte EA liquid stream. The cell 408 can include an ion selective membrane or be configured without an ion selective membrane.

Field et al. U.S. Publication No. 2007/0186368 A1 also discloses other structures on which the various structural elements and processes disclosed herein can be utilized either separately or together. For example, Field et al. disclose a wall mount platform for generating anolyte and catholyte EA liquid. This platform can be controlled with a control voltage pattern as disclosed herein, for example.

14. Wall-Mount Platform

Figure 18:
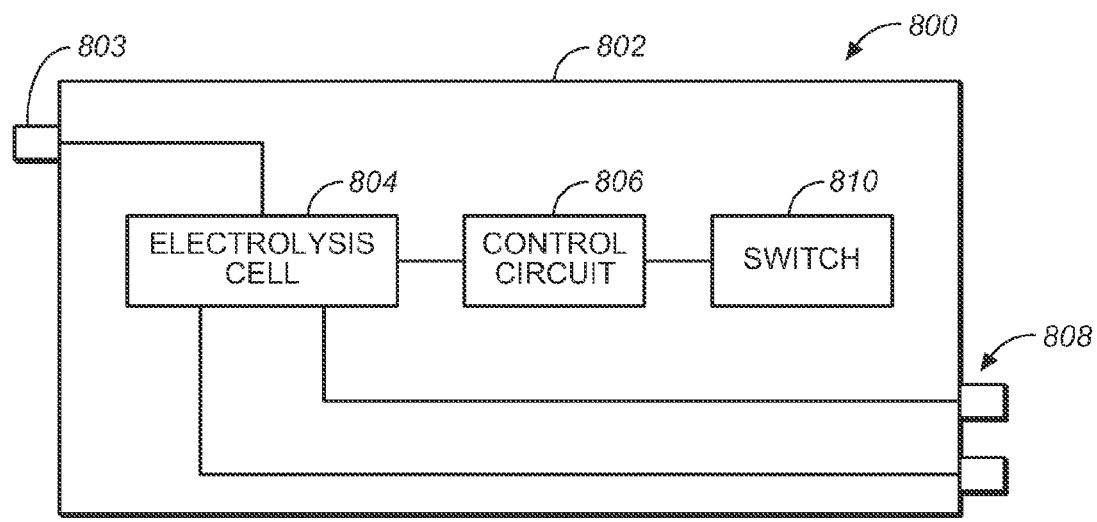
FIG. 18 is a simplified block diagram of an electrolysis cell that is mounted to a platform according to another embodiment.

For example, FIG. 18 illustrates a simplified block diagram of a cleaning liquid generator 800 that is mounted to a platform 802 according to an exemplary embodiment. Platform 802 can be configured to be mounted or placed in a facility on a floor, a wall, a bench or other surface, held by hand, carried by an operator or vehicle, attached on to another device (such as carried by a cleaning or maintenance trolley or mop bucket), or carried on a person. In one specific embodiment, platform 802 is mounted to the wall of a facility for loading cleaning devices, such as mop buckets, mobile cleaning machines, etc., with cleaning and/or sanitizing liquid.

Platform 802 includes an inlet 803 for receiving a liquid, such as tap water, from a source. Alternatively, for example, platform 802 can include a tank for holding a supply of liquid to be treated. Platform 802 further includes one or more electrolysis cells 804 and a control circuit 806 (such as those disclosed above). Electrolysis cell(s) 804 can have any of the structures described herein or any other suitable structure. Platform 802 can also include any other devices or components such as but not limited to those disclosed herein.

The flow path or paths from the output of electrolysis cell 804 can be configured to dispense anolyte EA liquid and catholyte EA liquid separately and/or blended anolyte and catholyte EA liquid through outlet 808. Unused anolyte or catholyte can be directed to a waste tank on platform 802 or to a drain outlet, for example. In embodiments in which both anolyte and catholyte EA are dispensed through outlet 808, the outlet can have separate anolyte and catholyte ports and/or a combined port, which delivers a blended mixture of catholyte and anolyte, for example, as discussed above. Further, any of the embodiments herein can include one or more storage tanks for containing the anolyte and/or catholyte produced liquid by the electrolysis cell.

In one specific embodiment, electrolysis cell 804 includes at least one anode and at least one cathode that are separated by at least one ion-selective membrane, forming one or more anode chambers and cathode chambers. Outlet 808 has separate anolyte and catholyte ports, which are fluidically coupled to the anode chambers and cathode chambers, respectively, without any fluid valving, for example. The control circuit 806 energizes the anodes and cathodes with a voltage pattern discussed above with reference to FIG. 6 such that each anolyte port supplies a substantially constant anolyte EA liquid output, and each catholyte port supplies a substantially constant catholyte EA liquid output. A substantially constant, relatively positive voltage is applied to the anodes, while a substantially constant, relatively negative voltage is applied to the cathodes. Periodically each voltage is briefly pulsed to a relatively opposite polarity to repel scale deposits.

If the number of anode electrodes is different than the number of cathode electrodes, e.g., a ratio of 3:2, or if the surface area of the anode electrode is different than the surface area of the cathode electrode, then the applied voltage pattern can be used in the above-manner to produce a greater amount of either anolyte or catholyte to emphasize cleaning or sanitizing properties of the produced liquid. Other ratios can also be used. Platform 802 further can include a switch or other user input device 810, if desired, for operating the control circuit to selectively invert the voltage patterns applied to each electrode to produce a greater amount of anolyte or catholyte depending upon the state of the switch.

15. All Surface Cleaner

Figure 19:
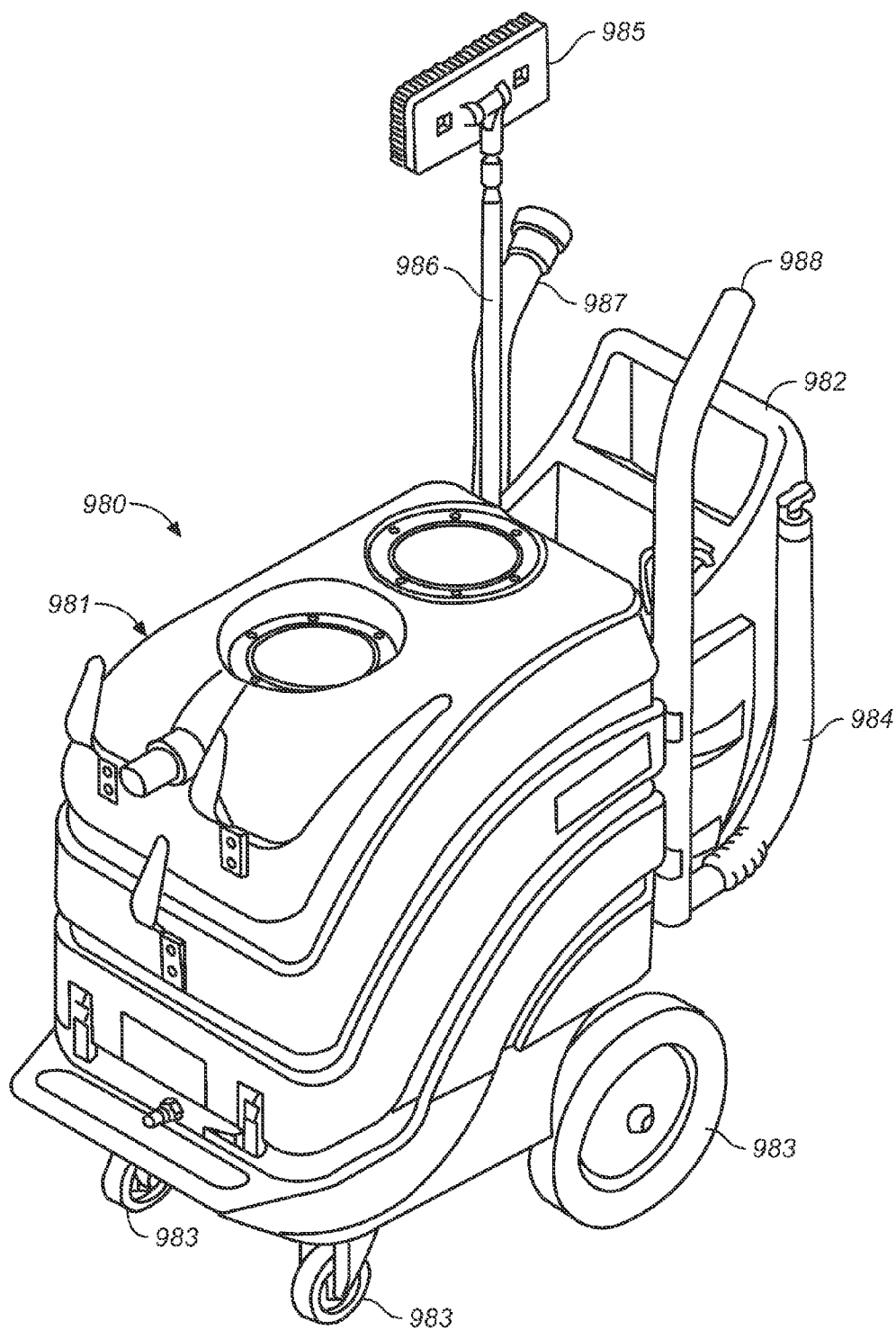
FIG. 19 is a perspective view of an all-surface cleaner according to another embodiment of the disclosure.

FIG. 19 is a perspective view of an all surface cleaning assembly 980, which is described in more detail in U.S. Pat. No. 6,425,958, which is incorporated herein by reference in its entirety. The cleaning assembly 980 is modified to include a liquid distribution path with one or more electrolysis cells with electrodes and a control circuit as described herein such as but not limited to those shown or described with reference to FIG. 1, for example, or any of the other embodiments disclosed herein. Cleaning assembly 980 can be constructed to deliver and optionally recover one or more of the following liquids, for example, to and from the floor being cleaned: anolyte EA water, catholyte EA water, blended anolyte and catholyte EA water, or other electrically-charged liquids. For example, liquid other than or in addition to water can be used.

Cleaning assembly 980 can be used to clean hard surfaces in restrooms or any other room having at least one hard surface, for example. Cleaning assembly 980 includes the cleaning device and the accessories used with the cleaning device for cleaning the surfaces, as described in U.S. Pat. No. 6,425,958. Cleaning assembly 980 includes a housing 981, a handle 982, wheels 983, a drain hose 984 and various accessories. The accessories can include a floor brush 985 having a telescoping and extending handle 986, a first piece 987 and a second piece 988 of a two piece double bend wand, and various additional accessories not shown in FIG. 19, including a vacuum hose, a blower hose, a sprayer hose, a blower hose nozzle, a spray gun, a squeegee floor tool attachment, a gulper tool, and a tank fill hose (which can be coupled to ports on assembly 980). The assembly has a housing that carries a tank or removable liquid container and a recovery tank or removable recovery liquid container. The cleaning assembly 980 is used to clean surfaces by spraying the cleaning liquid through a sprayer hose and onto the surfaces. The blower hose is then used to blow dry the surfaces and to blow the fluid on the surfaces in a predetermined direction. The vacuum hose is used to suction the fluid off of the surfaces and into the recovery tank within cleaning device 980, thereby cleaning the surfaces. The vacuum hose, blower hose, sprayer hose and other accessories used with cleaning assembly 980 can be carried with the cleaning device 980 for easy transportation.

In addition, similar to the embodiment shown in FIGS. 8-16, any of the apparatus shown in or described with FIGS. 17-19 can include one or more indicator lights 414 and/or 416 (shown in the block diagram of FIG. 7) positioned on the apparatus to illuminate the liquid itself, either prior to treatment by electrolysis cell 404 and/or after treatment. For example, the indicator light, when illuminated, generates luminous flux in the visible wavelength range that is visually perceptible through the liquid from a viewpoint that is exterior to the apparatus. For example, the liquid may diffuse at least a portion of the light, giving a visual impression that the liquid, itself, is illuminated. In one embodiment, the apparatus comprises a container, lumen or other element that contains the liquid and comprises a material and/or portion that is at least translucent and positioned to transmit at least some of the light produced by indicator 414 and/or 416 when illuminated. This container, lumen or other element is at least partially visible from an exterior of the apparatus. 16. Control Circuit for Spray Bottle Shown in FIGS. 8-16

Figure 20:
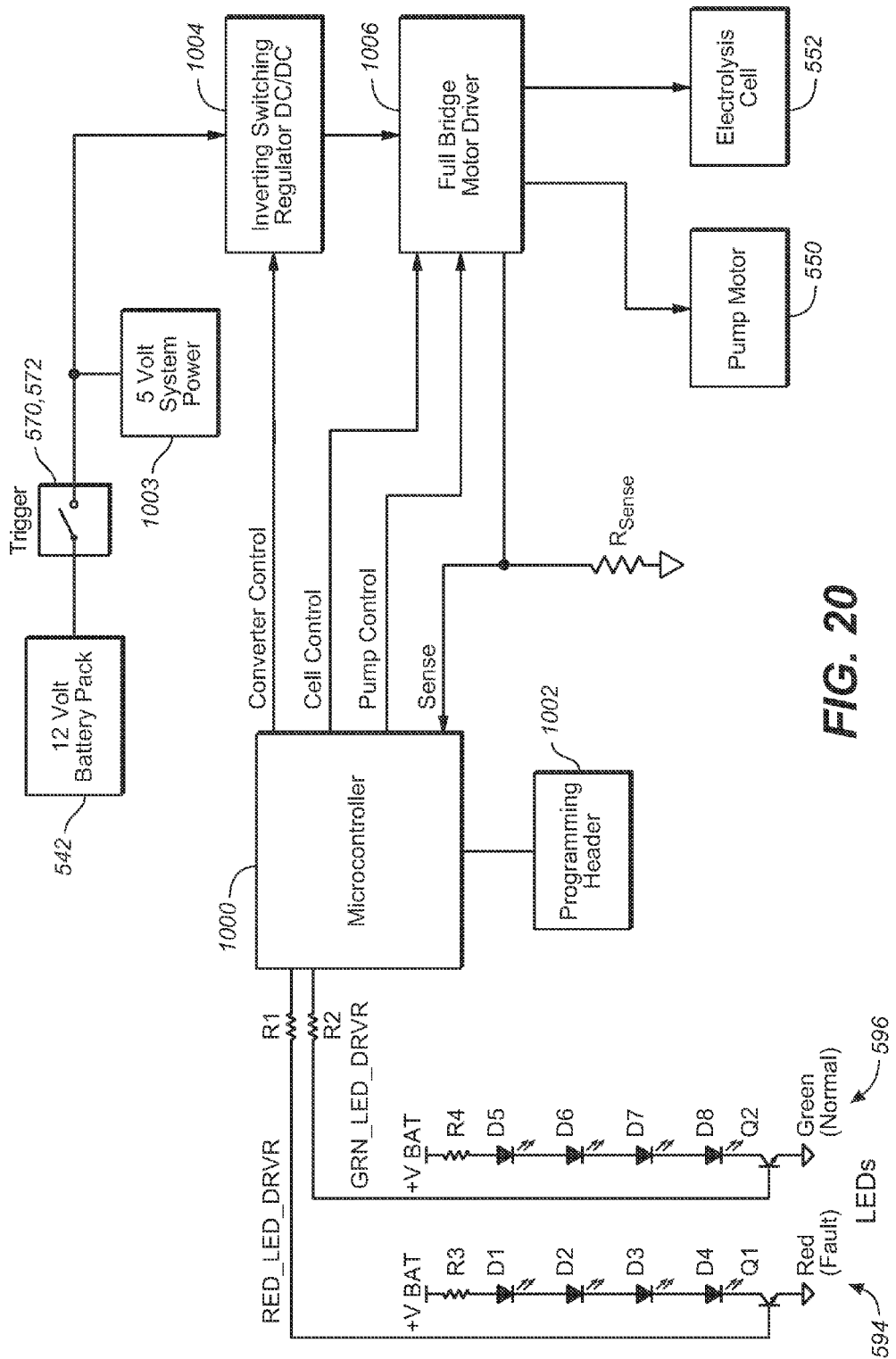
FIG. 20 is a block diagram illustrating a control circuit for controlling the various components within the hand-held spray bottle shown in FIGS. 8-16 according to an illustrating example of the disclosure.

FIG. 20 is a block diagram illustrating a control circuit for controlling the various components within the hand-held spray bottles 500, 500' shown in FIGS. 8-16 according to an illustrative example of the disclosure. The main components of the control circuit include a microcontroller 1000, a DC-to-DC converter 1004, and an output driver circuit 1006.

Power to the various components is supplied by a battery pack 542 carried by the bottle, as shown in FIG. 16B, for example. In a specific example, battery pack 542 includes 10 nickel-metal hydride batteries, each having a nominal output voltage of about 1.2 Volts. The batteries are connected in series, so the nominal output voltage is about 10V to 12.5V with a capacity of about 1800 milliampere-hours. Hand trigger 570,572 (shown in FIGS. 8A and 8B, for example) selectively applies the 12-volt output voltage from battery pack 542 to voltage regulator 1003 and to DC-to-DC converter 1004. Any suitable voltage regulator can be used, such as an LM7805 regulator from Fairchild Semiconductor Corporation. In a particular example, voltage regulator 1003 provides a 5 Volt output voltage for powering the various electrical components within the control circuit.

DC-to-DC converter 1004 generates an output voltage to be applied across the electrodes of electrolysis cell 552. The converter is controlled by microcontroller to step the drive voltage up or down in order to achieve a desired current draw through the electrolysis cell. In a particular example, converter 1004 steps the voltage up or down between a range of 8 Volts to 28 Volts (or greater) to achieve a current draw through electrolysis cell 552 of about 400 milliamps, as pump 550 pumps water from container 510, through cell 552 and out nozzle 508 (FIGS. 8A and 8B). The required voltage depends in part on the conductivity of the water between the cell's electrodes.

In a particular example, DC-to-DC converter 1004 includes a Series A/SM surface mount converter from PICO Electronics, Inc. of Pelham, N.Y., U.S.A. In another example, converter 1004 includes an NCP3064 1.5A Step-Up/Down/Inverting Switching regulator from ON Semiconductor of Phoenix, Ariz., U.S.A, connected in a boost application. Other circuits can be used in alternative embodiments.

Output driver circuit 1006 selectively reverses the polarity of the driving voltage applied to electrolysis cell 552 as a function of a control signal generated by microcontroller 1000. For example, microcontroller 1000 can be configured to alternate polarity in a predetermined pattern, such that shown and/or described with reference to FIG. 6. Output driver 1006 can also provide an output voltage to pump 550. Alternatively, for example, pump 550 can receive its output voltage directly from the output of trigger switch 570, 572.

In a particular example, output driver circuit 1006 includes a DRV 8800 full bridge motor driver circuit available from Texas Instruments Corporation of Dallas, Tex., U.S.A. Other circuits can be used in alternative embodiments. The driver circuit 1006 has an H-switch that drives the output voltage to electrolysis cell 552 according to the voltage pattern controlled by the microcontroller. The H-switch also has a current sense output that can be used by the microcontroller to sense the current drawn by cell 552. Sense resistor $R_{SENSE}$ develops a voltage that is representative of the sensed current and is applied as a feedback voltage to microcontroller 1000. Microcontroller 1000 monitors the feedback voltage and controls converter 1004 to output a suitable drive voltage to maintain a desired current draw.

Microcontroller 1000 also monitors the feedback voltage to verify that electrolysis cell 552 and/or pump 550 is operating properly. As discussed above, microcontroller 1000 can operate LEDs 594 and 596 as a function of the current levels sensed by output driver circuit 1006. For example, microcontroller 1000 can turn off (or alternatively, turn on) one or both of the sets of LEDs 594 and 596 as a function of whether the current level sensed is above or below a threshold level or within a range.

In a particular embodiment, microcontroller 1000 can include any suitable controller, such as an MC9S08SH4CTG-ND Microcontroller available from Digi-Key Corporation of Thief River Falls, Minn., U.S.A.

In the example shown in FIG. 20, the illumination control portion of the circuit includes output resistors R1 and R2 and a first, "red" LED control leg formed by pull-up resistor R3, red LED diodes D-D4, and pull-down transistor Q1. Microcontroller 1000 has a first control output, which selectively turns on and off red LEDs D1-D4 by turning on and off transistor Q1. The illumination control portion of the circuit further a second, "green" LED control leg formed by pull-up resistor R4, green LED diodes D5-D8, and pull-down transistor Q2. Microcontroller 1000 has a second control output, which selectively turns on and off green LEDs D5-D8 by turning on and off transistor Q2.

The control circuit further includes a control header 1002, which provides an input for reprogramming microcontroller 1000.

In one particular example, the elements 1000, 1002, 1003, 1004, 1006, R1-R4, D1-D8 and Q1-Q2 reside on circuit board 540, shown in FIG. 16B.

In addition, the control circuit shown in FIG. 20 can include a charging circuit (not shown) for charging the batteries within battery pack 542 with energy received through the power jack 523 shown in FIG. 8C.

One or more of the control functions described herein can be implemented in hardware, software, firmware, etc., or a combination thereof. Such software, firmware, etc. is stored on a computer-readable medium, such as a memory device. Any computer-readable memory device can be used, such as a disc drive, a solid state drive, flash memory, RAM, ROM, a set of registers on an integrated circuit, etc.

Although the present disclosure has been described with reference to one or more embodiments, workers skilled in the art will recognize that changes may be made in form and detail without departing from the spirit and scope of the disclosure and/or the appended claims.

What is claimed is:

1. An apparatus comprising:
an electrolysis cell;
a liquid flow path that passes through the electrolysis cell;
an indicator light arranged relative to the flow path such that luminous flux radiated from the light illuminates at least a portion of the flow path on the apparatus and is visually perceptible through liquid in the flow path from a viewpoint that is exterior to the apparatus; and
a control circuit, which is configured to illuminate the indicator light as a function of whether electrical power is applied to the electrolysis cell and as a function of electrical current drawn by the electrolysis cell when the electrical power is applied.

2. The apparatus of claim 1, wherein the indicator light comprises:
a first indicator light, which has a first color, wherein the control circuit is configured to turn the first indicator light on when the electrical current is within a first current range and off when the electrical current is outside the first current range; and
a second indicator light, which has a second, different color, wherein the control circuit is configured to turn the second indicator light on when the electrical current is outside the first current range and off when the electrical current is within the first current range.

3. The apparatus of claim 1 and further comprising:
a housing comprising a window that is at least translucent and through which at least a portion of the luminous flux radiates.

4. The apparatus of claim 1 and further comprising:
a housing comprising a translucent portion through which at least a portion of the luminous flux radiates.

5. The apparatus of claim 1, wherein the liquid flow path comprises a container that is upstream of the electrolysis cell along the flow path and the indicator light is positioned to illuminate liquid within the container.

6. The apparatus of claim 1, wherein the apparatus comprises a hand-held spray bottle, which carries:
the electrolysis cell;
a pump coupled in the flow path;
a container in the flow path for containing liquid to be treated by the electrolysis cell; and
a nozzle in the flow path; and
a switch, which has a first state in which the control circuit energizes the pump and the electrolysis cell and a second state in which the control circuit de-energizes the pump and the electrolysis cell, and wherein the control circuit enables illumination of the indicator light as a function of the electrical current drawn by the electrolysis cell when the switch is in the first state and disables the indicator light when the switch is in the second state.

7. The apparatus of claim 6, wherein the indicator light is positioned to illuminate liquid within the container.

8. The apparatus of claim 7, wherein at least a portion of the container is at least translucent.

9. The apparatus of claim 8, wherein the bottle further comprises a housing in which the container is located, wherein the housing comprises a portion that is at least translucent, through which at least a portion of the luminous flux within the container is visible from a viewpoint that is external to the housing.

10. The apparatus of claim 1, further comprising:
a current sensor coupled to the electrolysis cell and having a sensed current output, which is fed back to the control circuit and is indicative of the electrical current drawn by the electrolysis cell.

11. A method comprising:
carrying a liquid in a hand-held spray bottle;
electrolyzing the liquid with an electrolysis cell carried by the bottle to produce electrolyzed liquid;
dispensing the electrolyzed liquid;
sensing electrical current drawn by the electrolysis cell when electrical power is applied to the electrolysis cell during the step of electrolyzing; and
illuminating at least a portion of at least one of the liquid or the electrolyzed liquid with an indicator light as a function of a level of the electrical current sensed when electrical power is applied to the electrolysis cell, such that luminous flux radiated from the light is visually perceptible through the liquid or the electrolyzed liquid in the flow path on the bottle from a viewpoint that is exterior to the bottle.

12. A device comprising:
a container;
a switch having a first state and a second state;
a nozzle;
a liquid flow path extending from an interior of the container to the nozzle;
an electrolysis cell in the flow path;
a pump in the flow path, wherein the pump and the electrolysis cell are energized when the switch is in the first state and de-energized when the switch is in the second state; and
an indicator light, which is positioned relative to illuminate at least at least a portion of the flow path on the bottle such that luminous flux radiated from the light is visually perceptible only through the portion of the flow path from a viewpoint that is exterior to the device;
a current sensor coupled to sense electrical current drawn by the electrolysis cell when electrical power is applied to the electrolysis cell; and
a control circuit, which is configured to enable illumination of the indicator light as a function of the sensed electrical current drawn by the electrolysis cell when the switch is in the first state and to disable illumination of the indicator light when the switch is in the second state.

13. The device of claim 12, wherein the device is a hand-held spray bottle.

14. The device of claim 12, wherein the indicator light comprises:
a first indicator light, which has a first color, wherein the control circuit is configured to turn the first indicator light on when the electrical current is inside a first current range and off when the electrical current is outside the first current range; and
a second indicator light, which has a second, different color, wherein the control circuit is configured to turn the second indicator light on when the electrical current is outside the first current range and off when the electrical current is inside the first current range.

15. The device of claim 12, wherein the indicator light is positioned such that luminous flux from the indicator light passes through liquid contained the container, upstream of the electrolysis cell.

* * * * *